(12) United States Patent
Johnson et al.

(10) Patent No.: US 8,841,460 B2
(45) Date of Patent: Sep. 23, 2014

(54) TUNABLE PHENYLACETYLENE HOSTS

(71) Applicant: State of Oregon, acting by and through the State Board of Higher Education on behalf of University of Oregon, Eugene, OR (US)

(72) Inventors: Darren W. Johnson, Eugene, OR (US); Calden Carroll, Eugene, OR (US); Michael M. Haley, Eugene, OR (US); Jeff Engle, Eugene, OR (US)

(73) Assignee: State of Oregon Acting by and Through the State Board of Higher Education on Behalf of the University of Oregon, Igene, OR (US)

( * ) Notice: Subject to any disclaimer, the term of this patent is extended or adjusted under 35 U.S.C. 154(b) by 0 days.

(21) Appl. No.: 13/715,979

(22) Filed: Dec. 14, 2012

(65) Prior Publication Data
US 2014/0031559 A1 Jan. 30, 2014

Related U.S. Application Data

(60) Provisional application No. 61/576,940, filed on Dec. 16, 2011.

(51) Int. Cl.
C07D 213/20 (2006.01)
C07D 213/40 (2006.01)

(52) U.S. Cl.
USPC ............................. 546/337; 546/329; 546/347

(58) Field of Classification Search
None
See application file for complete search history.

(56) References Cited

U.S. PATENT DOCUMENTS 7,803,946 B2    9/2010  Haley et al.
2008/0167472 A1 7/2008  Haley et al.

OTHER PUBLICATIONS

Berryman et al., "Water and hydrogen halides serve the same structural role in a series of 2+2 hydrogen-bonded dimers based on 2,6-bis(2-anilinoethynyl)pyridine sulfonamide receptors," *Angewandte Chemie* 47(1):117-120, 2008.
Butler et al., "Bipyridylacetylenes 1: the synthesis of some bipyridylacetylenes via the palladium-catalyzed coupling of acetylenes with 2,2'-dibromobipyridyl, and the single crystal X-ray structure of 6,6'-bisphenylethynyl-2,2'-bipyridine," *Can. J. Chem.* 69:1117-1123, 1991.
Carroll et al., "Protonation activates anion binding and alters binding selectivity in new inherently fluorescent 2,6-bis(2-anilinoethynyl)pyridine bisureas," *Chemical Communications* 2520-2522, 2009 (Available online Mar. 27, 2009).
Carroll et al., "Anion-dependent fluorescence in bis(anilinoethynyl)pyridine derivatives: switchable ON-OFF and OFF-ON responses," *Chemical Communications* 47:5539-5541, 2011.
Dash et al., "Diarylethynyl amides that recognize the parallel conformation of genomic promoter DNA G-quadruplexes," *Journal of the American Chemical Society* 130(47):15950-15956, 2008 (published online Nov. 4, 2008).
Dash et al., "G-quadruplex recognition by bis-indole carboxamides," *Chemical Communications* 26:3055-3057, 2008.

(Continued)

Primary Examiner — Zinna Northington Davis
(74) Attorney, Agent, or Firm — Klarquist Sparkman, LLP

(57) ABSTRACT

A compound, or a salt thereof, having the formula

Formula III

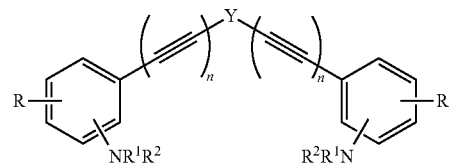

wherein Y is

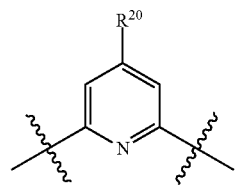

n is 1 or 2;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

$R^1$ is H, lower alkyl or aralkyl;

$R^2$ is selected from H, acyl, aralkyl, phosphonyl, $—SO_2R^3$; $—C(O)R^5$; $—C(O)OR^7$ or $—C(O)NR^9R^{10}$;

$R^3$; $R^5$; $R^7$; $R^9$ and $R^{10}$ independently are selected from H, lower alkyl, aralkyl or aryl; and $R^{20}$ is selected from alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

16 Claims, 3 Drawing Sheets
(3 of 3 Drawing Sheet(s) Filed in Color)

(56) References Cited

OTHER PUBLICATIONS

Droz et al., "Synthesis of highly-functionalized, optically active disaccharide receptors by sequential aryl-alkyne cross-and oxidative acetylenic homo-coupling," *J. Chem. Soc.* 4224-4226, 2000.

Engle et al., "Synthesis and Optoelectronic Properties of 2,6-Bis(2-anilino-ethynyl)pyridine Scaffolds," *Chem. Sci.* 3:1105-1110, 2012.

Ferrara et al., "Synthesis and Characterization of a Copper(1) Triflate Complex of 1,2:5,6:9,10-Tribenzocyclododeca-1,5,9-triene-3,7,11-triyne," *Organometallics* 6:676-678, 1987.

Ferrara et al., "Synthesis and Characterization of the First Transition-Metal Complex of 1,2:5,6:9,10-Tribenzocyclododeca-1,5,9-triene-3,7,11-triyne," *J. Am. Chem. Soc.* 107:6719-6721, 1985.

Gerhardt et al., "Controlling polymer properties through dynamic metal-ligand interactions: supramolecular cruciform made easy," *Chem. Eur. J.* 13(16):4467-4474, 2007.

Gerhardt et al., "Supramolecular cruciforms," *Chemical Communications* 20:2141-2143, 2006.

Hauck et al., "Phenothiazine Cruciforms: Synthesis and Metallochromic Properties," *Journal of Organic Chemistry* 72(18):6714-6725, 2007.

Jia et al., "Novel Phosphorescent Cyclometalated Organotin(IV) and Organolead(IV) Complexes of 2,6-Bis(2'-indolyl)pyridine and 2,6-Bix[2'-(7-azaindolyl)]pyridine," *Organometallics* 22:4070-4078, 2003.

Johnson et al., "Aryl-Acetylene Scaffolding as Receptors in Supramolecular Chemistry," presentation through Department of Chemistry & Materials Science Institute of the University of Oregon, 26 pages, 2007.

Johnson et al., "Synthesis and characterization of pyridine- and thiophene-based platinacyclynes," *Journal of Organometallic Chemistry* 691:413-421, 2006 (available online Oct. 25, 2005).

Leininger et al., "Self-Assembly of Discrete Cyclic Nanostructures Mediated by Transition Metals," *Chem. Rev.* 100:853-908, 2000.

McGrier et al., "Hydroxy-cruciforms," *Chemical Communications* 21:2127-2129, 2007.

Pucher et al., "Structure-Activity Relationship in D-π-A-π-D-Based Photoinitiators for the Two-Photon-Induced Photopolymerization Process," *Macromolecules* 10 pages, 2009.

Walters et al., "Experimental Studies of Light-Induced Charge Transfer and Charge Redistribution in (X2-Bipyridine)Re(CO)3C1 Complexes," *Inorganic Chemistry* 41:2909-2919, 2002.

Wilson et al., "Switching of Intermolecular Charge Transfer in Cruciforms: Metal Ion Sensing," *Journal of the American Chemical Society* 172(12):4124-4125, 2005.

Zucchero et al., "Cruciforms as functional fluorophores: Response to protons and selected metal ions," *Journal of the American Chemical Society* 128(36):11872-11881, 2006.

TUNABLE PHENYLACETYLENE HOSTS

CROSS-REFERENCE TO RELATED APPLICATION

This application claims the benefit of U.S. Provisional Application No. 61/576,940, which was filed on Dec. 16, 2011, and is incorporated herein by reference in its entirety.

ACKNOWLEDGMENT OF GOVERNMENT SUPPORT

This invention was made with government support under grant number GM087398-01A1 awarded by the National Institutes of Health, grant number CHE-0718242 awarded by the National Science Foundation, grant number GK12 (DGE-0742540) awarded by the National Science Foundation, and grant number IGERT (DGE-0549503). The government has certain rights in the invention.

BACKGROUND

The synthesis of new molecules designed to bind or sense and report the presence of a particular substrate is an area of chemistry that is attracting attention. There exists a general lack of ligand-specific host molecules, such as specific hosts for toxic ions and small molecules of interest. There also is a dearth of specific hosts that report binding events, for example by exhibiting a spectral shift upon binding, such as an altered fluorescent response. In fact, structures of fluorescent coordination complexes are generally poorly understood, which makes the rational design of functional hosts and sensors a challenging undertaking.

The detection of ionic species, in particular the selective detection of a particular ionic species in the presence of another is difficult. The detection of anionic species is a particular challenge, as anions are difficult to bind and are generally larger than cations leading to a smaller charge-to-radius ratio.

SUMMARY

Disclosed herein are host or receptor compounds that bind targets of interest. In one embodiment the compounds bind ions, such as metal ions. In particular, toxic metal ions, including anions and cations are bound by embodiments of the disclosed host compounds.

In one embodiment the host compounds and salts thereof have the formula

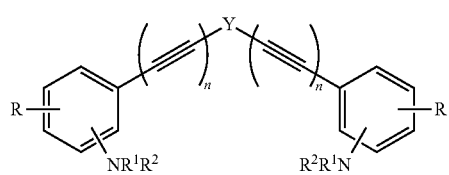

Formula I wherein Y represents an optionally substituted aromatic group;
n is 1 or 2;
R is H or lower alkyl;
$R^1$ is H, lower alkyl or aralkyl;
$R^2$ is selected from H, acyl, aralkyl, phosphonyl, —$SO_2R^3$; —$C(O)R^5$; —$C(O)OR^7$ and —$C(O)NR^9R^{10}$;
$R^3$; $R^5$; $R^7$; $R^9$ and $R^{10}$ independently are selected from H, lower alkyl, aralkyl and aryl.

In a further embodiment the host compounds and salts thereof have the formula

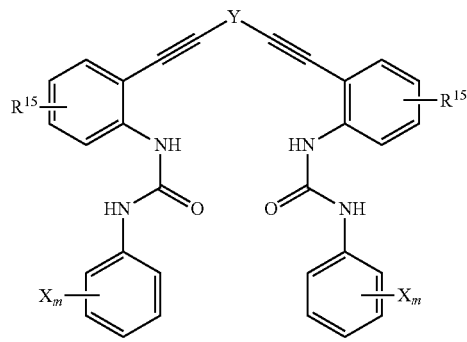

Formula II wherein Y represents an optionally substituted aromatic group;
each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;
each X is independently halogen or a polyether moiety; and
m is 1 to 5, provided that if X is halogen then m is 2 to 5.

In a further embodiment the host compounds and salts thereof have the formula

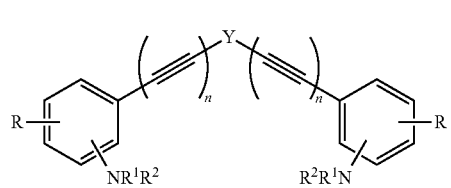

Formula III wherein Y is

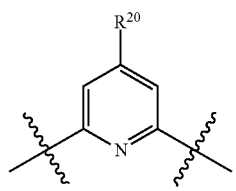

n is 1 or 2;
each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;
$R^1$ is H, lower alkyl or aralkyl;
$R^2$ is selected from H, acyl, aralkyl, phosphonyl, —$SO_2R^3$; —$C(O)R^5$; —$C(O)OR^7$ or —$C(O)NR^9R^{10}$;
$R^3$; $R^5$; $R^7$; $R^9$ and $R^{10}$ independently are selected from H, lower alkyl, aralkyl or aryl; and
$R^{20}$ is selected from alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

In another embodiment the host compounds and salts thereof have the formula

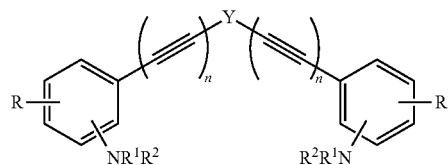

Formula IV wherein Y is selected from

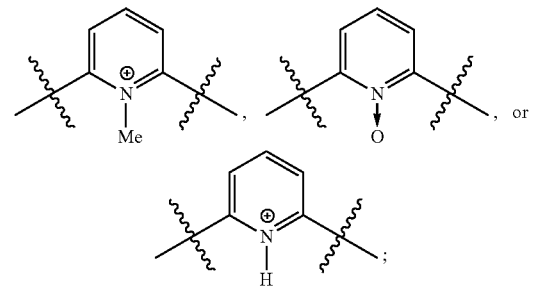

n is 1 or 2;
each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;
$R^1$ is H, lower alkyl or aralkyl;
$R^2$ is selected from H, acyl, aralkyl, phosphonyl, —$SO_2R^3$; —$C(O)R^5$; —$C(O)OR^7$ or —$C(O)NR^9R^{10}$;
$R^3$; $R^5$; $R^7$; $R^9$ and $R^{10}$ independently are selected from H, lower alkyl, aralkyl or aryl.

In a further embodiment the host compounds and salts thereof have the formula

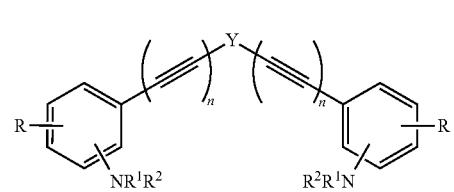

Formula V wherein Y represents an optionally substituted aromatic group;
n is 1 or 2;
each R is independently H, a polyether moiety, substituted carboxyl, alkoxy, or haloalkyl, provided that at least one R is not H, and that R is not methoxy or trifluoromethyl;
$R^1$ is H, lower alkyl or aralkyl;
$R^2$ is selected from H, acyl, aralkyl, phosphonyl, —$SO_2R^3$; —$C(O)R^5$; —$C(O)OR^7$ or —$C(O)NR^9R^{10}$; and
$R^3$; $R^5$; $R^7$; $R^9$ and $R^{10}$ independently are selected from H, lower alkyl, aralkyl or aryl.

In an additional embodiment the host compounds and salts thereof have the formula

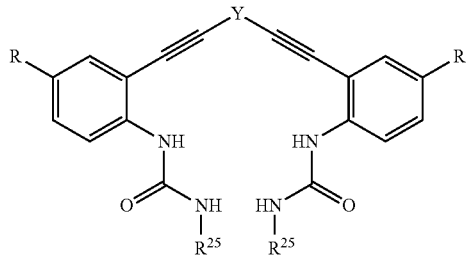

Formula VI wherein Y represents an optionally substituted aromatic group;
each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl; and
each $R^{25}$ is independently —$CHR^{26}R^{27}$ or —$NR^{26}R^{27}$ wherein $R^{26}$ and $R^{27}$ are each independently selected from H, alkyl, substituted alkyl, aryl, or substituted aryl, provided that at least one of $R^{26}$ or $R^{27}$ is alkyl, substituted alkyl, aryl, or substituted aryl.

Exemplary compounds exhibit shifts in their spectral properties upon ligand binding. Accordingly, also disclosed are methods for using the host compounds to detect targets of interest, including neutral, cationic and anionic targets.

The foregoing and other objects, features, and advantages will become more apparent from the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 (on the left) shows the electronic absorption of bis(arylethynyl)pyridines 6-9. FIG. 1 (on the right) shows the excitation/emission spectra of bis(arylethynyl)pyridines 6-9.

DETAILED DESCRIPTION

Figure 1:
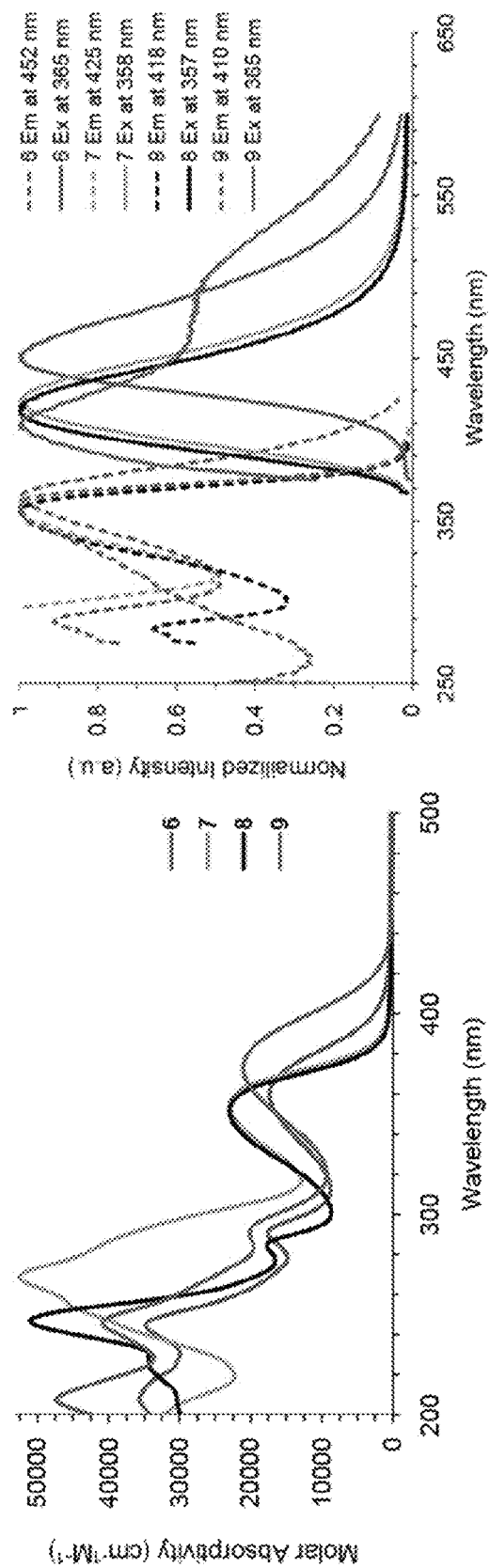
FIG. 1 shows the absorption spectra for several bis(arylethynyl)pyridine cores disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Ranges can be expressed herein as from "about" one particular value, and/or to "about" another particular value.

When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Acyl" refers group of the formula RC(O)— wherein R is an organic group.

The term "aliphatic" includes alkyl, alkenyl, alkynyl, halogenated alkyl and cycloalkyl groups as described above. A "lower aliphatic" group is a branched or unbranched aliphatic group having from 1 to 10 carbon atoms.

The term "alkoxy" refers to a straight, branched or cyclic hydrocarbon configuration and combinations thereof, including from 1 to 20 carbon atoms, preferably from 1 to 10 carbon atoms, more preferably from 1 to 4 carbon atoms, that includes an oxygen atom at the point of attachment. An example of an "alkoxy group" is represented by the formula —OR, where R can be an alkyl group, optionally substituted with, e.g., an alkenyl, alkynyl, aryl, aralkyl, cycloalkyl, halogenated alkyl, or heterocycloalkyl group as described herein. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers an aliphatic group that is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" refers to the formula —C(O)NRR', wherein R and R' independently can be a hydrogen, alkyl, alkenyl, alkynyl, aryl, aralkyl, cycloalkyl, halogenated alkyl, or heterocycloalkyl group described above.

The term "aralkyl" refers to an alkyl group that is substituted with one or more aryl groups (described below). A particular example of an aralkyl group is a benzyl group.

The term "aryl" refers to any carbon-based aromatic group including, but not limited to, phenyl, naphthyl, etc. The term "aromatic" also includes "heteroaryl groups," which are defined as aromatic groups that have at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine. "Carbonyloxy" refers to a group of the —OC(O)R where R is an aliphatic (e.g., alkyl) or aromatic (e.g., aryl) group.

"Carbonate" refers to a group of the formula —OC(O)O—. "Substituted carbonate" refers to a group of the formula —OC(O)OR. Likewise, as used herein the term "carbamate" refers to a group of the formula —OC(O)N(R)—, wherein R is H, or an aliphatic group, such as a lower alkyl group or an aralkyl group.

"Carboxyl" refers to a —COOH radical. Substituted carboxyl refers to —COOR where R is aliphatic, heteroaliphatic, alkyl, heteroalkyl, or a carboxylic acid or ester.

"Optional" or "optionally" means that the subsequently described event or circumstance can but need not occur, and that the description includes instances where said event or circumstance occurs and instances where it does not. Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "phosphoryl" refers to moieties of the formula —P(O)OR—, wherein R may be H, an aliphatic or aromatic moiety, a cation or a lone pair of electrons. Phosphoryl moieties may be further substituted to form phosphoramidates, phosphates and phosphonates.

The term "polyether moiety" may be an oligomer (which is inclusive of dimers and higher repeating units) or a polymer. Illustrative polyether moieties include those derived from an aliphatic polyether (e.g., paraformaldehyde, polyethylene glycol (PEG), polypropylene glycol, and polytetramethylene glycol, and those derived from an aromatic polyether (e.g., polyphenyl ether or poly(p-phenylene oxide)). A preferred polyether moiety is derived from PEG, also referred to herein as a poly(ethylene oxide). The PEG may be a straight chain PEG or a branched PEG. PEG is also inclusive of methoxypolyethylene glycol. In certain embodiments, the number of repeating ethylene oxide units in the PEG moiety may range from 2 to 50, more particularly from 2 to 10. The polyether moiety may be covalently bonded to the core motif via PEGylation procedures.

The term "sulfonyl" refers to the radical —SO$_2$—. The sulfonyl group can be further substituted with a variety of groups to form, for example, sulfonic acids, sulfonamides, sulfonate esters and sulfones.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure.

The disclosed host compounds are useful, inter alia, as ion binding compounds. By way of example, specific anions bound by the disclosed compounds include, but are not limited to, toxic metal anions, halide anions, carboxylates, phosphates, sulfates, oxalates, terephthalates, phospholipids, nucleotides, oligonucleotides, DNA, RNA, anionic polyoxometalates, or oxoanions such as pertechnetate.

The structural formulas provided herein include salts of the illustrated compounds. Such salts can be formed when disclosed host compounds possess at least one basic group that can form acid-base salts with acids. Examples of basic groups present in exemplary disclosed host compounds include amino groups or imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Similarly, salts can be formed when disclosed host compounds possess at least one acidic group that can form acid-base salts with bases. Examples of acidic groups present in exemplary disclosed host compounds include carboxylic acid moieties and sulfonamide groups. Compounds that include at least one acidic group can form an acid-base salts with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. In addition, quaternary ammonium counterions also can be used.

Additionally, the structural formulas herein are intended to cover, where applicable, solvated as well as unsolvated forms of the compounds. "Solvate" refers to a compound physically associated with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compounds, methanol associated compounds, and the like. "Hydrate" is a solvate wherein the solvent molecule(s) is/are $H_2O$, Solvate complexes may be described in shorthand form for example as $(1.H_2O)_2$, which refers to a hydrate, more specifically a 2+2 complex of compound 1 with water.

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

In one embodiment, the disclosed host compounds have the formula

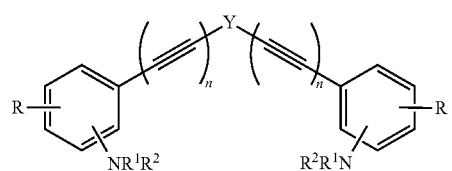

wherein Y represents an optionally substituted aromatic group;

n is 1 or 2;

R is H or lower alkyl;

$R^1$ is H, lower alkyl or aralkyl;

$R^2$ is selected from H, acyl, aralkyl, phosphonyl, —$SO_2R^3$; —$C(O)R^5$; —$C(O)OR^7$ and —$C(O)NR^9R^{10}$;

$R^3$; $R^5$; $R^7$; $R^9$ and $R^{10}$ independently are selected from H, lower alkyl, aralkyl and aryl.

In embodiments wherein n is 1, the disclosed host compounds can be represented by the formula

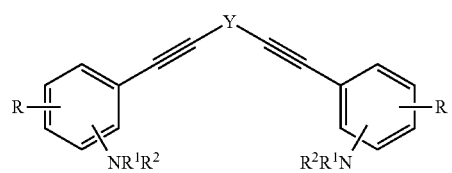

With reference to the generic formulas above, a guest molecule can bind in the cavity created between the aromatic group "Y" and the functional groups appended to the aniline nitrogens "$R^1$ and $R^2$".

With continued reference to the general formula above, such compounds can be cyclized, for example, by covalently linking an $R^1$ or $R^2$ group to another. Thus, macrocyclic compounds can be formed by linking an $R^1$ or $R^2$ group to another $R^1$ or $R^2$ group on a different aniline nitrogen.

With continued reference to the formula above, the R group can be selected for several purposes. Typically, R is selected to tune or tailor the electronics of the ring by selecting an electron donating or electron withdrawing and/or conjugated group. In other examples, R is selected for detection purposes, or, for instance, to affect the solubility of the overall molecule. Suitable R groups include, without limitation those listed in Table 1.

| Substituent | Hammett constant ($\sigma_{para}$) |
|---|---|
| —H | 0.00 |
| —$OCH_3$ | −0.27 |
| —$CH_3$ | −0.04 |
| —$CH_2CH_3$ | −0.05 |
| —$C(CH_3)_3$ | |
| —F | 0.06 |
| —Cl | 0.23 |

| Substituent | Hammett constant ($\sigma_{para}$) |
|---|---|
| —Br | 0.23 |
| —I | 0.18 |
| —CF$_3$ | 0.54 |
| —OCF$_3$ | |
| —NO$_2$ | 0.78 |
| 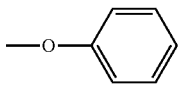 | |
| —N$_3$ | |
| —CN | 0.66 |
| —OH | −0.37 |
| —NH$_2$ | −0.66 |
|  | −0.83 |
|  | 0.45 |
| —SO$_3^-$ | 0.09 |

The group "Y" can be any aromatic group, but typically Y comprises a heteroaromatic group. For example, in one embodiment, the group "Y" employed was a pyridyl group. Additional exemplary Y groups include, without limitation, bipyridyl, pyridinyl, pyrazinyl, pyrimidinyl, pyrrole, imidazole, triazole, thiophene, thiazole, furyl and oxazolyl groups. By way of example, such Y groups can be selected from

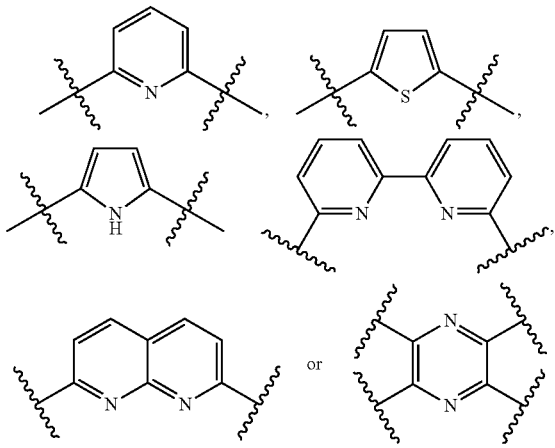

In other embodiments, Y is selected from, without limitation, the following heteroaromatic groups

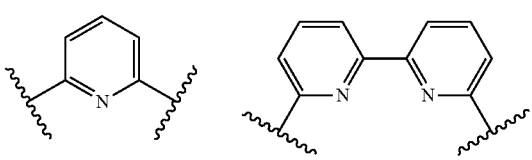

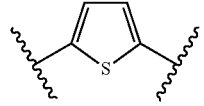

Other appropriate Y groups can be identified by those of skill in the art using the guidance provided by the present disclosure and by considering factors such as: the ring topology, bond angles, geometry of coordination to the guest, and number of available hydrogen bonds.

In one embodiment, the disclosed host compounds have the structure:

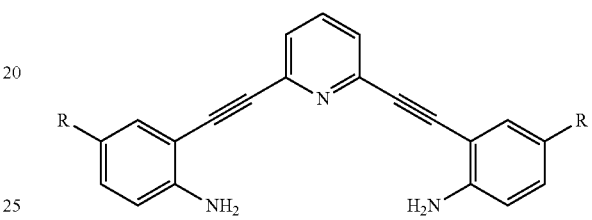

wherein R is H, aliphatic, such as lower alkyl (including optionally substituted lower alkyl), aralkyl, aryl, sulfonyl, phosphonyl, phosphate, sulfate, —XC(O)OR$^6$ and —XC(O)NR$^7$R$^8$; wherein X is optional and if present is selected from the group consisting of —O—, —N(R$^9$)— or —S—; R$^6$ is selected from lower alkyl, aralkyl and aryl; and R$^7$, R$^8$ and R$^9$ independently are selected from H, lower alkyl, aralkyl and aryl.

In one embodiment, Y is a hydrogen bond acceptor and/or donor. For example when Y is pyridyl, it is a hydrogen bond acceptor at high (basic) pH and a hydrogen bond donor when it is in its conjugate acid form at low pH.

In one embodiment the disclosed host compounds have the structure:

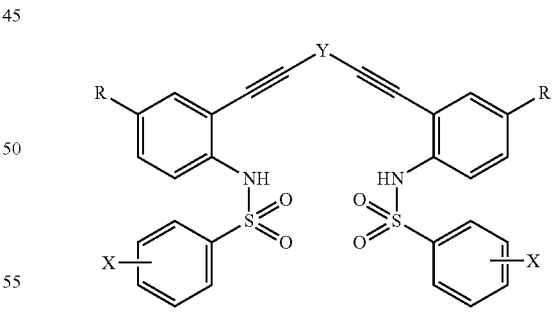

wherein X is selected from halogen, —OR$^{11}$, nitro, sulfonyl, phosphonyl, phosphate, sulfate, or optionally substituted lower alkyl;

and R$^{11}$ is H, acyl or optionally substituted lower alkyl. When X includes an optionally substituted lower alkyl moiety, optional substitutions include, without limitation hydroxy and sulfide moieties.

Particular examples of sulfonamide host compounds can be represented by the formula

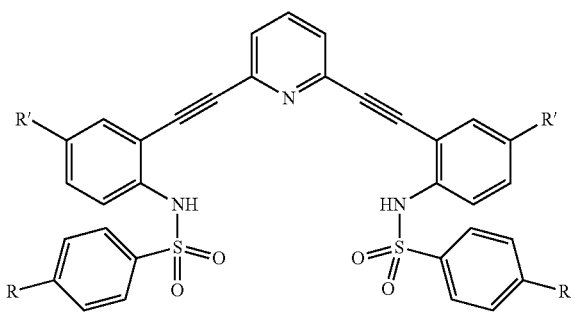

wherein R is selected from —OR, —SR, -Me, halo, such as —Br, and —NO$_2$, and wherein R' is, for each occurrence selected from H, lower alkyl and acyl. With reference to such sulfonamide compounds, they include acidic NH groups, which are good hydrogen bond donors.

Particular examples of such sulfonamide compounds have the formula

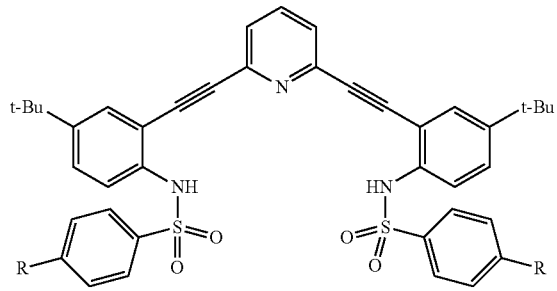

Additional embodiments include urea compounds, such as those of the formula:

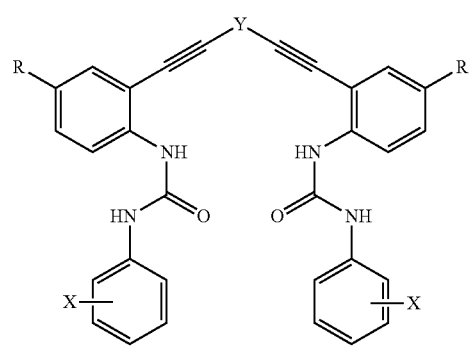

wherein R is lower alkyl and X is H, —OR$^{11}$, halogen, lower alkyl, phosphonyl, phosphate, sulfonyl or sulfate; and R$^{11}$ is H, acyl or optionally substituted lower alkyl.

Other urea compounds have the formula

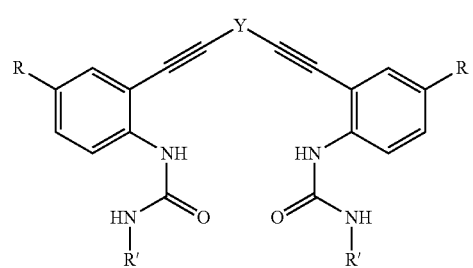

wherein R' is H or optionally substituted lower alkyl, such as methyl, t-butyl, octyl and the like. In one aspect, certain urea compounds can be represented by the formula

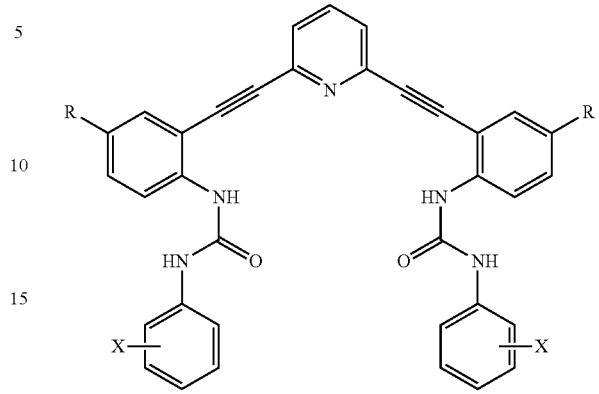

One such compound had the formula

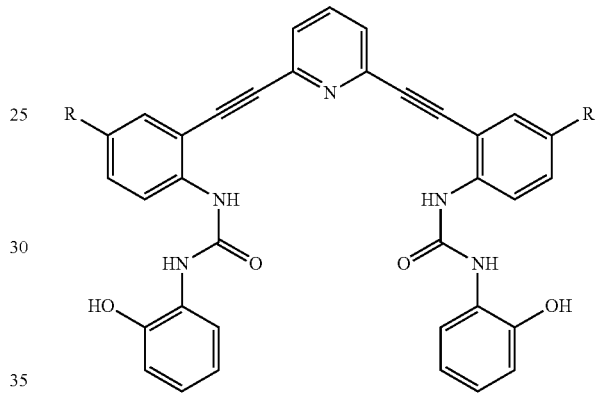

A second such urea compound has the formula

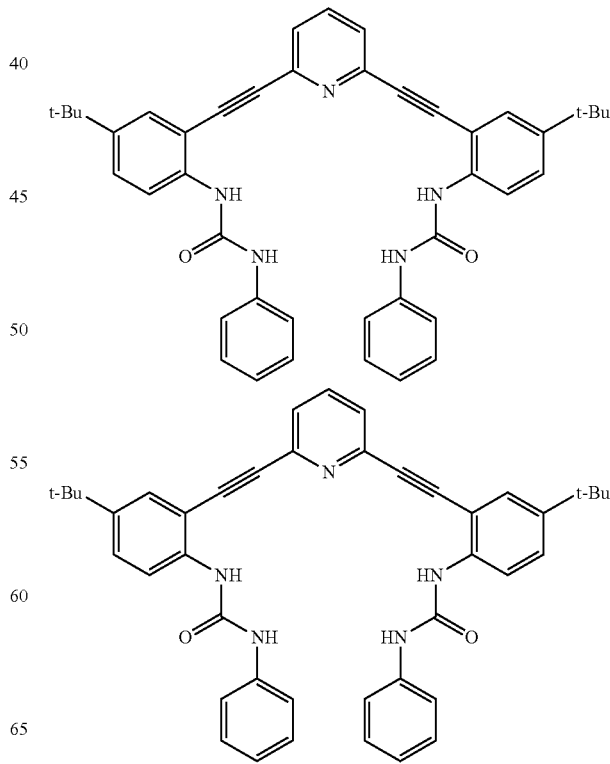

In one aspect, certain host compounds are represented by the formula

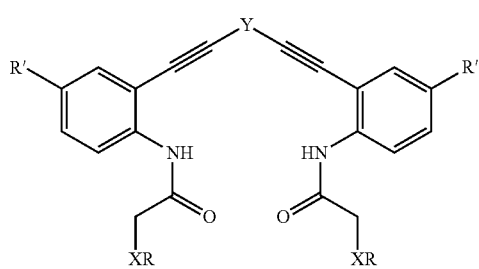

wherein X is O or S;

R is H, acyl, aralkyl or lower alkyl; and R' is H or lower alkyl, such as t-butyl. Examples of such compounds can be represented by the formula

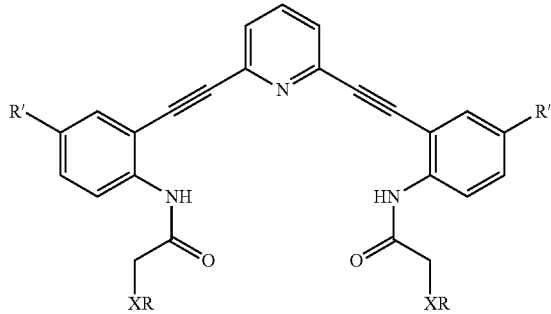

When X is O, the host compounds are particularly useful for binding oxophilic ions, such as calcium. Other host compounds having the formula above, wherein X is S have been designed to bind thiophilic metals. Examples of such compounds can be represented by the formula:

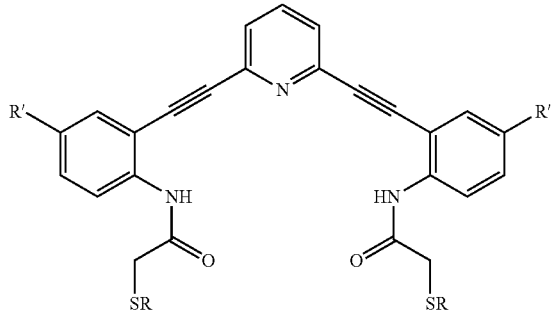

wherein R is H, acyl, aralkyl or lower alkyl; and R' is H, aliphatic, such as lower alkyl, aralkyl, aryl, sulfonyl, phosphonyl, phosphate, sulfate, —XC(O)OR$^6$ or —XC(O)NR$^7$R$^8$; wherein X is optional and if present is selected from the group consisting of —O—, —N(R$^9$)— or —S—; R$^6$ is selected from lower alkyl, aralkyl and aryl; and R$^7$, R$^8$ and R$^9$ independently are selected from H, lower alkyl, aralkyl and aryl. Particular examples of such compounds also can be represented by the formula

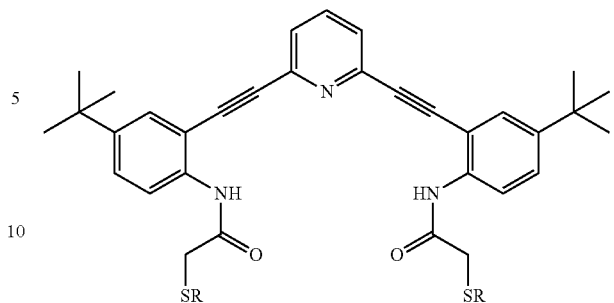

wherein R is H, acyl, aralkyl or lower alkyl.

Additional compounds useful for binding thiophilic metals include those of the formula

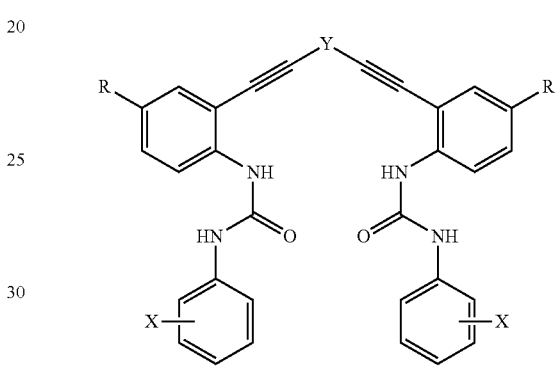

wherein X comprises an alkyl sulfide moiety.

In a further embodiment the host compounds and salts thereof have the formula

Formula II

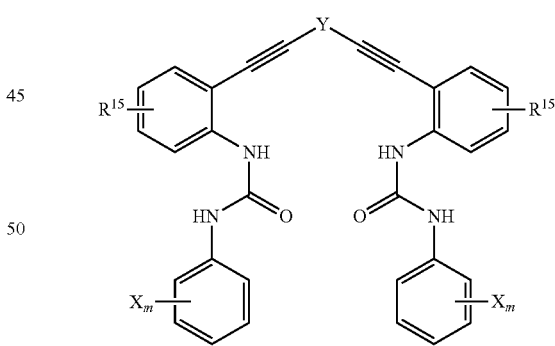

wherein Y represents an optionally substituted aromatic group as described above;

each R$^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

each X is independently halogen or a polyether moiety; and m is 1 to 5, provided that if X is halogen then m is 2 to 5.

In certain embodiments of Formula II, Y is:

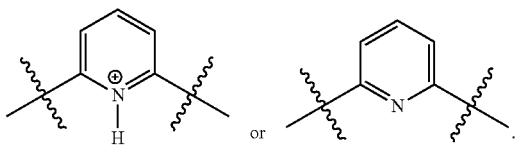 [SMILES: *c1cccc(*)[nH+]1 ; *c1cccc(*)n1]

In certain embodiments of Formula II, X is halogen, and m is 5. In certain embodiments of Formula II, X is polyether moiety as described above and m is 1. In certain embodiments of Formula II, $R^{15}$ is lower alkyl, substituted lower carboxyl, haloalkyl, or lower alkoxy, and $R^{15}$ is preferably in a para position relative to the position of the urea moiety (—NHC(O)NH—). In certain embodiments, X is a poly(ethylene oxide) moiety.

In a further embodiment the host compounds and salts thereof have the formula

Formula III

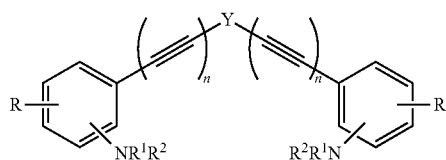

wherein Y is

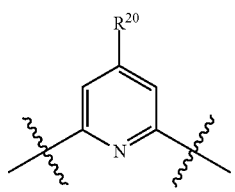

n is 1 or 2;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

$R^1$ is H, lower alkyl or aralkyl;

$R^2$ is selected from H, acyl, aralkyl, phosphonyl, —$SO_2R^3$; —$C(O)R^5$; —$C(O)OR^7$ or —$C(O)NR^9R^{10}$;

$R^3$; $R^5$; $R^7$; $R^9$ and $R^{10}$ independently are selected from H, lower alkyl, aralkyl or aryl; and $R^{20}$ is selected from alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

In certain embodiments of formula III, $R^{20}$ is lower alkyl, nitro, amino, or lower alkoxy. In certain embodiments of formula III, $R^1$ is H and $R^2$ is —$C(O)NR^9R^{10}$, or $R^1$ and $R^2$ are each H. In particular, $R^9$ is H and $R^{10}$ is an aryl, especially a substituted phenyl. The substituted phenyl may be substituted with a polyether moiety, a lower alkoxy, a lower alkyl, or at least one halogen. In certain embodiments of formula III, R is lower alkyl, substituted lower carboxyl, haloalkyl, or lower alkoxy, and R is preferably in a para position relative to the position of the —$NR^1R^2$ moiety.

Particular embodiments of formula III may have the formula

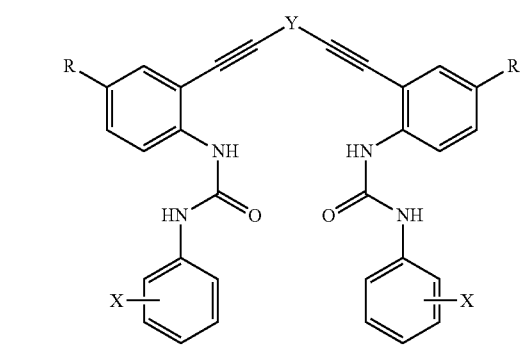

wherein Y is

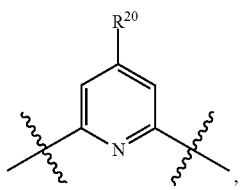

and

R is lower alkyl, substituted lower carboxyl, haloalkyl, or lower alkoxy; and X is alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

In another embodiment the host compounds and salts thereof have the formula

Formula IV

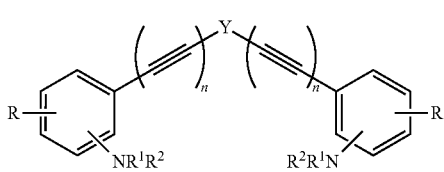

wherein Y is selected from

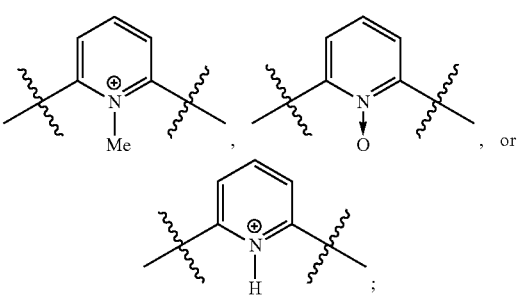

n is 1 or 2;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

$R^1$ is H, lower alkyl or aralkyl;

$R^2$ is selected from H, acyl, aralkyl, phosphonyl, $-SO_2R^3$; $-C(O)R^5$; $-C(O)OR^7$ or $-C(O)NR^9R^{10}$;

$R^3$; $R^5$; $R^7$; $R^9$ and $R^{10}$ independently are selected from H, lower alkyl, aralkyl or aryl.

In certain embodiments of formula IV, $R^1$ is H and $R^2$ is $-C(O)NR^9R^{10}$. In particular, $R^9$ is H and $R^{10}$ is an aryl, especially a substituted phenyl. The substituted phenyl may be substituted with a polyether moiety, a lower alkoxy, or a lower alkyl. In other embodiments of formula IV, $R^1$ is H and $R^2$ is $-SO_2R^3$, wherein $R^3$ is an aryl, especially a substituted phenyl. The substituted phenyl may be substituted with a polyether moiety, a lower alkoxy, a lower alkyl, or at least one halogen. In certain embodiments of formula IV, R is lower alkyl, substituted lower carboxyl, haloalkyl, or lower alkoxy, and R is preferably in a para position relative to the position of the $-NR^1R^2$ moiety.

Particular embodiments of formula IV may have the formula

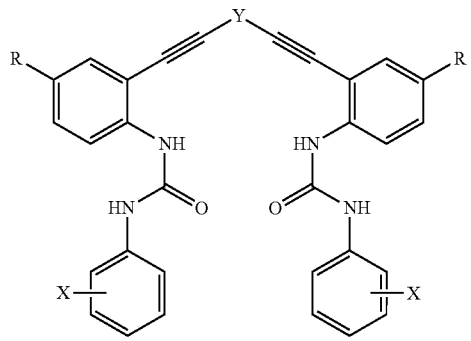

wherein Y is

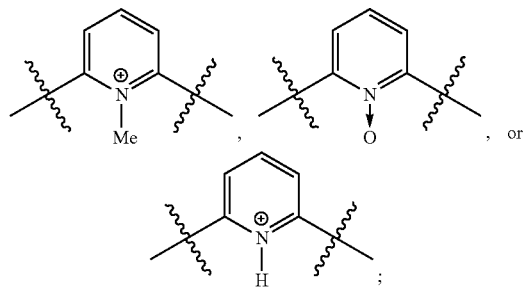

R is lower alkyl, substituted lower carboxyl, haloalkyl, or lower alkoxy; and X is alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

In a further embodiment the host compounds and salts thereof have the formula

Formula V

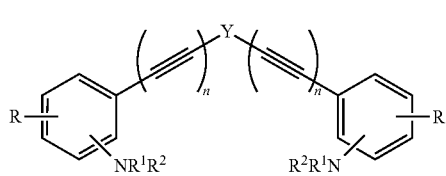

wherein Y represents an optionally substituted aromatic group as described above;

n is 1 or 2;

each R is independently H, a polyether moiety as described above, substituted carboxyl, alkoxy, or haloalkyl, provided that at least one R is not H, and that R is not methoxy or trifluoromethyl;

$R^1$ is H, lower alkyl or aralkyl;

$R^2$ is selected from H, acyl, aralkyl, phosphonyl, $-SO_2R^3$; $-C(O)R^5$; $-C(O)OR^7$ or $-C(O)NR^9R^{10}$;

$R^3$; $R^5$; $R^7$; $R^9$ and $R^{10}$ independently are selected from H, lower alkyl, aralkyl or aryl.

In certain embodiments of Formula V, Y is:

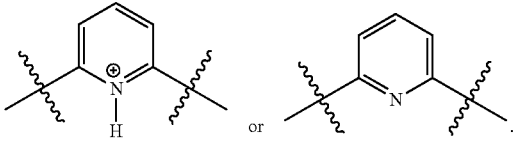 [SMILES: *c1cccc(*)[nH+]1 ; *c1cccc(*)n1]

In certain embodiments of Formula V, R is a substituted carboxyl such as $-COOR$ wherein R is a lower alkyl such as methyl, ethyl, or propyl. In certain embodiments of formula V, $R^1$ is H and $R^2$ is $-C(O)NR^9R^{10}$. In particular, $R^9$ is H and $R^{10}$ is an aryl, especially a substituted phenyl. The substituted phenyl may be substituted with a polyether moiety, a lower alkoxy, a lower alkyl, or at least one halogen. In certain embodiments of formula V, R is preferably in a para position relative to the position of the $-NR^1R^2$ moiety.

Particular embodiments of formula V may have the formula

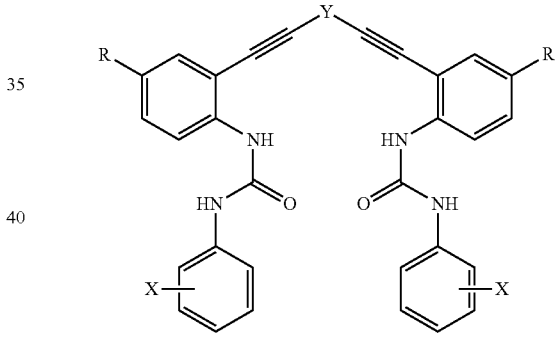

wherein X is alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

In an additional embodiment the host compounds and salts thereof have the formula Formula VI

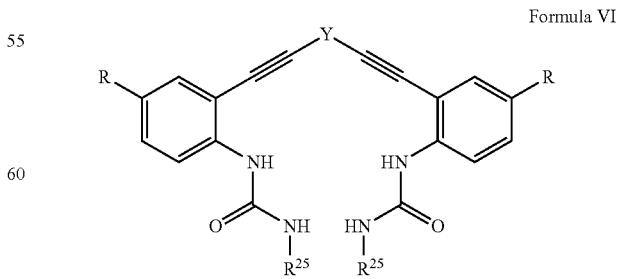

wherein Y represents an optionally substituted aromatic group as described above;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl; and each $R^{25}$ is independently —$CHR^{26}R^{27}$ or —$NR^{26}R^{27}$ wherein $R^{26}$ and $R^{27}$ are each independently selected from H, alkyl, substituted alkyl, aryl, or substituted aryl, provided that at least one of $R^{26}$ or $R^{27}$ is alkyl, substituted alkyl, aryl, or substituted aryl.

In certain embodiments of Formula VI, Y is:

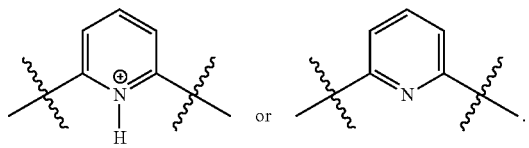 [SMILES: *c1cccc(*)[nH+]1 ; *c1cccc(*)n1]

In certain embodiments of formula VI, R is lower alkyl, substituted lower carboxyl, haloalkyl, or lower alkoxy. In certain embodiments of formula VI, $R^{26}$ is lower alkyl and $R^{27}$ is aryl or substituted aryl, particularly phenyl or substituted phenyl.

Also disclosed herein are methods for making the disclosed receptor compounds as well as intermediates for preparing the receptors. One type of versatile intermediate employed in the synthesis of exemplary receptor compounds disclosed herein is represented by the formula

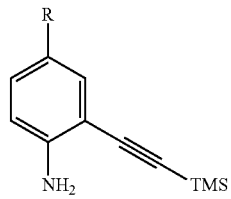

wherein R is H, lower alkyl, aralkyl or the like. Such compounds can be used to assemble (typically by an organometallic coupling reaction, such as a Sonogashira coupling) compounds of the formula

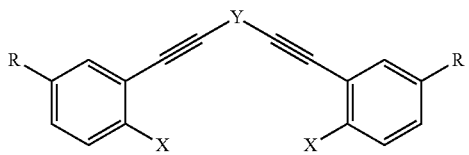

wherein X represents an aniline nitrogen, which optionally may be substituted. The aniline nitrogens can be converted into any one of many heteroatomic functional groups, including amides, sulfonamides, ureas, imines, and the like using standard synthetic techniques known to those of skill in the art of synthetic organic chemistry. The choice of group is dictated by several factors, including: optimizing guest interactions, changing the size of the binding cavity, preorganizing the binding cavity (by cyclization, for instance). Such factors are recognized and can be adjusted by those of skill in the art.

The disclosed host compounds are useful for binding and/or detecting ligands, in particular ionic ligands, including cationic and anionic ligands. The ligands may be inorganic or organic, but generally are inorganic. Typically, for binding anionic ligands, host compounds are protonated. Particular examples of anionic ligands bound and/or recognized by the disclosed host compounds include, without limitation sulfate, hydrogen sulfate, perchlorate or nitrate. Exemplary host compounds exhibit ligand binding selectivity or recognition. The host compounds may exhibit selectivity in binding of the ligand or reporting of a ligand's presence. For example, a spectral property of a host compound, such as fluorescence, may shift upon binding certain ligands, but not others. Examples of the disclosed host compounds have been designed to bind to salts containing particular metals, particularly toxic metals, including without limitation Pb, As, Zn, U, Ca, Cd and Hg.

It has been demonstrated for exemplary compounds disclosed herein that the spectral properties, such as the UV-Vis spectra shift noticeably upon binding of different guests. For example, the extended conjugation inherent in 2,6-bis(2-anilinoethynyl)pyridines derivatives produces distinct emission properties that will be used to monitor interactions with guest molecules. Exemplary compounds can distinguish between different anionic guests such as between Cl$^-$, which induces a shift in the UV-vis spectra of certain compounds, and Br$^-$, which does not induce such shifts. This discriminatory ability is most marked when the receptor is protonated. This indicates that these specific receptors can discriminate between different guests and are pH sensitive and can be tailored for use in solutions of specific acidity.

Certain embodiments are described below in connection with the following numbered paragraphs:

1. A compound, or a salt thereof, having the formula

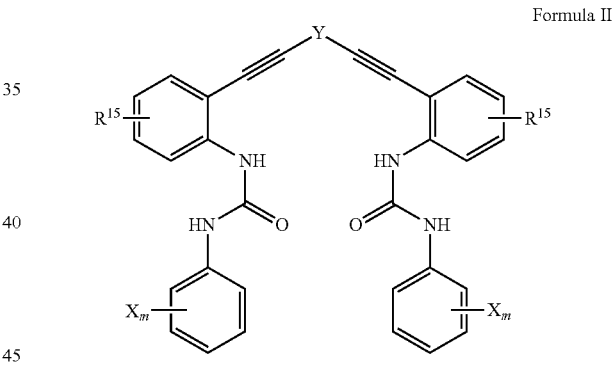

Formula II wherein Y represents an optionally substituted aromatic group;

each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

each X is independently halogen or a polyether moiety; and m is 1 to 5, provided that if X is halogen then m is 2 to 5.

2. A compound, or a salt thereof, having the formula

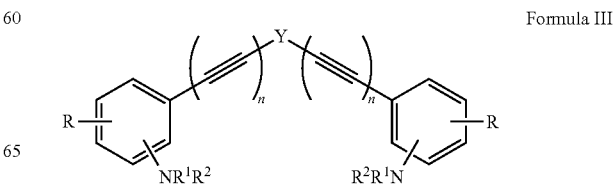

Formula III wherein Y is

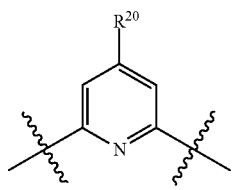

n is 1 or 2;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

$R^1$ is H, lower alkyl or aralkyl;

$R^2$ is selected from H, acyl, aralkyl, phosphonyl, $-SO_2R^3$; $-(R^4)C(O)R^5$; $-N(R^6)C(O)OR^7$ or $-N(R^8)C(O)NR^9R^{10}$;

$R^3$; $R^4$; $R^5$; $R^6$; $R^7$; $R^8R^9$ and $R^{10}$ independently are selected from H, lower alkyl, aralkyl or aryl; and $R^{20}$ is selected from alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

3. A compound, or a salt thereof, having the formula

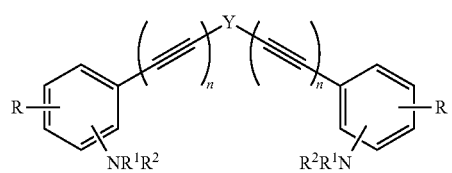

wherein Y is selected from

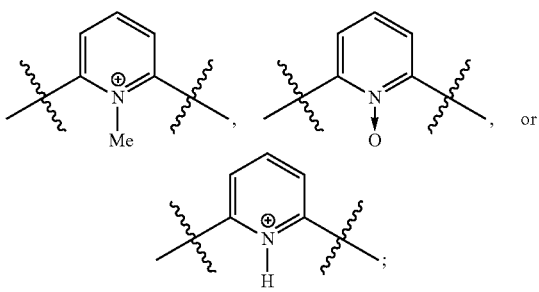

n is 1 or 2;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

$R^1$ is H, lower alkyl or aralkyl;

$R^2$ is selected from H, acyl, aralkyl, phosphonyl, $-SO_2R^3$; $-(R^4)C(O)R^5$; $-N(R^6)C(O)OR^7$ or $-N(R^8)C(O)NR^9R^{10}$;

$R^3$; $R^4$; $R^5$; $R^6$; $R^7$; $R^8R^9$ and $R^{10}$ independently are selected from H, lower alkyl, aralkyl or aryl.

4. A compound, or a salt thereof, having the formula

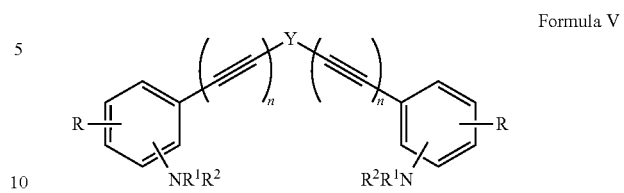

wherein Y represents an optionally substituted aromatic group;

n is 1 or 2;

each R is independently H, a polyether moiety, substituted carboxyl, alkoxy, or haloalkyl, provided that at least one R is not H, and that R is not methoxy or trifluoromethyl;

$R^1$ is H, lower alkyl or aralkyl;

$R^2$ is selected from H, acyl, aralkyl, phosphonyl, $-SO_2R^3$; $-(R^4)C(O)R^5$; $-N(R^6)C(O)OR^7$ or $-N(R^8)C(O)NR^9R^{10}$;

$R^3$; $R^4$; $R^5$; $R^6$; $R^7$; $R^8R^9$ and $R^{10}$ independently are selected from H, lower alkyl, aralkyl or aryl.

5. A host compound, or salt thereof, having the formula

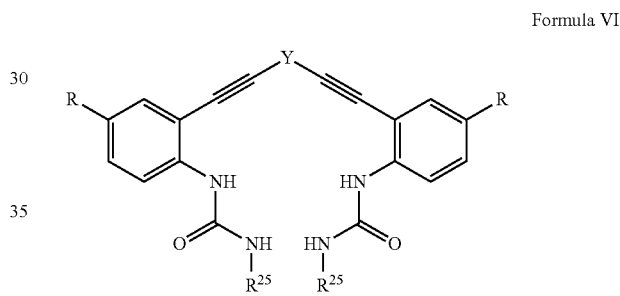

wherein Y represents an optionally substituted aromatic group;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl; and each $R^{25}$ is independently $-CHR^{26}R^{27}$ or $-NR^{26}R^{27}$ wherein $R^{26}$ and $R^{27}$ are each independently selected from H, alkyl, substituted alkyl, aryl, or substituted aryl, provided that at least one of $R^{26}$ or $R^{27}$ is alkyl, substituted alkyl, aryl, or substituted aryl.

6. The compound of any one of paragraphs 1, 4 or 5, wherein Y is

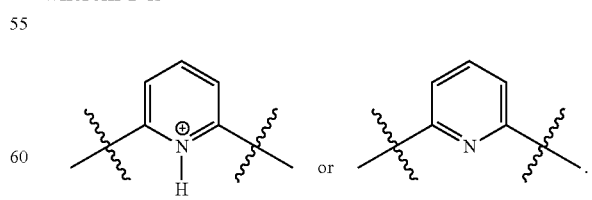

7. The compound of paragraph 1 or 6, wherein X is halogen and m is 5.

8. The compound of any one of paragraphs 2 to 4, wherein $R^1$ is H and $R^2$ is $-N(R^8)C(O)NR^9R^{10}$.

9. The compound of paragraph 8, wherein $R^8$ is H, $R^9$ is H, and $R^{10}$ is a substituted phenyl.

10. The compound of paragraph 2 or 3, wherein R is lower alkyl, substituted lower carboxyl, haloalkyl, or lower alkoxy, and R is in a para position relative to the position of the —$NR^1R^2$ moiety.

11. The compound of paragraph 4, wherein R is a polyether moiety or a substituted carboxyl.

12. The compound of paragraph 1 or 6, wherein the polyether moiety is a poly(ethylene oxide) moiety.

13. The compound of any one of paragraphs 2 to 4, wherein $R^1$ and $R^2$ are each H.

14. The compound of any one of paragraphs 2 to 4, wherein $R^1$ is H and $R^2$ is —$SO_2R^3$.

15. The compound of paragraph 9, wherein the substituted phenyl is substituted with a polyether moiety, a lower alkoxy, a lower alkyl, or at least one halogen.

16. The compound of paragraph 5 or 6, wherein $R^{26}$ is lower alkyl and $R^{27}$ is phenyl or substituted phenyl.

Reference will now be made in detail to the presently preferred embodiments of the disclosed compounds, compositions and methods.

EXAMPLES

The following examples are provided to illustrate certain particular features and/or embodiments. These examples should not be construed to limit the invention to the particular features or embodiments described.

Example 1

This example describes general materials and methods used in the synthesis and characterization of exemplary host compounds. All solvents were dried over 3 Å molecular sieves unless otherwise stated. THF, $Et_3N$, and $CH_2Cl_2$ were respectively distilled from potassium metal and $CaH_2$ prior to use. All other materials were obtained from TCI-America, Sigma-Aldrich, Acros and Strem and used as received. $^1H$ and $^{13}C$ NMR spectra were recorded using a Varian Inova 300 ($^1H$ 299.95 MHz, $^{13}C$ 75.43 MHz) or Inova 500 ($^1H$ 500.10 MHz, $^{13}C$ 125.75 MHz) spectrometer. Chemical shifts (δ) expressed as ppm downfield from tetramethylsilane using either the residual solvent peak as an internal standard ($CDCl_3$, $^1H$, 7.27 ppm) or using $CDCl_3$ spiked with 1% trimethylsilane for the $^1H$ NMR spectra. For the $^{13}C$ NMR spectra the middle $CDCl_3$ peak (δ 77.00 ppm) was used as the internal standard. Signal patterns are indicated as b, broad; s, singlet; d, doublet; t, triplet; m, multiplet. Coupling constants (J) are given in hertz. UV-Vis spectra were recorded using a Hewlett-Packard 8453 spectrophotometer and extinction coefficients are expressed in $M^{-1} cm^{-1}$. Mass spectra were recorded using an Agilent 1100 Series LC/MSD. Emission spectra were recorded on a Hitachi F-4500 fluorescence spectrophotometer. Melting points were determined with a Meltemp II apparatus or a TA Instruments DSC 2920 Modulated DSC. Column chromatography was performed on Whatman reagent grade silica gel (230-400 mesh). Rotary chromatography was performed on a Harrison Research Chromatotron model 7924T with EM-Science 60PF$_{254}$ silica gel. Precoated silica gel plates (Sorbent Technology, UV$_{254}$, 200 μm, 5×20 cm) were used for analytical thin-layer chromatography.

General Sulfonamide Synthesis:

A general synthesis of sulfonamides followed the scheme:

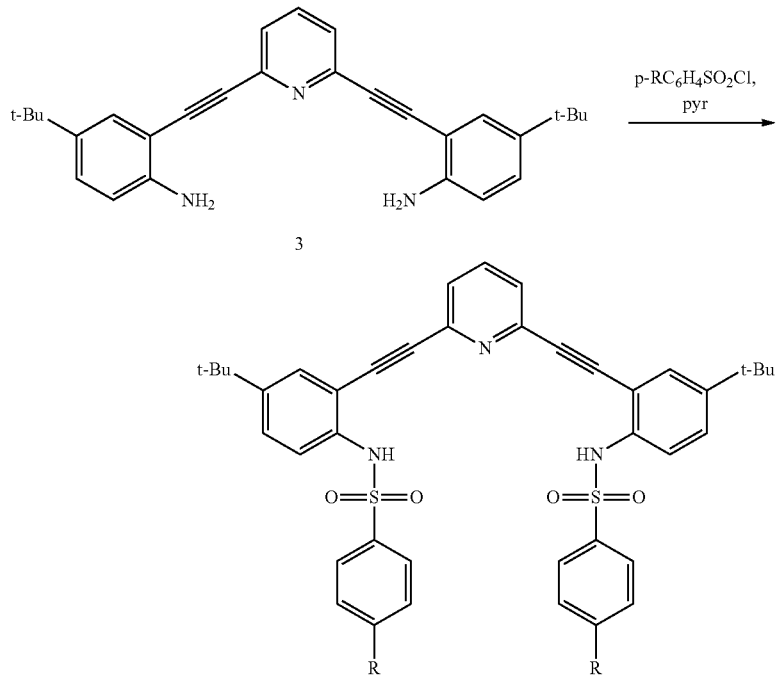

A solution of arene 3 (1 equiv) and sulfonyl chloride (5 equiv) in pyridine (8-15 mM) was stirred for 3 hours under an $N_2$ environment. Following concentration in vacuo, the crude oil was filtered through a 2.5 cm silica plug and then chromatographed on silica gel.

The synthesis of several exemplary sulfonamides by the general method is illustrated by the scheme:

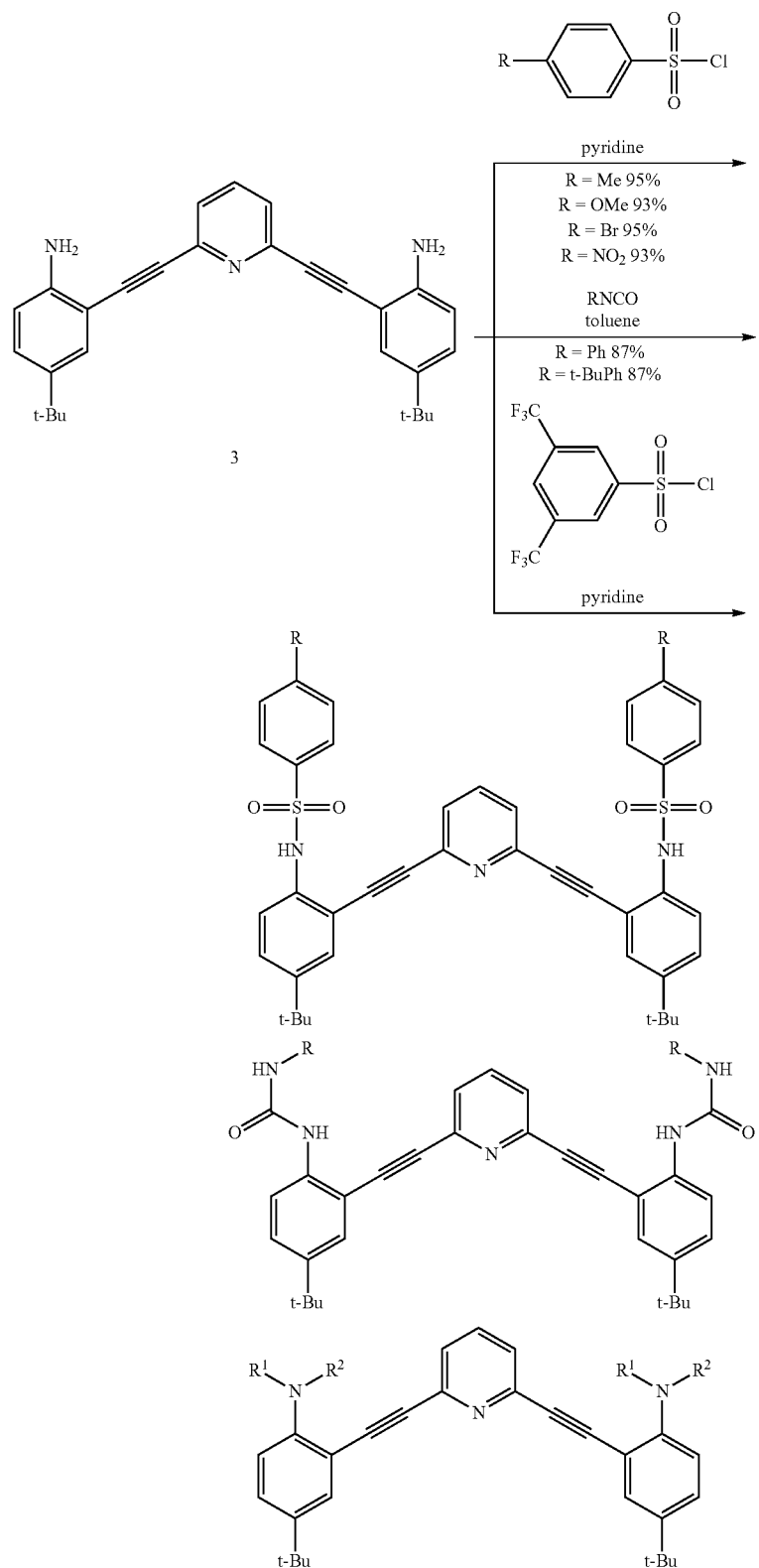

General Salt Preparation:

A 10 mM stock solution of sulfonamide receptor dissolved in $CDCl_3$ with 1% TMS that had been passed through basic alumina and stored over 3 Å molecular sieves was prepared. With a 9 inch pipet and 10 ml pipet bulb HCl gas is passed through the sulfonamide solution 20 times. The resulting bright yellow solution is diluted to the original volume and an appropriate aliquot is removed for study.

Crystal Growth Conditions:

Sulfonamide receptors were dissolved in a 10×75 mm test tube with EtOAc to a concentration >10 mM (for halide salts HX gas was passed through the EtOAc solution of receptor). Alternatively, 1 drop of concentrated HX is added and the resulting yellow solution is thoroughly mixed). Hexanes cooled to 0° C. were layered on top of receptor solutions and set aside. After 3 days colorless (neutral receptor complex) or yellow (protonated receptor complex) single crystals were harvested for X-ray diffraction studies.

Single Crystal X-Ray Diffraction:

X-Ray diffraction data for $(1.H_2O)_2$, $(2.H_2O)_2$, $(H2^+.Cl^-)_2$, $(H1^+Cl^-).(1.H_2O)$ and $(H1^+.Br^-)_2$ were collected on a Bruker SMART APEX diffractometer using $MoK_\alpha$, radiation ($\lambda=0.7107$ Å). Data were corrected for absorption using the SADABS v2.02 area-detector absorption correction program. The structures were solved by direct methods and refined based on $|F|^2$. All non-hydrogen atoms were refined with anisotropic displacement parameters. Hydrogen atoms in the investigated structures were found from the residual density maps and refined with isotropic thermal parameters except those in terminal t-Bu groups in $(H2^+.Cl^-)_2$, $(H1^+Cl^-).(1.H_2O)$ and $(H1^+.Br^-)_2$, which were placed in calculated positions and refined in a rigid group model with isotropic thermal parameters U(H)=1.5 Ueq (C). One of the H atoms at the bridging solvent molecule in $(1.H_2O)_2$ is disordered over two positions in a 1:1 ratio. The O atoms of the bridging water molecule and the Cl atom in $(H1^+.Cl^-).(1.H_2O)$ are disordered over two positions corresponding to opposite orientations of the dimeric units. These O and Cl atoms were refined in the same positions with occupation factors $\mu=\frac{1}{2}$. The H atoms attached to the O atom in the bridging water molecules were not found from the F-map. All calculations were performed with the SHELXTL v.6.1 program package.

Example 2

This example describes the synthesis of sulfonamide compound 1 via the general synthesis set forth above.

Compound 1

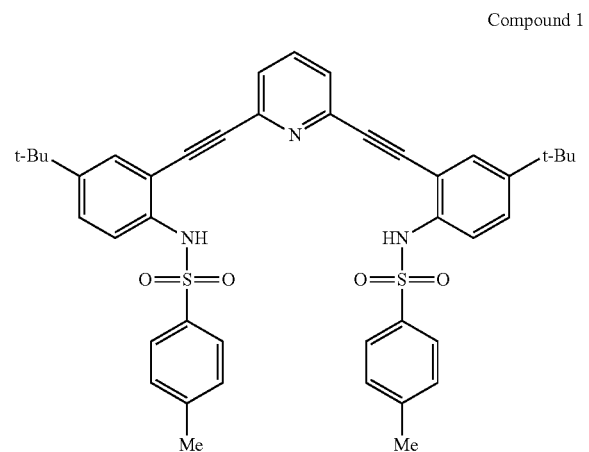 [SMILES: Cc1ccc(S(=O)(=O)Nc2ccc(C(C)(C)C)cc2C#Cc2cccc(C#Cc3cc(C(C)(C)C)ccc3NS(=O)(=O)c3ccc(C)cc3)n2)cc1]

Arene 3 (150 mg, 0.36 mmol) was reacted with p-toluenesulfonyl chloride according to General Preparation for Sulfonamides (above). Purification by chromatography (1:1 hexanes:EtOAc) afforded $(1.H_2O)_2$ (249 mg, 95%) as a pale yellow solid. Recrystallization by diffusion (hexanes:EtOAc) afforded colorless crystals. Mp: 133-135° C. $^1$H NMR (300 MHz, $CDCl_3$): δ 7.85-7.71 (m, 5H), 7.52-7.43 (m, 6H), 7.35 (dd, J=8.5, 2.3 Hz, 2H), 7.15 (d, J=8.5 Hz, 4H), 2.34 (s, 6H), 1.26 (s, 18H). $^{13}$C NMR (75 MHz, $CDCl_3$): δ 147.53, 143.73, 142.85, 136.93, 136.49, 135.84, 129.54 (2C), 127.89, 127.25, 126.29, 120.52, 112.89, 93.20, 85.56, 34.29, 31.03, 21.45. UV-Vis ($CH_2Cl_2$): $\lambda_{max}$ (ε) 234 (58,000), 287 (31,000), 330 (27,600) nm. Fluorescent emission ($[(1.H_2O)_2]\leq0.057$ mM in $CHCl_3$; 354 nm excitation): $\lambda_{max}$ 388 nm. IR (neat): ν 3266, 2961, 2899, 2877, 2213, 1555, 1156 $cm^{-1}$. MS (CI pos) m/z (%): 732 ($M^+$+2, 21), 731 ($MH^+$, 56), 730 ($M^+$, 100); $C_{43}H_{43}N_3O_4S_2$ (729.95).

Example 3

This example describes the synthesis of sulfonamide compound 2 via the general synthesis set forth above.

Compound 2

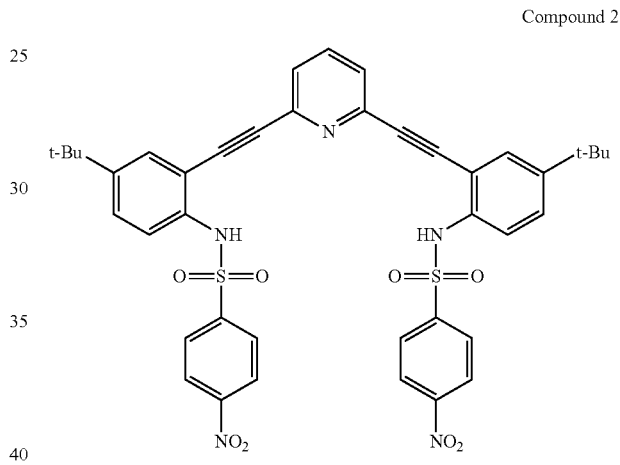

Arene 3 (150 mg, 0.36 mmol) was reacted with p-nitrobenzenesulfonyl chloride according to General Preparation for Sulfonamides (above). Purification by chromatography (20:1 $CH_2Cl_2$:EtOAc) afforded $(2.H_2O)_2$ (285 mg, 93%) as a pale yellow solid. Recrystallization by diffusion (pentane:$CHCl_3$ or hexanes:EtOAc) afforded pale yellow crystals. Mp: 136-139° C. $^1$H NMR (300 MHz, $CDCl_3$): δ 8.15 (d, J=8.7 Hz, 4H), 8.03 (d, J=8.7 Hz, 4H), 7.74 (t, J=7.8 Hz, 1H), 7.55 (d, J=8.7 Hz, 2H), 7.48-7.37 (m, 6H), 1.29 (s, 18H). $^{13}$C NMR (75 MHz, $CDCl_3$): δ 150.10, 149.33, 145.32, 142.68, 137.20, 134.63, 129.82, 128.68, 128.28, 126.31, 124.12, 123.31, 114.59, 92.68, 85.71, 34.51, 31.05. UV-Vis ($CH_2Cl_2$): $\lambda_{max}$ (ε) 242 (56,200), 285 (35,500), 319 (23,000) nm. Fluorescent emission ($[(2.H_2O)_2]\leq0.057$ mM in $CHCl_3$; 364 nm excitation): $\lambda_{max}$ 428 nm. IR (neat): ν 3271, 2964, 2869, 2213, 1348, 1171 $cm^{-1}$. MS (CI pos) m/z (%): 794 ($M^+$+2, 24), 793 ($MH^+$, 53), 792 ($M^+$, 100), 608 (17), 607 (44); $C_{41}H_{37}N_5O_8S_2$ (791.89).

Example 4

This example describes the synthesis of the para-methoxy analog of compounds 1 and 2. Arene 3 (110 mg, 0.26 mmol) was reacted with p-methoxybenzenesulfonyl chloride according to General Preparation for Sulfonamides (above). Purification by chromatography (20:1 $CH_2Cl_2$:EtOAc)

afforded (pMeO.H$_2$O)$_2$ (185 mg, 93%) as a white crystalline solid. Recrystallization by diffusion (hexanes:CH$_2$Cl$_2$) afforded colorless crystals. Mp: 141-143° C. $^1$H NMR (300 MHz, CDCl$_3$): δ 7.77 (d, J=9 Hz, 4H), 7.76 (t, J=9 Hz, 1H), 7.53-7.45 (m, 5H), 7.37 (dd, J=9, 3 Hz, 2H), 6.84 (d, J=9 Hz, 4H), 3.77 (s, 6H), 1.28 (s, 18H). $^{13}$C NMR (75 MHz, CDCl$_3$): δ 163.06, 147.62, 142.93, 136.75, 135.70, 130.85, 129.60, 129.43, 127.85, 126.44, 120.64, 114.09, 113.02, 93.28, 85.33, 55.45, 34.31, 31.03. UV-Vis (CH$_2$Cl$_2$): $\lambda_{max}$ (ε) 239 (71,700), 292 (30,200), 343 (23,000) nm. Fluorescent emission ([(pMeO.H$_2$O)$_2$]≤0.05 mM in CHCl$_3$; 353 nm excitation): $\lambda_{max}$ 389 nm. IR (neat): ν 3248, 2962, 2902, 2870, 2214, 1498, 1161 cm$^{-1}$. MS (CI pos) m/z (%): 764 (M$^+$+2, 22), 763 (MH$^+$, 49), 762 (M$^+$, 100); C$_{43}$H$_{43}$N$_3$O$_6$S$_2$ (761.95).

Example 5

This example describes the characterization of the solid state and solution phase ion binding properties of exemplary host molecules disclosed herein. Colorless single crystals of compounds 1 and 2 suitable for X-ray diffraction were grown by layering hexane onto ethyl acetate solutions of each receptor. As suggested from the $^1$H NMR spectroscopic data, complexes (1.H$_2$O)$_2$ and (2.H$_2$O)$_2$ both crystallize as dimers in space group P-1 with two receptor molecules and two water molecules per unit cell; consequently, each dimer has crystallographic inversion symmetry. A prominent feature of each crystal structure is the presence of two hydrogen bonding water molecules stitching the receptor dimers together. Both pyridine nitrogens accept hydrogen bonds from a different water molecule [2.797(4)-2.804(2) Å, O—H•••N angles 172 (4)-175(3)°], while one water-water hydrogen bond is present [2.917(5)-3.006(7) Å, O—H•••O angles 164(4)-178(6)°]. All of the N-substituted sulfonamides adopt the energetically most-favored 'staggered' conformation, and both sulfonamide protons on each receptor donate a hydrogen bond to a different water molecule [2.855(4)-2.860(3) Å, 157(2)-164 (3)° and 3.028(4)-3.039(3) Å, 158(2)-164(3)°] such that the 2+2 dimer structure is held together by four sulfonamide-water hydrogen bonds, two pyridine-water hydrogen bonds, one water-water hydrogen bond and two π-stacking interactions between receptors ranging from 3.42-3.44 Å.

The dimerization of receptor 1 was further investigated in CDCl$_3$ solutions. Receptor 1 was dissolved in water-saturated CDCl$_3$ to a concentration of 197 mM. Monitoring the sulfonamide N—H and water $^1$H NMR resonances following a series of dilutions resulted in data that could be fit to a 1:1 dimerization with the non-linear regression curve fitting software WinEQNMR. In CDCl$_3$ solutions receptor 1 is shown to dimerize with a modest K$_{dim}$=42 M$^{-1}$. Supporting evidence of dimerization in CDCl$_3$ solutions resulted from the NOE observed between the protons on the guest water molecules and the sulfonamide protons of the receptor. Receptor 1 exhibits a propensity to crystallize as a dimer with H$_2$O even in the presence of other potential neutral guest molecules and in solvents dried over 3 Å molecular sieves.

Receptor molecules 1 and 2 both alter guest selectivity by simple changes in the protonation state of the receptors. By protonating the pyridine nitrogen of receptors 1 and 2, the anion binding capacity of these receptors is activated. The halide binding properties of H1$^+$ have been investigated in the solid state: single crystals of the chloride and bromide complexes are prepared by dissolving receptor 1 or 2 in ethyl acetate and bubbling HCl or HBr gas through the solution. Crystallization is induced by layering hexanes onto the yellow ethyl acetate solutions. Strikingly, the single crystal structures of the H2$^+$.Cl$^-$ and H1$^+$.Br$^-$ complexes revealed nearly isostructural dimers to those observed for the neutral (1.H$_2$O)$_2$ and (2.H$_2$O)$_2$ water dimers. In the solid state the (H2$^+$.Cl$^-$)$_2$ and (H1$^+$.Br$^-$)$_2$ dimers (FIG. 2) are held together by four sulfonamide hydrogen bonds [3.156(2)-3.229(2) Å, N—H•••Cl angles 151(2)-171(3)°; 3.338(5)-3.440(6) Å, N—H•••Br angles 136(4)-168(4)°], two pyridinium N—H hydrogen bonds to the anions [3.022(2) Å, 175(3)° for (H2$^+$.Cl$^-$)$_2$ and 3.127(6) Å, 173(4)° for (H1$^+$.Br$^-$)$_2$], two C$_{aryl}$—H•••X hydrogen bonds (3.69-3.90 Å), and two π-stacking interactions between receptors (3.49 Å for (H2$^+$.Cl$^-$)$_2$ and 3.61 Å for (H1$^+$.Br$^-$)$_2$. The numerous hydrogen bonds and unique dimerization bring the negatively charged halides into close proximity with halide-halide distances of 3.92 Å for (H2$^+$.Cl$^-$)$_2$ and 4.08 Å for (H1$^+$.Br$^-$)$_2$.

CAChe semi-empirical calculations of the 2,6-bis(2-anilino-ethynyl)pyridine receptors suggested that larger polyatomic anions would not fit within the binding pocket of the receptor. As predicted, the single crystal X-ray structure of the HBF$_4$ salt (H1$^+$.BF$_4^-$) reveals that the binding pocket is too small to accommodate the interaction of the large BF$_4^-$ guest with either sulfonamide proton. Dilution experiments of H1$^+$.BF$_4^-$ revealed minimal change in the $^1$H NMR spectrum upon addition with CDCl$_3$, indicating negligible dimerization in solution as predicted by the receptor conformation observed in the crystal structure. However, titrations of H1$^+$.BF$_4^-$ with tetra-n-butylammonium halide salts do indicate anion binding occurs in solution between the receptor and halides. Furthermore, the concentration dependence observed in the $^1$H NMR spectrum upon dilution of (H1$^+$—Cl$^-$)$_2$ in CDCl$_3$ indicates the presence of a receptor/halide dimer in solution. A supersaturated solution of (H1$^+$—Cl$^-$)$_2$ (60 mM) was obtained by passing HCl gas through a CDCl$_3$ solution of neutral receptor 1. Plotting the changes in chemical shift upon dilution and subsequent fitting of this data to a 1:1 dimerization model with the non-linear least squares regression program WinEQNMR resulted in a K$_{dim}$=250 M$^{-1}$ in CDCl$_3$.

Further evidence of dimerization was obtained by mixing a 1:1 ratio of receptor 1 and a p-methoxyphenyl sulfonamide derivative (synthesis described in Example 4 above). In an equimolar mixture of the two receptors, the resulting $^1$H NMR signals are shifted from the signals observed for either of the analogous homodimers prepared in the same way at the same concentration. Briefly, the equimolar mixtures of these receptors were prepared at 10 mM in CDCl$_3$ as follows: [1H$_2$O].[PMeO.H$_2$O]. 1H$_2$O (3.650 mg, 0.00488 mmol) and pMeO.H$_2$O (3.740 mg, 0.00480 mmol) were dissolved in separate portions of CDCl$_3$ with 1% TMS (1 mL) passed through basic alumina and dried with 3 Å molecular sieves. Aliquots (400 μL) from each solution were transferred to an NMR tube via syringe and thoroughly mixed. $^1$H NMR spectra were recorded on a Varian 300 MHz spectrometer. Proton signals were referenced to the 1% TMS included in the CDCl$_3$. $^1$H NMR (300 MHz, CDCl$_3$): δ 7.81-7.73 (m, 10H), 7.52-7.44 (m, 12H), 7.38-7.33 (m, 8H), 7.18 (d, J=9 Hz, 4H), 6.85 (d, J=9 Hz, 6H), 7.18 (d, J=6 Hz, 3H) 2.29 (s, 6H), 1.26 (s, 18H).

By comparison, 10 mM stock solutions of (H1$^+$.Cl$^-$)$_2$ had the data: $^1$H NMR (300 MHz, CDCl$_3$): δ 9.51 (b, 2H), 8.40 (b, 1H), 8.13 (d, J=6 Hz, 4H), 8.00-7.75 (b, 4H), 7.48-7.41 (m, 6H), 7.18 (d, J=6 Hz, 3H) 2.29 (s, 6H), 1.26 (s, 18H). 10 mM stock solutions of (HpMeO$^+$.Cl$^-$)$_2$ had the data: $^1$H NMR (300 MHz, CDCl$_3$): δ 9.36 (b, 2H), 8.31 (t, 1H), 8.17 (d, J=9 Hz, 4H), 7.72 (d, J=9 Hz, 4H), 7.40 (m, 6H), 6.86 (d, J=9 Hz, 4H) 3.75 (s, 6H), 1.26 (s, 18H).

This result suggests that both homodimers and a third species—the heterodimer—are present in solution, but equilibrating quickly on the NMR timescale. From all of these experiments it is evident that dimerization of both the neutral and protonated forms of 2,6-bis(2-anilinoethynyl)pyridine receptors occurs both in the solid state and in solution.

Remarkably, a different type of "heterodimer" (H1$^+$.Cl$^-$). (1.H$_2$O) was also crystallized in the presence of concentrated HCl with one water and one chloride in the binding pocket. Briefly, the heterodimer [H1$^+$.Cl$^-$].[HpMeO$^+$.Cl$^-$] was prepared as follows: The stock solutions from the preparation of [1.H$_2$O].[pMeO.H$_2$O] (above) were combined and protonated with HCl gas (see above, General salt preparation). $^1$H NMR spectra were recorded on a Varian 300 MHz spectrometer. Proton signals were referenced to the 1% TMS included in the CDCl$_3$. $^1$H NMR (300 MHz, CDCl$_3$): δ 9.49 (s, 2H), 9.44 (s, 2H), 8.30 (b, 2H), 8.18 (d, J=9 Hz, 4H), 8.12 (d, J=9 Hz, 4H), 7.71 (d, J=6 Hz, 4H) 7.46 (m, 12H), 7.17 (d, J=6 Hz, 4H), 6.85 (d, J=6 Hz, 4H), 3.73 (s, 6H), 2.27 (s, 6H), 1.25 (s, 36H). The resultant heterodimer contains one protonated receptor that binds a chloride anion while the other receptor in the dimer is neutral and bound to a water molecule. Water and chloride are freely exchangeable in this binding pocket and provide intermediate structural features to the H$_2$O and halide dimers. Analogous to the other dimers presented, the heterodimer is stabilized by π-stacking interactions between the two receptors (3.43 Å) and a series of seven guest assisted hydrogen bonds. Each guest molecule—water and chloride—accepts two sulfonamide N—H hydrogen bonds (3.157(3)-3.181(3) Å, N—H•••X angles 158(3)-167(3)° and additionally forms a helical hydrogen bonding pattern running between the pyridinium, chloride, water and pyridine heteroatoms (2.926(3)-3.10 Å, 164(3)-176(4)°. Two C$_{aryl}$—H.Cl hydrogen bonds (3.76-3.93 Å) also stabilize the dimer.

Example 6

This example describes the synthesis of the compound

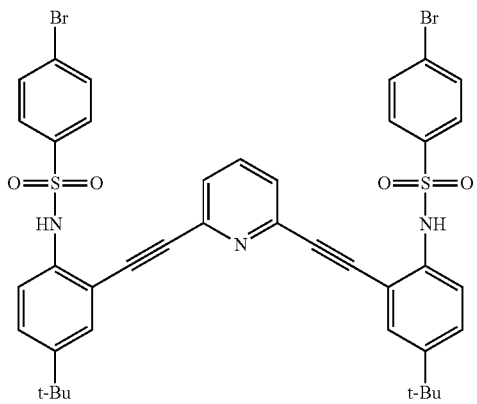 [SMILES: CC(C)(C)c1ccc(NS(=O)(=O)c2ccc(Br)cc2)c(C#Cc2cccc(C#Cc3cc(C(C)(C)C)ccc3NS(=O)(=O)c3ccc(Br)cc3)n2)c1]

via the General Preparation for Sulfonamides described above. Briefly, arene 3 (100 mg, 0.24 mmol) was reacted with p-bromobenzenesulfonyl chloride. Purification by chromatography (2.5:1 hexanes:EtOAc) followed by recrystallization by diffusion (hexanes:EtOAc) afforded 10c (183 mg, 89%) as colorless crystals. Mp: 152-154° C. $^1$H NMR (300 MHz, CDCl$_3$): δ 8.00 (br s, 2H), 7.82-7.71 (m, 5H), 7.53-7.37 (m, 10H), 1.29 (s, 18H). $^{13}$C NMR (75 MHz, CDCl$_3$): δ 148.25, 142.72, 138.65, 137.16, 135.52, 132.22, 129.59, 128.88, 128.18, 127.96, 126.19, 121.56, 113.46, 92.97, 85.89, 34.43, 31.08. Fluorescence emission ([10c]≤5.7×10$^{-5}$ M in CHCl$_3$; 308 nm excitation): λ$_{max}$ 381 nm. MS (CI pos) m/z (%): 863 (M$^+$+6, 24), 862 (M$^+$+5, 61), 861 (M$^+$+4, 42), 860 (M$^+$+3, 100), 859 (M$^+$+2, 21), 858 (MH$^+$); C$_{41}$H$_{37}$Br$_2$N$_3$O$_4$S$_2$ (857.06).

Example 7

This example describes the synthesis of the compound

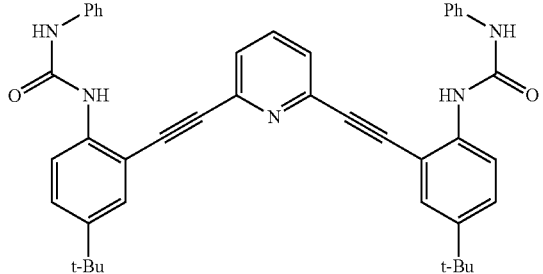 [SMILES: CC(C)(C)c1ccc(NC(=O)Nc2ccccc2)c(C#Cc2cccc(C#Cc3cc(C(C)(C)C)ccc3NC(=O)Nc3ccccc3)n2)c1]

Phenyl isocyanate (303 mg, 2.5 mmol) was added to a solution of arene 3 (215 mg, 0.5 mmol) in toluene (25 mL). The reaction was stirred for 12 hours under an N$_2$ environment. Concentration in vacuo afforded a crude oil which was filtered through a 2.5 cm silica plug with 1:1 hexanes:EtOAc. Chromatography on silica gel (3:1 hexanes:EtOAc) followed by precipitation with hexanes or ether afforded the desired product (287 mg, 87%) as a white, fluffy solid. Recrystallization by diffusion (pentane:CHCl$_3$) afforded white, needle crystals. Mp: 212-215° C. $^1$H NMR (300 MHz, CDCl$_3$): δ 8.32 (br s, 2H), 8.07 (d, J=4.8 Hz, 2H), 7.74 (br s, 2H), 7.47-7.28 (m, 11H), 7.15 (t, J=4.5 Hz, 4H), 6.92 (t, J=4.5 Hz, 2H), 1.29 (s, 18H). $^{13}$C NMR (125 MHz, THF-d$_8$): δ 152.95, 145.38, 144.62, 141.17, 140.40, 138.15, 130.11, 129.56, 128.78, 127.65, 122.94, 120.33, 114.49, 110.45, 94.38, 87.33, 35.01, 31.75. Fluorescence emission ([11a]≤5.7×10$^{-5}$ M in CHCl$_3$; 371 nm excitation): λ$_{max}$ 411 nm. MS (CI pos) m/z (%): 661 (MH$^+$, 49), 660 (M$^+$, 100); C$_{43}$H$_{41}$N$_5$O$_2$ (659.82).

Example 8

This example describes the synthesis of the compound

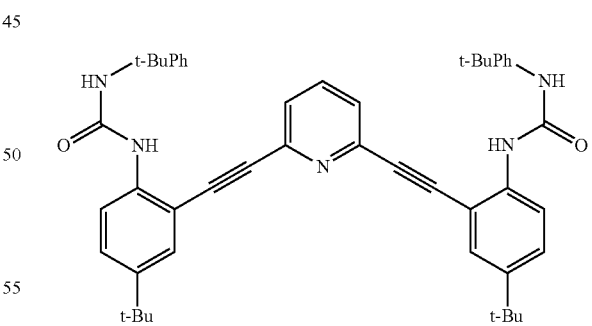

4-(t-Butyl)phenyl isocyanate (124 mg, 0.72 mmol) was added to a solution of arene 3 (100 mg, 0.24 mmol) in toluene (10 mL). The reaction was stirred for 12 hours under an N$_2$ environment. Concentration in vacuo followed by chromatography on silica gel (CHCl$_3$) and trituration with acetone or ether afforded 11b (135 mg, 75%) as a white, fluffy solid. Mp: 197-200° C. $^1$H NMR (300 MHz, CDCl$_3$): δ 8.33 (br s, 2H), 8.05 (d, J=8.7 Hz, 2H), 7.66 (s, 2H), 7.38-7.15 (m, 15H), 1.28 (s, 18H), 1.23 (s, 18H). MS (CI pos) m/z (%): 774 (MH$^+$+1, 13), 773 (MH$^+$, 66), 772 (M$^+$, 100); C$_{51}$H$_{57}$N$_5$O$_2$ (772.03).

Example 9
This example describes the synthesis of thiol-based receptors via the scheme:
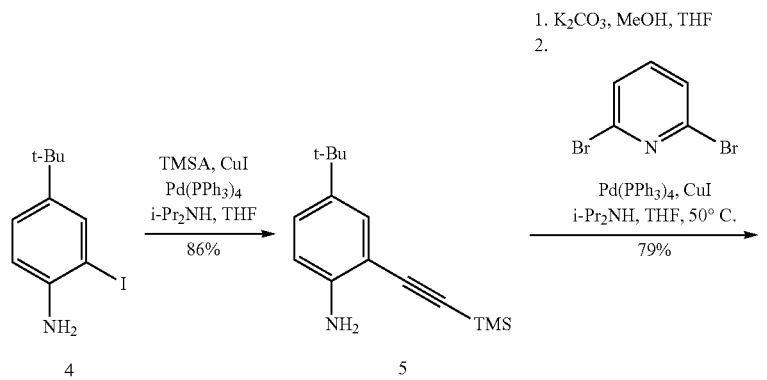
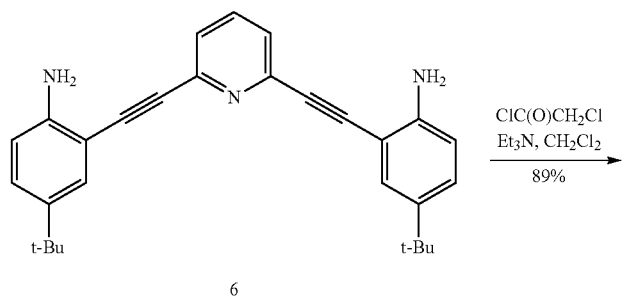
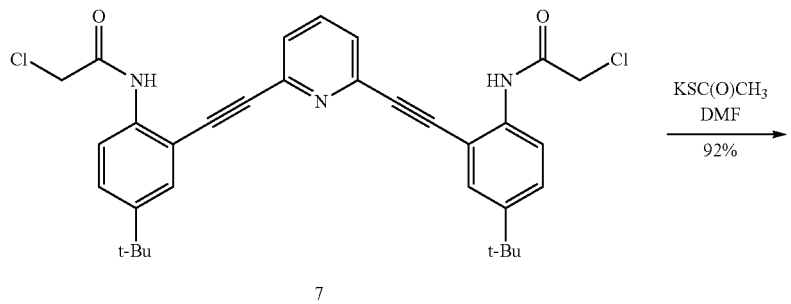
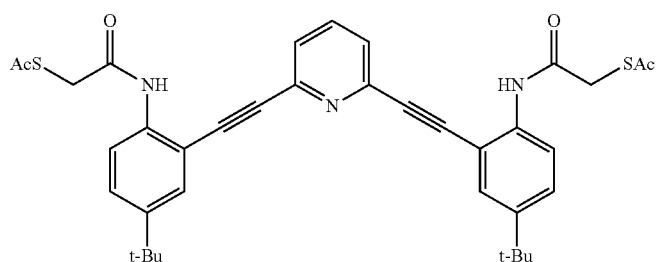

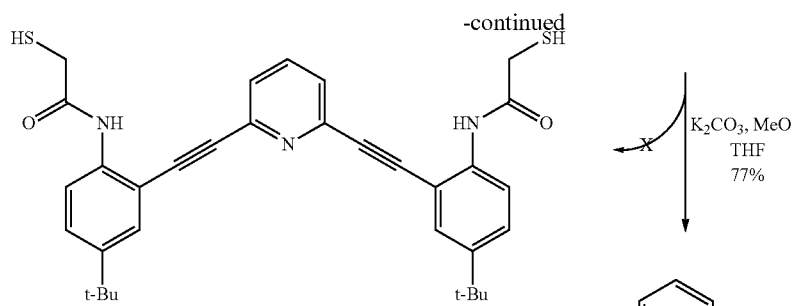

9

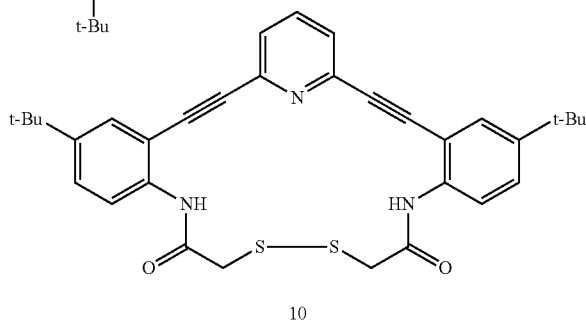

10

With continued reference to the scheme above, synthesis began with previously reported iodoaniline 4, (Wan, W. B.; Haley, M. M. *J. Org. Chem.* 2001, 66, 3893-3901) available in 73% yield via iodination of tert-butylaniline. Pd-catalyzed cross-coupling (*Metal-Catalyzed Cross-Coupling Reactions*, 2nd ed.; de Meijere, A., Diederich, F., Eds.; Wiley-VCH: Weinheim, 2004) of 4 with TMSA afforded ethynylarene 5 in 86% yield. Arene 6 was obtained in 79% yield by desilylation of 5 with weak base (*Protecting Groups in Organic Synthesis*, 3rd ed.; Greene, T. W.; Wuts, P. G. M., Eds.; Wiley-VCH: New York, 1999; pp 654-657) followed by two-fold cross-coupling to 2,6-dibromopyridine. Treatment of diamine 6 with an excess of chloroacetylchloride in $CH_2Cl_2$ afforded diamide 7 in very good yield. Reaction of arene 7 with potassium thioacetate in DMF (van Bommel, K. J. C.; de Jong, M. R.; Metselaar, G. A.; Verboom, W.; Huskens, J.; Hulst, R.; Kooijman, H.; Spek, A. L.; Reinhoudt, D. N. *Chem. Eur. J.* 2001, 7, 3603-3615) resulted in acetyl-protected receptor 8. Crystals of arene 8 suitable for single crystal X-ray diffraction, obtained from slow diffusion of hexanes into a concentrated solution of 8 in EtOAc, indicated a dimeric association with intermolecular H-bonding. Treatment of 8 with $K_2CO_3$ in MeOH and THF under both air-free and ambient conditions afforded the intramolecular disulfide analog 10 in 77% yield instead of the free thiol 9. The disulfide bond of 10 enforces a pre-organization of the phenylacetylene substituents with the amide-N, disulfide linkage, and pyridine-N in a potential binding cavity.

An alternate synthetic route for receptor 9 was investigated following the scheme:

4 
1. $ClC(O)CH_2Cl$ $Et_3N$, $CH_2Cl_2$
2. $KSC(O)CH_3$ DMF
→

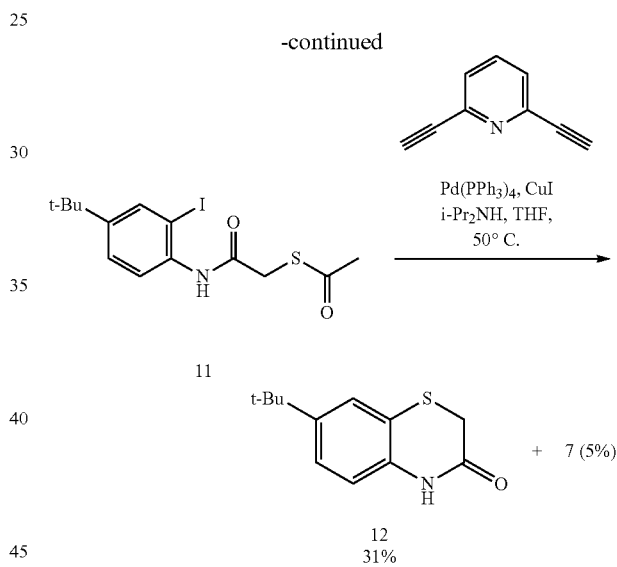

Successive treatment of iodoarene 4 with chloroacetylchloride and potassium thioacetate afforded intermediate 11. Pd-catalyzed cross-coupling of 11 to 2,6-diethynylpyridine (Dana, B. H.; Robinson, B. H.; Simpson, J. *J. Organomet. Chem.* 2002, 648, 251-269) produced penultimate 8 in very low yield (5%) due to competitive formation of benzothiazinone 12 from iodoarene 11. Both slow addition of the diethynylpyridine to a solution of 11 as well as direct combination of the two starting materials resulted in similar product distribution, with 12 as the major product. Benzothiazinone formation can be rationalized by pyridine base or metal catalyst deprotection of the thiol moiety followed by nucleophilic displacement of the iodide, a prearranged and favorable formation of an unsaturated six-membered ring. Conversion of 11 to 12 effectively prevented further cross coupling to the central pyridine core and hence resulted in low yield for arene 8. The remainder of the product distribution could not be discerned but likely included disulfide and/or oligomeric analogs of both 10 and 11.

Absorption and Emission Data:

Compounds 6-8 and 10 are fluorescent chromophores that exhibit blue or purple fluorescence under UV light (365 nm). The absorption spectra of compounds 6-8 and 10 are dominated by a characteristic pattern consisting of three peaks. There is a lack of significant spectral changes associated with conversion of diamide 8 to disulfide 10, which is not unexpected, as overall conjugation remains limited by the methylene spacer. Upon addition of TFA, 10 displayed enhanced low energy absorption (>100 nm) as well as conversion from a colorless solution with purple fluorescence to a deep yellow solution with yellow fluorescence. Treatment of the acidic solution with aqueous base resulted in return of the original absorption spectrum and fluorescence of 10.

Example 10

This example describes the synthesis and characterization of 4-tert-Butyl-2-(2-trimethylsilylethynyl)aniline 14 via the scheme:

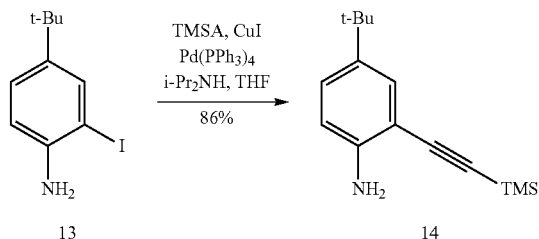 [SMILES: CC(C)(C)c1ccc(N)c(I)c1 ; CC(C)(C)c1ccc(N)c(C#C[Si](C)(C)C)c1]

A suspension consisting of 4-tert-butyl-2-iodoaniline 13 (800 mg, 2.9 mmol), Pd(PPh$_3$)$_4$ (168 mg, 0.15 mmol), and CuI (55 mg, 0.29 mmol) in i-Pr$_2$NH (50 mL) and THF (50 mL) was degassed by bubbling Ar. TMSA (1.3 mL, 9 mmol) was added and the suspension was stirred at room temperature for 12 hours under N$_2$. The suspension was filtered and the insoluble salts washed twice with Et$_2$O. The filtrate was combined with the Et$_2$O washes, concentrated, and purified by Chromatotron (3:2 hexanes:CH$_2$Cl$_2$) to afford 14 (611 mg, 86%) as a red-brown oil. $^1$H NMR (300 MHz, CDCl$_3$): δ 7.32 (d, J=2.1 Hz, 1H), 7.17 (dd, J=8.4, 2.1 Hz, 1H), 6.65 (d, J=8.4 Hz, 1H), 4.13 (br s, 2H), 1.27 (s, 9H), 0.29 (s, 9H). $^{13}$C NMR (75 MHz, CDCl$_3$): δ 145.87, 140.55, 128.68, 127.21, 114.09, 107.25, 102.40, 98.99, 33.79, 31.33, 0.16. IR (neat) ν 3476, 3381, 2960, 2868, 2147, 1500 cm$^{-1}$. MS (CI pos) m/z (%): 316 (M$^+$+THF, 38), 279 (M$^+$+Na$^+$, 35), 247 (M$^+$+2, 23), 246 (MH$^+$, 100); C$_{15}$H$_{23}$NSi (245.44).

Example 11

This example describes the synthesis and characterization of the compound referred to above as arene 3:

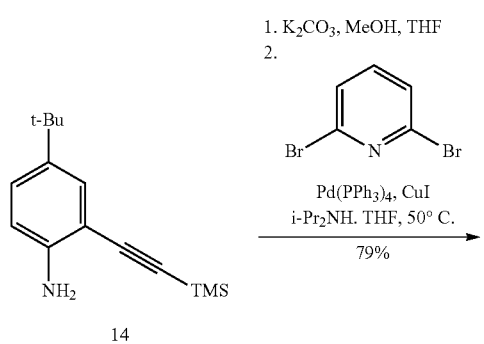

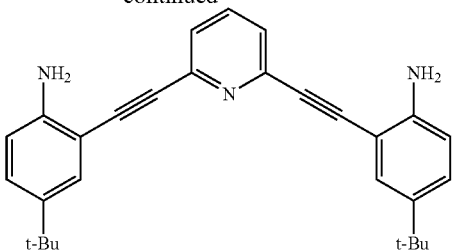

A suspension of ethynylarene 14 (206 mg, 0.84 mmol) and K$_2$CO$_3$ (5 equiv.) in MeOH (20 mL) and Et$_2$O (10 mL) was stirred at room temperature and monitored by TLC until completion (15-30 min). The solution was diluted with Et$_2$O and washed with water and brine. The organic layer was dried over MgSO$_4$ and concentrated in vacuo. Without further purification, the residue was dissolved in THF (10 mL) and added dropwise over a period of 12 hours to a stirred, deoxygenated suspension of 2,6-dibromopyridine (50 mg, 0.21 mmol), Pd(PPh$_3$)$_4$ (25 mg, 0.02 mmol), and CuI (8 mg, 0.04 mmol) in THF (50 mL) and i-Pr$_2$NH (50 mL) at 45° C. After an additional 3 hours of stirring, the suspension was filtered and the insoluble salts washed twice with Et$_2$O. The filtrate was combined with the Et$_2$O washes, concentrated, and purified by Chromatotron (3:2 hexanes:EtOAc) to afford 3 (70 mg, 79%) as a pale brown, crystalline solid. Mp: 226° C. $^1$H NMR (300 MHz, CDCl$_3$): δ 7.64 (t, J=8.1 Hz, 1H), 7.45-7.43 (m, 4H), 7.20 (dd, J=8.7, 1.8 Hz, 2H), 6.67 (d, J=8.7 Hz, 2H), 4.35 (br s, 4H), 1.27 (s, 18H). $^{13}$C NMR (75 MHz, CDCl$_3$): δ 146.31, 143.84, 140.56, 136.36, 129.24, 128.04, 125.73, 114.34, 105.82, 93.11, 87.59, 33.85, 31.31. IR (neat) ν 3451, 3355, 2957, 2866, 2199, 1500 cm$^{-1}$. UV/vis (CH$_2$Cl$_2$): λ$_{max}$ (ε) 249 (44,200), 295 (24,300), 359 (22,500) nm. MS (CI pos) m/z (%): 423 (M$^+$+2, 100), 422 (MH$^+$, 100); C$_{29}$H$_{31}$N$_3$ (421.58).

Example 12

This example describes the synthesis and characterization of the compound referred to above as arene 7:

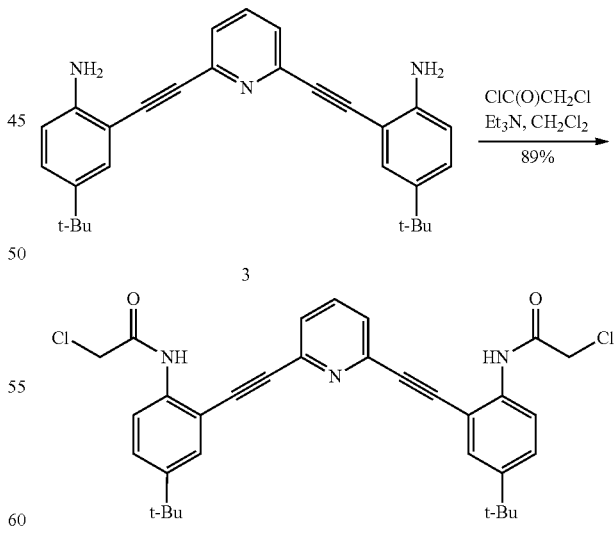

A solution of chloroacetylchloride (571 mg, 5.1 mmol) in CH$_2$Cl$_2$ (10 mL) was added to a stirred, deoxygenated solution of arene 3 (395 mg, 0.94 mmol) and Et$_3$N (379 mg, 3.76 mmol) in CH$_2$Cl$_2$ (10 mL). The reaction was stirred for 12 hours at room temperature under N$_2$ and then concentrated in vacuo. CH$_2$Cl$_2$ was added and the organic layer was washed thrice with water, dried over MgSO$_4$, and concentrated in vacuo. The crude material was filtered through a 2.5 cm silica plug (1:1 hexanes:EtOAc) and concentrated to afford 4 (476 mg, 89%) as a pale brown solid. Mp: 193° C. $^1$H NMR (300 MHz, CDCl$_3$): δ 9.23 (br s, 2H), 8.30 (d, J=8.3 Hz, 2H), 7.72 (t, J=8.3 Hz, 1H), 7.64 (d, J=2.1 Hz, 2H), 7.52 (d, J=8.1 Hz, 2H), 7.43 (dd, J=8.1, 2.1 Hz, 2H), 4.27 (s, 4H), 1.31 (s, 18H). $^{13}$C NMR (75 MHz, CDCl$_3$): δ 163.62, 147.46, 143.19, 136.83, 135.83, 129.32, 127.87, 126.20, 119.07, 111.15, 94.78, 84.80, 43.21, 34.41, 31.10. IR (neat) v 3363, 2962, 2868, 2207, 1691, 1523 cm$^{-1}$. UV/vis (CH$_2$Cl$_2$): λ$_{max}$ (ε) 254 (52,600), 293 (27,700), 335 (27,600) nm. MS (CI pos) m/z (%): 578 (M$^+$+4, 15), 577 (M$^+$+3, 23), 576 (M$^+$+2, 75), 575 (MH$^+$, 38), 574 (M$^+$, 100); C$_{33}$H$_{33}$Cl$_2$N$_3$O$_2$ (574.54).

Example 13

This example describes the synthesis and characterization of the compound referred to above as arene 8:

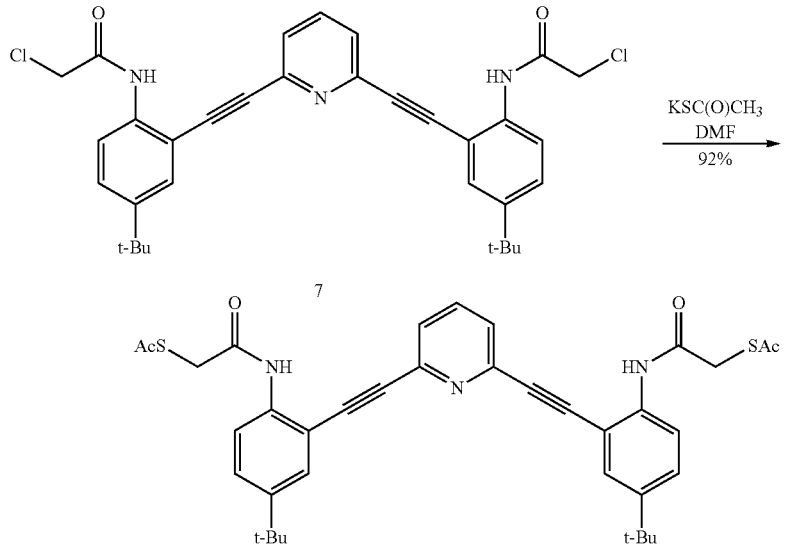

Potassium thioacetate (16 mg, 0.14 mmol) was added to a stirred, deoxygenated solution of arene 7 (34 mg, 0.06 mmol) in DMF (3 mL). The reaction was stirred for 12 hours at room temperature under N$_2$ and then concentrated in vacuo. The crude material was filtered through a 2.5 cm silica plug (1:1 hexanes:EtOAc) and purified via Chromatotron (2:1 hexanes: EtOAc) to afford 8 (35 mg, 92%) as a spongy light yellow solid. Recrystallization by diffusion (hexanes:EtOAc) afforded colorless crystals. Mp: 94° C. $^1$H NMR (300 MHz, CDCl$_3$): δ 8.75 (br s, 2H), 8.28 (d, J=8.7 Hz, 2H), 7.75 (s, 3H), 7.58 (d, J=2.4 Hz, 2H), 7.39 (dd, J=8.7, 2.4 Hz, 2H), 3.76 (s, 4H), 2.34 (s, 6H), 1.28 (s, 18H). $^{13}$C NMR (75 MHz, CDCl$_3$): δ 195.20, 166.16, 146.81, 143.31, 136.59, 136.54, 129.38, 127.68, 126.57, 119.45, 110.79, 94.31, 85.15, 34.27, 33.99, 31.05, 30.13. IR (neat) v 3339, 3058, 2962, 2868, 2208, 1693, 1518 cm$^{-1}$. UV/vis (CH$_2$Cl$_2$): λ$_{max}$ (ε) 253 (48,200), 291 (24,500), 330 (21,600) nm. MS (CI pos) m/z (%): 656 (M$^+$+2, 19), 655 (MH$^+$, 44), 654 (M$^+$, 100); C$_{37}$H$_{39}$N$_3$O$_4$S$_2$ (653.85).

Example 14

This example describes the synthesis and characterization of the compound referred to above as disulfide 10.

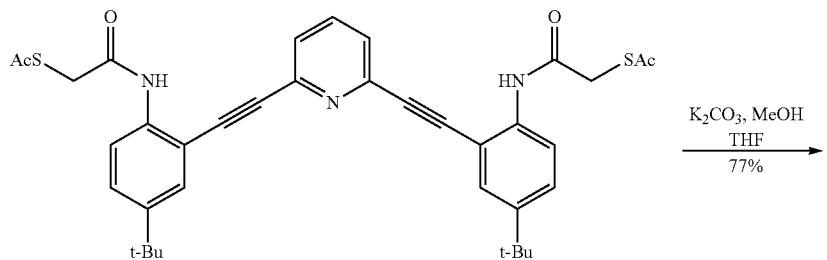

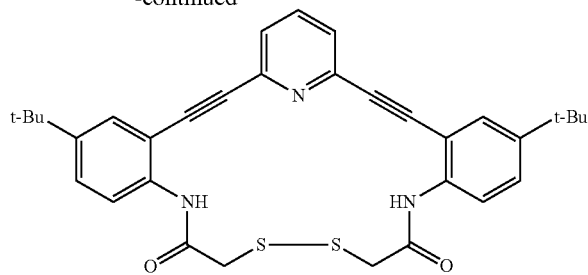

10

K₂CO₃ (3 equiv) was added to a deoxygenated solution of 8 (23 mg, 0.03 mmol) in MeOH (5 mL) and THF (3 mL). The suspension was stirred at room temperature under $N_2$ for 30 minutes and completion was monitored by TLC. $Et_2O$ was added and the reaction mixture was washed with water and/or a saturated solution of $NH_4Cl$. The aqueous layer was further washed with $Et_2O$ twice. The organics were combined and dried over $MgSO_4$. Concentration and purification via Chromatotron (3:2 hexanes:EtOAc) afforded 10 (17 mg, 77%) as a crystalline, white solid. Mp: 247° C. ¹H NMR (300 MHz, CDCl₃): δ 9.79 (br s, 2H), 8.47 (d, J=9 Hz, 2H), 7.72 (t, J=7.7 Hz, 1H), 7.57 (d, J=2.1 Hz, 2H), 7.51 (d, J=8.1 Hz, 2H), 7.46 (dd, J=8.8, 2.1 Hz, 2H), 3.70 (s, 4H), 1.58 (s, 2H), 1.34 (s, 18H). IR (neat) v 3318, 2959, 2925, 2855, 2207, 1687, 1515 cm⁻¹. UV/vis (CH₂Cl₂): λ$_{max}$ (ε) 254 (52,200), 296 (24,800), 323 (17,800), 337 (17,500) nm. MS (CI pos) m/z (%): 570 (M⁺+1, 19), 569 (MH⁺, 38), 568 (M⁺, 100); C₃₃H₃₃N₃O₂S₂ (567.76).

Alternate route product, benzothiazinone 12

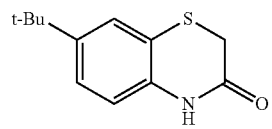

9 had the spectral data ¹H NMR (300 MHz, CDCl₃): δ 7.30 (d, J=1.2 Hz, 1H), 7.18 (dd, J=4.8, 1.2 Hz, 1H), 6.82 (d, J=4.8 Hz, 1H), 3.43 (s, 2H), 1.29 (s, 9H). MS (CI pos) m/z (%): 279 (M⁺+H₂O+CH₃CN, 100), 263 (M⁺+CH₃CN, 73), 218 (M⁺−3, 61); C₁₂H₁₅NOS (221.32).

Example 15

This example describes the synthesis of host compounds according to the scheme:

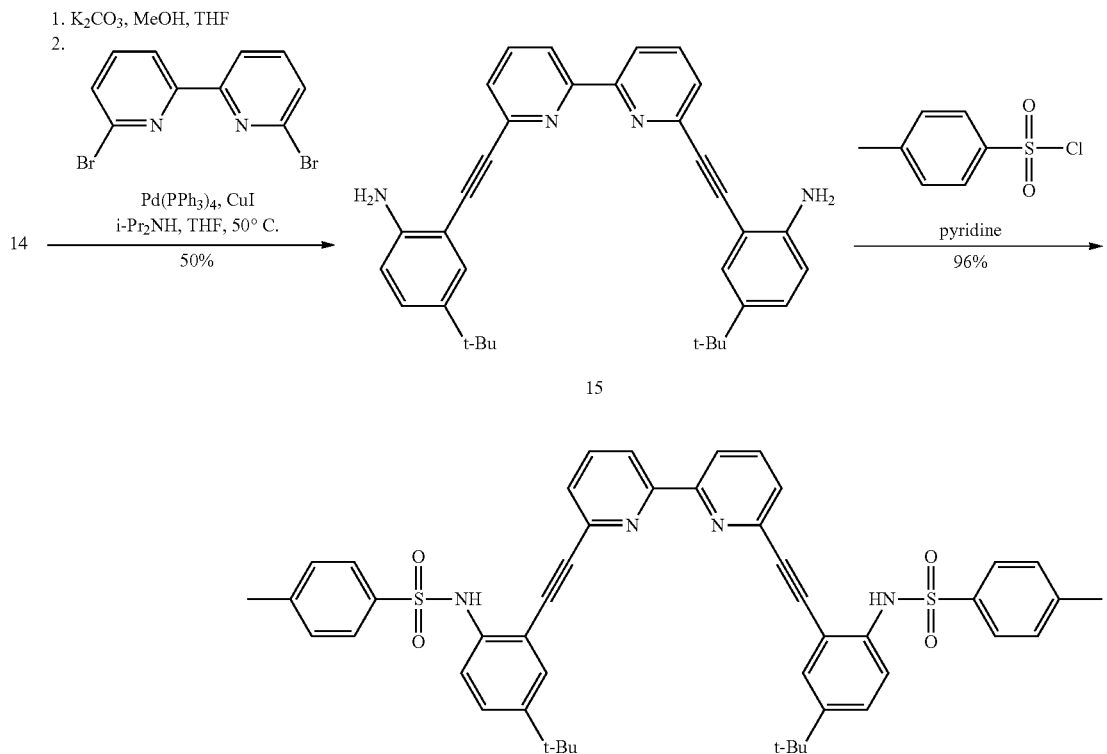

A suspension of ethynylarene 14 (391 mg, 1.6 mmol) and K₂CO₃ (5 equiv.) in MeOH (20 mL) and Et₂O (10 mL) was stirred at room temperature and monitored by TLC until completion (15-30 minutes). The solution was diluted with Et₂O and washed with water and brine. The organic layer was dried over MgSO₄ and concentrated in vacuo. Without further purification, the residue was dissolved in THF (10 mL) and added dropwise over a period of 12 hours to a stirred, deoxygenated suspension of 6,6'-dibromo-2,2'-dipyridyl (200 mg, 0.64 mmol), Pd(PPh₃)₄ (173 mg, 0.2 mmol), and CuI (60 mg, 0.3 mmol) in THF (100 mL) and i-Pr₂NH (100 mL) at 50° C. After an additional 3 hours of stirring, the suspension was concentrated and filtered through a 2.5 cm silica plug (1:1 hexanes:EtOAc). Purification by column chromatography (CH₂Cl₂) afforded 15 (159 mg, 50%) as a bright yellow, crystalline solid. ¹H NMR (300 MHz, CDCl₃): δ 8.45 (d, J=7.2 Hz, 2H), 7.81 (t, J=8.1 Hz, 2H), 7.55 (d, J=8.1 Hz, 2H), 7.48 (d, J=2.3 Hz, 2H), 7.22 (dd, J=8.4, 2.3 Hz, 2H), 6.70 (d, J=8.4 Hz, 2H), 4.29 (br s, 4H), 1.30 (s, 18H).

Arene 15 (25 mg, 0.05 mmol) was reacted with p-toluenesulfonyl chloride according to General Preparation of Sulfonamides. Chromatography on silica gel (3:1 hexanes:EtOAc) afforded 16 (38 mg, 96%) as a pale yellow solid. Recrystallization by diffusion (hexanes:EtOAc) afforded colorless crystals. Mp: 251-252° C. ¹H NMR (300 MHz, CDCl₃): δ 8.58 (d, J=7.8 Hz, 2H), 7.90 (t, J=7.8 Hz, 2H), 7.77 (d, J=8.4 Hz, 4H), 7.58-7.42 (m, 8H), 7.37 (dd, J=8.8, 2.4 Hz, 2H), 7.14 (d, J=7.8 Hz, 4H), 2.32 (s, 6H), 1.29 (s, 18H). ¹³C NMR (125 MHz, CDCl₃): δ 155.86, 147.77, 143.85, 141.95, 137.44, 136.36, 135.74, 129.54, 129.18, 127.75, 127.40, 127.29, 121.15, 120.63, 113.34, 94.77, 84.26, 34.40, 31.13, 21.52. Fluorescence emission ([16]≤5.7×10⁻⁵ M in CHCl₃; 343 nm excitation): $\lambda_{max}$ 390 nm. MS (CI pos) m/z (%): 809 (M⁺+2, 29), 808 (MH⁺, 63), 807 (M⁺, 100); C₄₈H₄₆N₄O₄S₂ (807.03).

Example 16

This example describes the synthesis of host compounds according to the scheme:

A suspension of ethynylarene 14 (500 mg, 2 mmol) and K₂CO₃ in MeOH (20 mL) and Et₂O (10 mL) was stirred at room temperature and monitored by TLC until completion (15-30 minutes). The solution was diluted with Et₂O and washed with water and brine. The organic layer was dried over MgSO₄ and concentrated in vacuo. Without further purification, the residue was dissolved in THF (10 mL) and added dropwise over a period of 12 hours to a stirred, deoxygenated suspension of 2,5-dibromothiophene (225 mg, 0.93 mmol), Pd(PPh₃)₄ (231 mg, 0.2 mmol), and CuI (76 mg, 0.4 mmol) in THF (50 mL) and i-Pr₂NH (50 mL) at 45° C. After an additional 3 hours of stirring, the suspension was concentrated and filtered through a 2.5 cm silica plug (CH₂Cl₂). Purification by column chromatography (CH₂Cl₂) afforded 17 (297 mg, 75%) as a bright yellow, crystalline solid. ¹H NMR (300 MHz, CDCl₃): δ 7.37 (d, J=2.1 Hz, 2H), 7.21 (dd, J=8.5, 2.1 Hz, 2H), 7.15 (s, 2H), 6.68 (d, J=8.5 Hz, 2H), 4.16 (br s, 4H), 1.29 (s, 18H). ¹³C NMR (75 MHz, CDCl₃): δ 145.52, 140.92, 131.49, 128.62, 127.63, 124.52, 114.38, 106.67, 91.25, 86.75, 33.89, 31.33. MS (CI pos) m/z (%): 498 (M⁺+2+THF, 18), 497 (MH⁺+THF, 100), 428 (M⁺+2, 18), 427 (MH⁺, 53); C₂₈H₃₀N₂S (426.21).

A solution of arene 17 (90 mg, 0.2 mmol) was reacted with p-toluenesulfonyl chloride according to General Preparation of Sulfonamides. Chromatography on silica gel (CH₂Cl₂) afforded 18 (123 mg, 82%) as a pale yellow solid. Mp: 89-91° C. ¹H NMR (300 MHz, CDCl₃): δ 7.68 (d, J=8.7 Hz, 4H), 7.54 (d, J=8.4 Hz, 2H), 7.39-7.34 (m, 4H), 7.22 (d, J=8.7 Hz, 4H), 7.16 (s, 2H), 7.03 (s, 2H), 2.38 (s, 6H), 1.28 (s, 18H). ¹³C NMR (75 MHz, CDCl₃): δ 147.99, 144.00, 136.21, 134.96, 132.48, 129.66, 128.98, 127.63, 127.20, 124.09, 120.98, 113.79, 89, 54, 87.36, 34.39, 31.10, 21.58. UV/vis (CH₂Cl₂): $\lambda_{max}$ (ε) 234 (58,000), 287 (31,000), 330 (27,600) nm. Fluorescence emission ([18]≤5.7×10⁻⁵ M in CHCl₃; 289 nm excitation): $\lambda_{max}$ 424 nm. MS (CI pos) m/z (%): 807 (M⁺+2+THF,

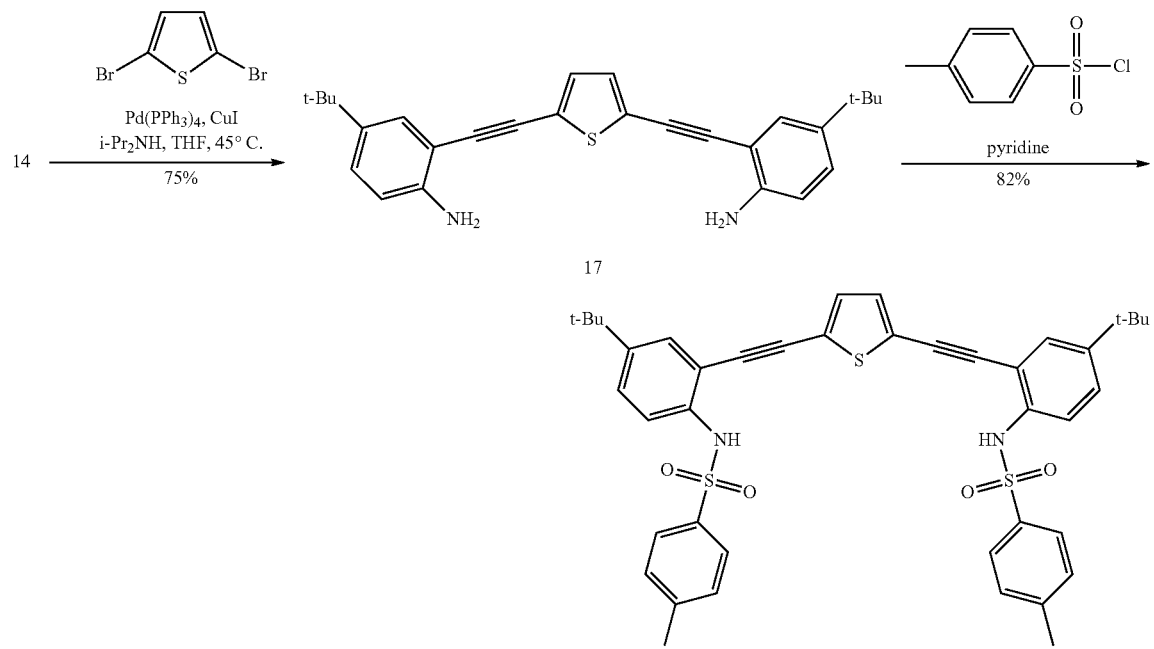

16), 806 (MH$^+$+THF, 38), 805 (M$^+$+THF, 63), 737 (M$^+$+2, 21), 736 (MH$^+$, 37), 735 (M$^+$, 71), 595 (100), 580 (89); $C_{42}H_{42}N_2O_4S_3$ (734.99).

Example 17

Described herein is the synthesis of a library of sixteen different 2,6-bis(2-aniloethynyl)pyridine bisureas (2-5/a-d). Also reported is an exhaustive study of their absorption and emission profiles in $CH_3CN$, and ultimately show that a similar "turn-on" behavior can be observed even in relatively polar solvents.

To obtain a full range of electron-poor and electron-rich scaffolds, 2,6-bis(2-aniloethynyl)pyridine derivatives functionalized with tert-butyl (6), carboethoxy (7), trifluoromethyl (8), and methoxy (9) groups located at the 4-position on the aniline rings were synthesized. Each derivative was synthesized via a twofold Sonogashira cross-coupling reaction between the respective 4-functionalized-2-ethynylanilines with 2,6-dibromopyridine as shown in Scheme 1 below; thus, protiodesilation of known anilines 10-13 in basic MeOH (EtOH for 11) followed by cross-coupling afforded the 2,6-bis(2-aniloethynyl)pyridine cores 6-9 in good to excellent yield. Each of these derivatives was then reacted with 4-methoxyphenyl isocyanate (a), 4-nitrophenyl isocyanate (b), phenyl isocyanate (c) and pentafluorophenyl isocyanate (d) to furnish the sixteen bisureas 2-5/a-d.

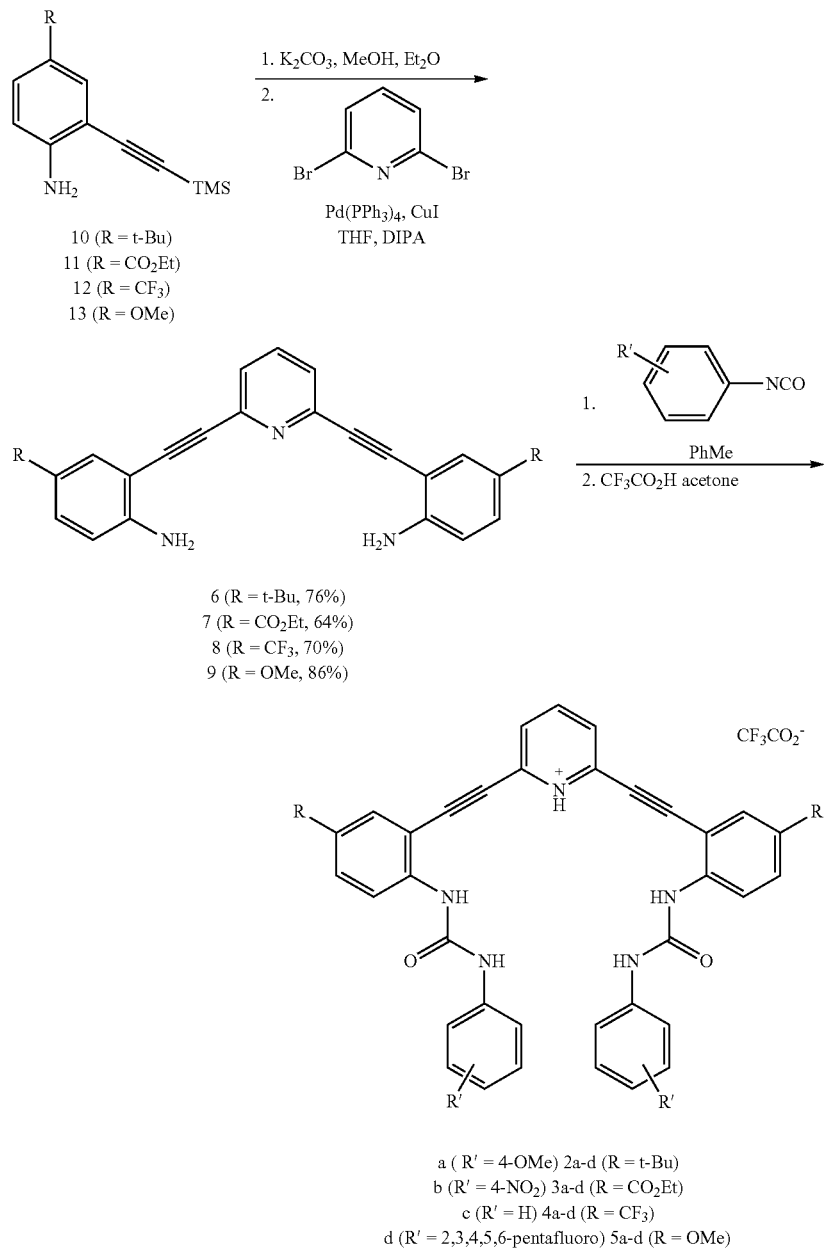

Scheme 1 Synthesis of differentially substituted 2,6-ethynylpyridine bis-phenylurea scaffolds.

General TMS Deprotection Procedure A. To a solution of 4-substituted-2-(trimethylsilylethynyl)aniline (10-13, 1 equiv) in 2:1 MeOH/Et$_2$O (0.1 M) was added K$_2$CO$_3$ (5 equiv) at room temperature. After stirring for 1 h, the reaction mixture was diluted with water and extracted with CH$_2$Cl$_2$. The organic layer was dried over MgSO$_4$, filtered and concentrated under reduced pressure to give the desilylated product which was used without further purification.

General Cross Coupling Procedure B. To an Ar degassed solution of 2,6-dibromopyridine (1 equiv) in 1:1 THF/DIPA (0.05 M) were added CuI (0.2 equiv) and Pd(PPh$_3$)$_4$ (0.1 equiv) at room temperature. The solution was degassed with Ar for an additional 30 min and then heated to 50° C. To this solution a second degassed solution of 2-ethynyl-4-substituted aniline (2.2 equiv) in THF (20 mL) was cannula transferred. After stirring for 16 h, the reaction mixture was cooled, diluted with CH$_2$Cl$_2$, and filtered through a 4 cm pad of silica. The filtrate was concentrated under reduced pressure. The crude product was purified by flash chromatography over silica gel to give the desired dianiline product.

General Urea Formation Procedure C. To a stirred solution of 2,6-bis(2-anilinoethynyl)pyridine (6-9, 1 equiv) in dry toluene (0.01 M) was added the appropriate phenylisocyanate reagent (3-10 equiv). The reaction was stirred at rt-80° C. for 3 h-2 d. The resulting suspension was diluted in hexanes and the solid precipitate was collected via vacuum filtration. The solid was redissolved in a minimal amount of 10:1 acetone/TFA and hexanes was added until the solution became cloudy. The resulting suspension was cooled and the precipitate was collected via vacuum filtration affording the desired product.

t-Butyl Dianiline 6:

Aniline 10 (0.631 g, 3.41 mmol) was deprotected according to general procedure A and reacted with 2,6-dibromopyridine (0.337 g, 1.55 mmol), CuI (59 mg, 0.31 mmol), and Pd(PPh$_3$)$_4$ (179 mg, 0.16 mmol) using general procedure B. The crude product was then dissolved in EtOAc and triturated with hexanes until cloudy. The resulting suspension was cooled in an ice bath for 1 h and the product was filtered and dried to give 6 (0.48 g, 70%) as a yellow solid: $^1$H NMR (600 MHz, CDCl$_3$) δ 7.65 (t, J=7.8 Hz, 1H), 7.49-7.39 (m, 4H) 7.21 (dd, J=8.5, 1.8 Hz, 2H), 6.68 (d, J=8.5 Hz, 2H), 4.31 (s, 4H), 1.28 (s, 18H). $^{13}$C NMR (151 MHz, CDCl$_3$) δ 146.43, 144.10, 140.88, 136.51, 129.47, 128.21, 125.89, 114.54, 106.15, 93.37, 87.61, 34.07, 31.51.

Ester Dianiline 7:

Benzoate 11 (2.13 g, 11.3 mmol) was deprotected according to general procedure A and reacted with 2,6-dibromopyridine (1.21 g, 5.13 mmol), CuI (150 mg, 0.79 mmol), and Pd(PPh$_3$)$_4$ (250 mg, 0.22 mmol) using general procedure B. The crude product was then dissolved in EtOAc and triturated with hexanes until cloudy. The resulting suspension was cooled in an ice bath for 1 h and the product was filtered and dried to give 7 (1.50 g, 64%) as a yellow solid: $^1$H NMR (600 MHz, CDCl$_3$) δ 8.14 (d, J=1.9 Hz, 2H), 7.85 (dd, J=8.6, 1.9 Hz, 2H), 7.70 (t, J=7.8 Hz, 1H), 7.48 (d, J=7.8 Hz, 2H), 6.70 (d, J=8.6 Hz, 2H), 4.85 (s, 4H), 4.33 (q, J=7.1 Hz, 4H), 1.38 (t, J=7.1 Hz, 6H). $^{13}$C NMR (151 MHz, CDCl$_3$) δ 166.09, 152.20, 143.77, 136.77, 135.19, 132.45, 126.36, 119.95, 113.60, 105.66, 93.93, 85.90, 60.71, 14.56.

Trifluoromethyl Dianiline 8:

Aniline 12 (0.631 g, 3.41 mmol) was deprotected according to general procedure A and reacted with 2,6-dibromopyridine (0.337 g, 1.55 mmol), CuI (59 mg, 0.31 mmol), and Pd(PPh$_3$)$_4$ (179 mg, 0.16 mmol) using general procedure B. The crude product was then dissolved in EtOAc and triturated with hexanes until cloudy. The resulting suspension was cooled in an ice bath for 1 h and the product was filtered and dried to give 8 (0.48 g, 70%) as an off-white solid: $^1$H NMR (600 MHz, CDCl$_3$) δ 7.72 (t, J=7.8 Hz, 1H), 7.67 (d, J=1.8 Hz, 2H), 7.49 (d, J=7.8 Hz, 2H), 7.38 (dd, J=8.6, 1.8 Hz, 2H), 6.75 (d, J=8.6 Hz, 2H), 4.78 (s, 4H). $^{13}$C NMR (151 MHz, CDCl$_3$) δ 151.14, 143.59, 136.87, 130.28 (q, J=3.9 Hz), 127.66 (q, J=3.6 Hz), 126.48, 124.38 (d, J=270.7 Hz), 119.93 (q, J=33.2 Hz), 114.08, 105.90, 94.29, 85.47.

Methoxy Dianiline 9:

Aniline 13 (1.46 g, 9.91 mmol) was deprotected according to general procedure A and reacted with 2,6-dibromopyridine (1.118 g, 4.72 mmol), CuI (150 mg, 0.79 mmol), and Pd(PPh$_3$)$_4$ (250 mg, 0.22 mmol) using general procedure B. The crude product was then dissolved in EtOAc and triturated with hexanes until cloudy. The resulting suspension was cooled in an ice bath for 1 h and the product was filtered and dried to give 9 (1.50 g, 86%) as a light brown solid: $^1$H NMR (600 MHz, CDCl$_3$) δ 7.66 (t, J=7.8 Hz, 1H), 7.45 (d, J=7.8 Hz, 2H), 6.96 (d, J=2.9 Hz, 2H), 6.81 (dd, J=8.8, 2.9 Hz, 2H), 6.68 (d, J=8.8 Hz, 2H), 4.15 (s, 4H), 3.75 (s, 6H). $^{13}$C NMR (151 MHz, cdcl$_3$) δ 151.90, 143.93, 143.13, 136.59, 126.10, 118.88, 116.27, 116.08, 107.08, 93.66, 87.02, 55.97.

Bis-Urea 2a:

Dianiline 6 (43.3 mg, 0.095 mmol) and 4-methoxyphenyl isocyanate (120 μL, 0.96 mmol) were reacted at 80° C. for 16 h using general procedure C to afford the desired product 2a (47.5 mg, 57%) as an yellow solid $^1$H NMR (600 MHz, DMSO-d6) δ 9.27 (s, 2H), 8.22 (s, 2H), 8.02 (d, J=8.8 Hz, 2H), 7.99 (t, J=7.8 Hz, 1H), 7.81 (d, J=7.8 Hz, 2H), 7.53 (d, J=2.4 Hz, 2H), 7.47 (dd, J=8.8, 2.3 Hz, 2H), 7.37 (d, J=9.0 Hz, 4H), 6.87 (d, J=9.0 Hz, 4H), 3.71 (s, 6H), 1.29 (s, 18H). $^{13}$C NMR (151 MHz, DMSO-d6) δ 154.61, 152.36, 144.51, 142.82, 138.46, 137.41, 132.42, 129.02, 127.59, 127.25, 120.16, 119.88, 114.04, 109.99, 93.46, 85.87, 55.14, 33.95, 30.97.

Bis-Urea 2b:

Dianiline 6 (89 mg, 0.196 mmol) and 4-nitrophenyl isocyanate (193 mg, 1.18 mmol) were reacted at rt for 16 h using general procedure C. Purification using general procedure E afforded the desired product (46.5 mg, 30%). $^1$H NMR (600 MHz, DMSO-d6) δ 10.12 (s, 2H), 8.53 (s, 2H), 8.19 (d, J=9.2 Hz, 4H), 8.02-7.96 (m, 3H), 7.82 (d, J=7.8 Hz, 2H), 7.71 (d, J=9.2 Hz, 4H), 7.57 (d, J=2.3 Hz, 2H), 7.51 (dd, J=8.8, 2.3 Hz, 2H), 1.30 (s, 18H). $^{13}$C NMR (151 MHz, DMSO-d6) δ 151.78, 146.08, 145.58, 142.75, 141.16, 137.49, 129.20, 127.68, 127.38, 125.15, 120.52, 117.56, 111.02, 93.55, 85.67, 34.04, 30.93.

Bis-Urea 2c:

Dianiline 6 (0.337 g, 1.55 mmol) and phenyl isocyanate (59 mg, 0.31 mmol) were reacted at rt for 16 h using general procedure E. Purification using general procedure E afforded the desired product. $^1$H NMR (600 MHz, DMSO-d6) δ 9.44 (s, 2H), 8.32 (s, 2H), 8.00 (dd, J=15.1, 8.4 Hz, 3H), 7.82 (d, J=7.8 Hz, 2H), 7.55 (d, J=2.3 Hz, 2H), 7.51-7.43 (m, 6H), 7.29 (t, J=7.9 Hz, 4H), 6.99 (t, J=7.3 Hz, 2H), 1.30 (s, 18H). $^{13}$C NMR (151 MHz, DMSO-d6) δ 152.22, 144.77, 142.82, 139.46, 138.24, 137.45, 129.07, 128.84, 127.61, 127.30, 122.05, 120.11, 118.29, 110.26, 93.46, 85.85, 33.98, 30.96.

Bis-Urea 2d:

Dianiline 6 (75.3 mg, 0.169 mmol) and pentafluorophenyl isocyanate (66 μL, 0.507 mmol) were reacted at 80° C. for 16 h using general procedure E. Purification using general procedure E afforded the desired product (115 mg, 81%). $^1$H NMR (600 MHz, DMSO-d6) δ 9.34 (s, 2H), 8.64 (s, 2H), 8.01 (t, J=7.8 Hz, 1H), 7.96 (d, J=8.8 Hz, 2H), 7.81 (d, J=7.8 Hz, 2H), 7.57 (d, J=1.6 Hz, 2H), 7.49 (d, J=8.8 Hz, 2H), 1.29 (s, 18H). $^{13}$C NMR (151 MHz, dmso) δ 151.67, 145.48, 142.78, 143.64-141.64 (m), 139.36-137.49 (m), 137.67, 137.45, 138.20-136.16 (m), 129.17, 127.72, 127.33, 120.07, 113.84-113.42 (m), 110.77, 93.52, 85.59, 34.02, 30.92.

Bis-Urea 3a:

Dianiline 7 (43.3 mg, 0.095 mmol) and 4-methoxyphenyl isocyanate (120 µL, 0.96 mmol) were reacted at 80° C. for 16 h using general procedure C to afford the desired product 3a (47.5 mg, 57%) as an orange solid. $^1$H NMR (600 MHz, DMSO-d6) δ 9.56 (s, 2H), 8.57 (s, 2H), 8.36 (d, J=8.9 Hz, 2H), 8.12 (d, J=1.9 Hz, 2H), 8.05 (t, J=7.8 Hz, 1H), 7.98 (dd, J=8.9, 1.9 Hz, 2H), 7.90 (d, J=7.8 Hz, 2H), 7.40 (d, J=8.9 Hz, 4H), 6.89 (d, J=8.9 Hz, 4H), 4.31 (q, J=7.1 Hz, 4H), 3.72 (s, 6H), 1.33 (t, J=7.1 Hz, 6H). $^{13}$C NMR (151 MHz, DMSO-d6) δ 164.58, 154.96, 151.80, 144.88, 142.49, 137.60, 133.93, 131.84, 131.24, 127.90, 123.00, 120.50, 118.61, 114.10, 109.54, 94.51, 84.02, 60.71, 55.15, 14.16.

Bis-Urea 3b:

Dianiline 7 (89 mg, 0.196 mmol) and 4-nitrophenyl isocyanate (193 mg, 1.18 mmol) were reacted at rt for 16 h using general procedure C. Purification using general procedure E afforded the desired product (46.5 mg, 30%). $^1$H NMR (300 MHz, DMSO-d6) δ 10.37 (s, 2H), 8.84 (s, 2H), 8.34 (d, J=8.8 Hz, 2H), 8.20 (d, J=9.0 Hz, 4H), 8.14 (d, J=1.9 Hz, 2H), 8.11-7.97 (m, 3H), 7.92 (d, J=7.8 Hz, 2H), 7.72 (d, J=9.0 Hz, 4H), 4.32 (q, J=7.1 Hz, 4H), 1.33 (t, J=7.1 Hz, 6H). $^{13}$C NMR (126 MHz, DMSO-d6) δ 164.98, 151.88, 146.05, 144.46, 142.91, 141.97, 138.14, 134.44, 131.77, 128.52, 125.64, 124.37, 119.70, 118.36, 110.90, 95.18, 84.36, 61.32, 14.63.

Bis-Urea 3c:

Dianiline 7 (44.4 mg, 0.0979 mmol) and phenyl isocyanate (110 µL, 0.979 mmol) were reacted at 80° C. for 16 h using general procedure E. Purification using general procedure E afforded the desired product (20.7 mg, 26%). $^1$H NMR (500 MHz, DMSO-d6) δ 9.74 (s, 2H), 8.67 (s, 2H), 8.36 (d, J=8.9 Hz, 2H), 8.13 (d, J=1.9 Hz, 2H), 8.05 (t, J=7.8 Hz, 1H), 7.99 (dd, J=8.9, 1.9 Hz, 2H), 7.92 (d, J=7.8 Hz, 2H), 7.50 (d, J=8.1 Hz, 4H), 7.31 (t, J=7.8 Hz, 4H), 7.03 (t, J=7.3 Hz, 2H), 4.32 (q, J=7.1 Hz, 4H), 1.33 (t, J=7.1 Hz, 6H). $^{13}$C NMR (126 MHz, DMSO-d6) δ 164.57, 151.70, 144.69, 142.49, 138.95, 137.63, 133.96, 131.25, 128.91, 127.96, 123.22, 122.56, 118.83, 118.60, 109.79, 94.54, 84.02, 60.75, 14.16.

Bis-Urea 3d:

Dianiline 7 (31.6 mg, 0.0697 mmol) and pentafluorophenyl isocyanate (50 µL, 0.42 mmol) were reacted at 80° C. for 16 h using general procedure E. Purification using general procedure E afforded the desired product (52 mg, 76%). $^1$H NMR (600 MHz, DMSO-d6) δ 10.05 (s, 2H), 9.18 (s, 2H), 8.29 (d, J=8.9 Hz, 2H), 8.14 (d, J=2.0 Hz, 2H), 8.08-8.01 (m, 3H), 7.99 (dd, J=8.8, 1.9 Hz, 2H), 4.31 (dd, J=14.2, 7.1 Hz, 4H), 1.33 (t, J=7.1 Hz, 6H). $^{13}$C NMR (151 MHz, DMSO-d6) δ 164.50, 151.50, 144.09, 142.41, 137.45, 133.97, 131.27, 128.03, 123.86, 119.00, 110.37, 94.71, 83.78, 60.81, 14.11.

Bis-Urea 4a:

Dianiline 8 (29.6 mg, 0.067 mmol) and 4-methoxyphenyl isocyanate (90 µL, 0.67 mmol) were reacted at 80° C. for 16 h using general procedure E. Purification using general procedure E afforded the desired product (9 mg, 16%). $^1$H NMR (600 MHz, DMSO-d6) δ 9.54 (s, 2H), 8.58 (s, 2H), 8.42 (d, J=8.9 Hz, 2H), 8.06 (t, J=7.8 Hz, 1H), 7.94 (d, J=1.4 Hz, 2H), 7.91 (d, J=7.8 Hz, 2H), 7.77 (dd, J=8.9, 1.5 Hz, 2H), 7.39 (d, J=9.0 Hz, 4H), 6.89 (d, J=9.0 Hz, 4H), 3.72 (s, 6H). $^{13}$C NMR (151 MHz, DMSO-d6) δ 158.23 (q, J=37.1 Hz), 154.97, 151.89, 144.23, 142.39, 137.66, 131.82, 129.77, 128.09, 127.13, 124.77, 122.97, 122.14 (q, J=32.4 Hz), 120.51, 119.35, 114.11, 110.06, 94.91, 83.64, 55.16.

Bis-Urea 4b:

Dianiline 8 (102 mg, 0.023 mmol) and 4-nitrophenyl isocyanate (188 mg, 1.14 mmol) were reacted at 70° C. for 16 h using general procedure E. Purification using general procedure E afforded the desired product (59.3 mg, 34%). $^1$H NMR (600 MHz, DMSO-d6) δ 10.35 (s, 2H), 8.87 (s, 2H), 8.39 (d, J=8.9 Hz, 2H), 8.20 (d, J=9.2 Hz, 4H), 8.07 (t, J=7.8 Hz, 1H), 7.99 (s, 2H), 7.93 (d, J=7.8 Hz, 2H), 7.83 (d, J=8.9 Hz, 2H), 7.72 (d, J=9.2 Hz, 4H). $^{13}$C NMR (151 MHz, DMSO-d6) δ 151.48, 145.52, 143.36, 142.33, 141.54, 137.72, 129.89 (t, J=6.1 Hz), 128.21, 127.24 (t, J=6.6 Hz), 125.15, 124.05 (t, J=407.7 Hz), 123.09 (q, J=32.7 Hz), 120.03, 117.92, 111.04, 95.07, 83.50.

Bis-Urea 4c:

Dianiline 8 (22.7 mg, 0.051 mmol) and phenyl isocyanate (60 µL, 0.51 mmol) were reacted at 80° C. for 16 h using general procedure E. Purification using general procedure E afforded the desired product (14.9 mg, 37%). $^1$H NMR (300 MHz, DMSO-d6) δ 9.71 (s, 2H), 8.68 (s, 2H), 8.41 (d, J=8.8 Hz, 2H), 8.07 (dd, J=8.5, 7.1 Hz, 1H), 7.94 (t, J=6.0 Hz, 4H), 7.79 (d, J=9.1 Hz, 2H), 7.49 (d, J=7.6 Hz, 4H), 7.36-7.27 (m, 4H), 7.03 (t, J=7.4 Hz, 2H). $^{13}$C NMR (151 MHz, DMSO-d6) δ 152.24, 144.51, 142.85, 139.39, 138.12, 130.28 (q, J=3.8 Hz), 129.36, 128.59, 127.61 (q, J=3.2 Hz), 124.30 (q, J=271.1 Hz), 123.01, 122.82 (q, J=32.6 Hz), 120.04, 119.05, 110.78, 95.39, 84.09.

Bis-Urea 4d:

Dianiline 8 (24.5 mg, 0.055 mmol) and pentafluorophenyl isocyanate (72 µL, 0.55 mmol) were reacted at 80° C. for 16 h using general procedure E. Purification using general procedure E afforded the desired product (40.3 mg, 75%). $^1$H NMR (600 MHz, DMSO-d6) δ 9.65 (s, 2H), 9.00 (s, 2H), 8.35 (d, J=8.9 Hz, 2H), 8.07 (t, J=7.8 Hz, 1H), 7.98 (d, J=1.5 Hz, 2H), 7.91 (d, J=7.8 Hz, 2H), 7.80 (dd, J=9.0, 1.6 Hz, 2H). $^{13}$C NMR (151 MHz, DMSO-d6) δ 151.41, 143.42, 143.65-141.64 (m), 142.34, 139.82-137.37 (m), 137.69, 137.23 (dt, J=32.1, 19.1 Hz), 129.97-129.74 (m, J=3.8 Hz), 128.14, 127.45-127.21 (m, J=3.5 Hz), 123.74 (q, J=271.2 Hz), 123.08 (q, J=33.6 Hz), 119.61, 113.12 (t, J=13.8 Hz), 110.85, 95.05, 83.40.

Bis-Urea 5a:

Dianiline 9 (116 mg, 0.314 mmol) and 4-methoxyphenyl isocyanate (121 µL, 0.94 mmol) were reacted at rt for 16 h using general procedure E. Purification using general procedure E afforded the desired product (133 g, 64%). $^1$H NMR (300 MHz, DMSO-d6) δ 9.17 (s, 2H), 8.15 (s, 2H), 8.04-7.95 (m, 1H), 7.92 (d, J=9.1 Hz, 2H), 7.80 (d, J=7.8 Hz, 2H), 7.36 (d, J=9.0 Hz, 4H), 7.13 (d, J=2.9 Hz, 2H), 7.04 (dd, J=9.1, 3.0 Hz, 2H), 6.86 (d, J=9.0 Hz, 4H), 3.77 (s, 6H), 3.71 (s, 6H). $^{13}$C NMR (151 MHz, DMSO-d6) δ 154.55, 154.18, 152.62, 142.70, 137.48, 134.32, 132.55, 127.42, 122.40, 120.14, 117.18, 116.19, 114.03, 112.03, 93.47, 85.47, 55.46, 55.14.

Bis-Urea 5b:

Dianiline 9 (214 mg, 0.58 mmol) and 4-nitrophenyl isocyanate (285 mg, 1.74 mmol) were reacted at rt for 16 h using general procedure E. Purification using general procedure E afforded the desired product (0.346 g, 86%). $^1$H NMR (300 MHz, DMSO-d6) δ 10.00 (s, 2H), 8.48 (s, 2H), 8.18 (d, J=9.2 Hz, 4H), 8.03-7.94 (m, 1H), 7.88 (d, J=9.1 Hz, 2H), 7.79 (d, J=7.8 Hz, 2H), 7.70 (d, J=9.2 Hz, 4H), 7.16 (d, J=2.9 Hz, 2H), 7.08 (dd, J=9.1, 2.9 Hz, 2H), 3.79 (s, 6H). $^{13}$C NMR (151 MHz, DMSO-d6) δ 154.95, 152.03, 146.23, 142.63, 141.08, 137.58, 133.20, 127.51, 125.16, 123.21, 117.51, 117.11, 116.47, 113.33, 93.49, 85.32, 55.52.

Bis-Urea 5c:

Dianiline 9 (36.3 mg, 0.098 mmol) and phenyl isocyanate (110 µL, 0.983 mmol) were reacted at rt for 16 h using general procedure E. Purification using general procedure E afforded the desired product (44.1 mg, 62%). $^1$H NMR (600 MHz, DMSO-d6) δ 9.30 (s, 2H), 8.24 (s, 2H), 7.98 (t, J=7.8 Hz, 1H), 7.91 (d, J=9.1 Hz, 2H), 7.80 (d, J=7.8 Hz, 2H), 7.51-7.42 (m, 4H), 7.28 (t, J=7.9 Hz, 4H), 7.14 (d, J=3.0 Hz, 2H), 7.05 (dd, J=9.1, 3.0 Hz, 2H), 6.97 (t, J=7.4 Hz, 2H), 3.78 (s, 6H). $^{13}$C NMR (151 MHz, DMSO-d6) δ 154.36, 152.46, 142.70, 139.58, 137.50, 134.06, 128.81, 127.45, 122.65, 121.93, 118.25, 117.17, 116.24, 112.34, 93.45, 85.45, 55.47.

Bis-Urea 5d:

Dianiline 9 (37 mg, 0.100 mmol) and pentafluorophenyl isocyanate (40 μL, 0.300 mmol) were reacted at rt for 16 h using general procedure E. Purification using general procedure E afforded the desired product (55.7 mg, 71%). $^1$H NMR (300 MHz, DMSO-d6) δ 9.19 (s, 2H), 8.58 (s, 2H), 8.08-7.95 (m, 1H), 7.85 (d, J=9.1 Hz, 2H), 7.79 (d, J=7.8 Hz, 2H), 7.16 (d, J=2.9 Hz, 2H), 7.05 (dd, J=9.1, 3.0 Hz, 2H), 3.78 (s, 6H). $^{13}$C NMR (151 MHz, DMSO-d6) δ 155.30, 152.36, 144.32-141.92 (m), 143.12, 139.90-137.47 (m), 137.95, 138.72-136.48 (m), 133.88, 127.90, 123.19, 117.57, 116.88, 114.25 (t, J=15.8 Hz), 113.53, 93.93, 85.67, 55.94.

Interestingly, the purification and characterization of some of these compounds proved problematic. First, the yields for reactions with 7 and 8 were in general considerably lower than those of their electron-rich counterparts, 6 and 9 (Table 2). This was anticipated since the aniline nitrogens on 7 and 8 should be less nucleophilic due to the presence of the para-substituted electron-withdrawing groups. However, these bisureas were accompanied by myriad side products, as revealed by TLC analysis. In the case of 4d, a small amount of a 2-quinazolinone derivative was isolated along with the desired bisurea.

TABLE 2

Yields for 2-5/a-d

|  | R | R' | Yield |
|---|---|---|---|
| 2a | t-Bu | 4-OMe | 93% |
| 2b | t-Bu | 4-NO$_2$ | 93% |
| 2c | t-Bu | H | 92% |
| 2d | t-Bu | 2,3,4,5,6-pentafluoro | 81% |
| 3a | CO$_2$Et | 4-OMe | 57% |
| 3b | CO$_2$Et | 4-NO$_2$ | 30% |
| 3c | CO$_2$Et | H | 26% |
| 3d | CO$_2$Et | 2,3,4,5,6-pentafluoro | 76% |
| 4a | CF$_3$ | 4-OMe | 16% |
| 4b | CF$_3$ | 4-NO$_2$ | 34% |
| 4c | CF$_3$ | H | 37% |
| 4d | CF$_3$ | 2,3,4,5,6-pentafluoro | 75% |
| 5a | OMe | 4-OMe | 64% |
| 5b | OMe | 4-NO$_2$ | 86% |
| 5c | OMe | H | 61% |
| 5d | OMe | 2,3,4,5,6-pentafluoro | 71% |

Second, the $^1$H NMR spectra of certain bis-ureas were unexpectedly complex. The most likely explanation of this phenomenon is aggregation in solution. This behavior was observed more often in scaffolds containing electron-withdrawing units at R and/or R', which is an indication that the urea pK$_a$s are lowered, leading to increased hydrogen bond donor ability. Clearly, protonation and addition of an anionic guest to 3d breaks up the self-association/aggregation, leading to the simplified $^1$H NMR spectrum; therefore, compounds 2-5/a-d were isolated as their corresponding trifluoroacetic acid (TFA) salts.

Another unusual problem was encountered while attempting to determine binding constants and stoichiometries of some of the bis-ureas with various tetrabutylammonium salts. During the course of the titration the $^1$H NMR spectra go from sharp and resolved prior to the addition of chloride to completely obscured at approximately 0.5 equiv. of chloride. At the half equivalent point visible aggregate is present in the NMR tube, but remarkably, upon further addition of chloride the host goes back into solution and the $^1$H NMR spectra resolve.

The most likely explanation for the observed phenomena is an equilibrium involving aggregation in solution. This behavior was observed more often in scaffolds containing electron-withdrawing units at R and/or R', which is an indication that when the urea pK$_a$s are lowered, hydrogen bond donor ability increases and aggregation increases. This phenomenon prevented the accurate determination of binding constants for this class of sensors, but it can clearly be seen that there is a strong propensity for these molecules to form complexes/aggregates in the presence of a suitable anionic guest.

This hypothesized self-aggregation in solution can also be observed in the x-ray crystal structure of 2b. In the solid-state a water molecule resides inside the molecular cavity of 2b, forming two intramolecular O—H•••N, N—H•••O and one intermolecular O—H•••O H-bonds. The molecules are also joined together by three N—H•••O H-bonds between the —NO$_2$ group in one molecule and NH groups in another one. In the crystal structure the molecules assemble into 1-D molecular strips that form layers perpendicular to the b axis. Even in a case of such complex molecular shape, all H atoms that can form H-bonds are involved in intra- and intermolecular H-bonds in the crystal structure, providing another example of the Hamilton rule.

With the library of compounds now in hand, the absorption and emission properties of the bisureas as well as those of the scaffold cores were examined. Given that an ideal anion sensor is one that is capable of functioning in polar media, such as DMSO, H$_2$O or CH$_3$CN, all UV-vis and fluorescence studies were performed in CH$_3$CN solutions. FIG. 1 shows the absorption spectra for the bis(arylethynyl)pyridines 6-9. Depending on the substituents attached to these cores a red or blue shift in absorption is observed. For example, the trifluoromethyl substituted core 8 has a blue-shifted absorbance compared to the tert-butyl substituted core 6, while the methoxy substituted core 9 is red-shifted. This same red and blue shifting behavior is seen in the corresponding emission spectra (FIG. 1). The electron-withdrawn cores are blue shifted and the electron rich cores are red shifted. One interesting phenomenon occurs in the case of the methoxy substituted core 9. It contains two distinct fluorescence bands, which are likely the result of dual emission from one species in solution.

The photoluminescence quantum yield (PLQY) for each of the four ethynylpyridines followed the trend in which the most electron rich cores had the lowest PLQY and the most electron poor cores had the highest PLQY (Table 3).

TABLE 3

PLQY and Stokes Shifts for 6-9 in MeCN

|  | R | Stokes Shift (cm$^{-1}$) | Quantum Yield |
|---|---|---|---|
| 6 | t-Bu | 5270 | 0.6% |
| 7 | CO$_2$Et | 4290 | 1.2% |
| 8 | CF$_3$ | 4090 | 1.1% |
| 9 | OMe | 2890, 3150 | 0.1% |

Figure 2:
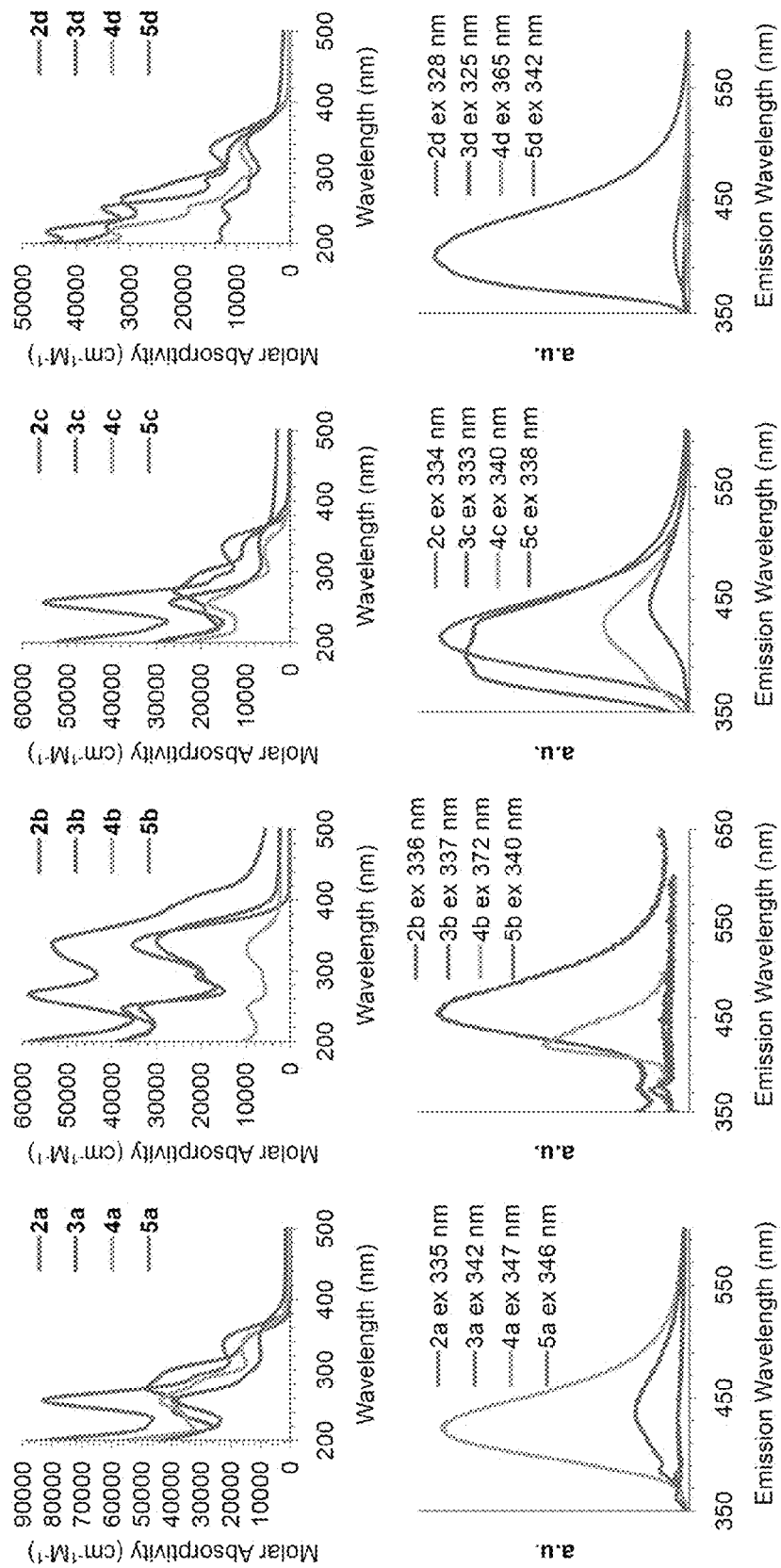
FIG. 2 shows electronic spectra of differentially substituted 2,6-ethynylpyridine bis-phenyl ureas 2a-5a (top left), 2b-5b (top middle-left), 2c-5c (top middle-right), and 2d-5d (top right) followed by fluorescence spectra of 2a-5a (bottom left), 2b-5b (bottom middle-left), 2c-5c (bottom middle-right), and 2d-5d (bottom right).

The neutral bis-ureas of each core were investigated in a similar manner. FIG. 2 shows the UV-Vis spectra for the tert-butyl derivatives 2a-d. Interestingly, the substituted phenyl ureas had virtually no effect on the resulting UV-Vis λ$_{max}$ indicating that the ethynthylpyridine cores are primarily responsible for the observed adsorption behaviour of the bisurea scaffolds.

The neutral bisurea scaffolds were also investigated with respect to their fluorescence, with careful attention paid to those scaffolds containing electron withdrawing R and R' groups (e.g. 3b, 3d, 4b, and 4d). Given that an ideal sensor is one that would go from an "off" state to an "on" state, we were primarily interested in electron withdrawn scaffolds that were non-emissive in their neutral state. Based on these criteria, compound 3d was further scrutinized with respect to their ability to sense chloride, whereas 4d was not studied further due to its tendency to decompose into the 2-quinazolinone biproduct.

Figure 3:
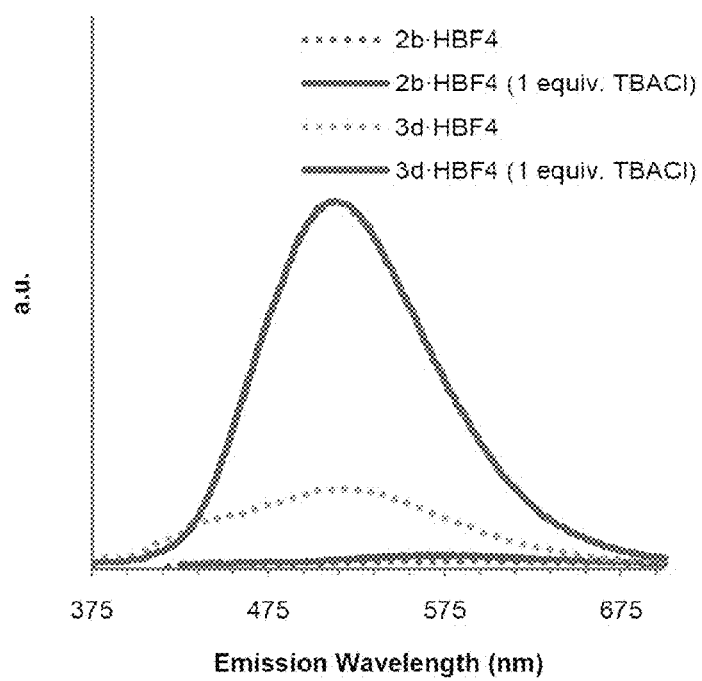
FIG. 3 shows emission spectra of 2b.$HBF_4$ and 3d.$HBF_4$ before addition of TBACl (dotted lines) and after addition of TBACl. Compound 2b.$HBF_4$ was excited at 416 nm, and compound 3d.$HBF_4$ was excited at 365 nm.

Compound 3d exhibits a fluorescence "off to on" response in the presence of chloride despite being in a polar MeCN solvent (FIG. 3). Although compound 3d is not soluble in water, these results provide evidence that this particular ethynthylpyridine scaffold can be tuned to exhibit a fluorescence response even in the presence of a highly competitive/polar solvent. Further studies will focus on determining the exact cause of this fluorescence and will aim to exhibit this same response in an aqueous solvent system.

The inherently fluorescent ethynthylpyridine scaffolds presented herein can be tuned to exhibit either a red or blue shifted fluorescence response depending on the electron donating or withdrawing ability of the pendant functional groups. Similarly, the hydrogen bonding behavior of the bisurea scaffolds is highly dependent on the pendant functional groups. NMR spectroscopic and solid state structural studies indicate that without a suitable guest these receptors hydrogen bond strongly with themselves, suggesting that these sensors could allow for larger binding constants for anionic guests and potentially greater selectivity. The derivatization of this class of receptors allows for a "turn-on" fluorescence response to analytes in increasingly polar solvents, a feature often lacking in small molecule organic anion probes.

Example 18

The synthesis of additional host compounds is shown below:

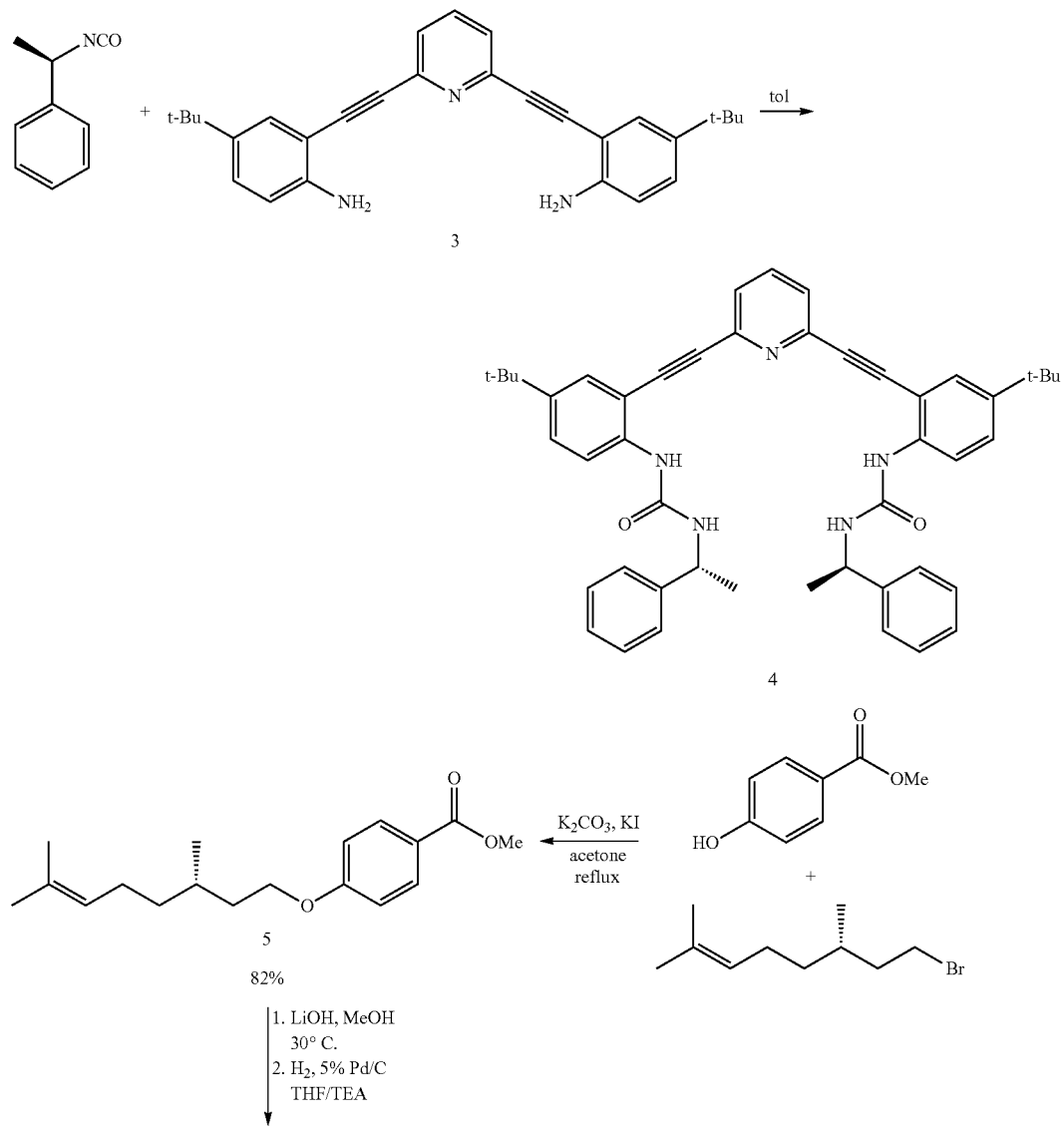

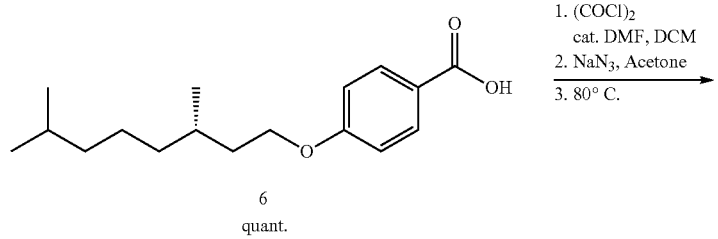
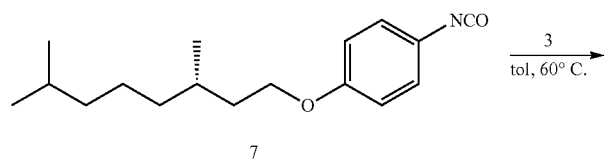
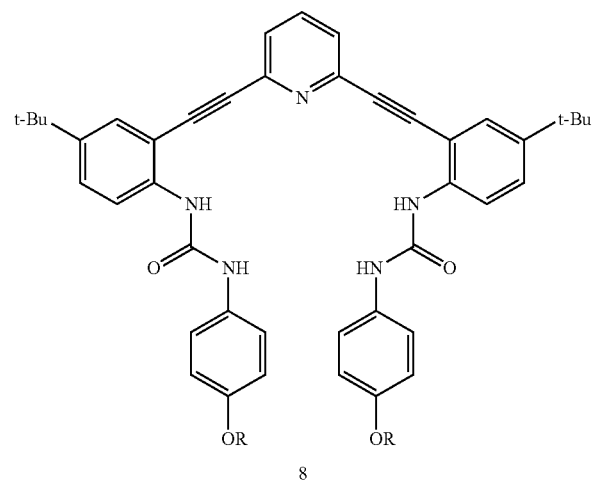
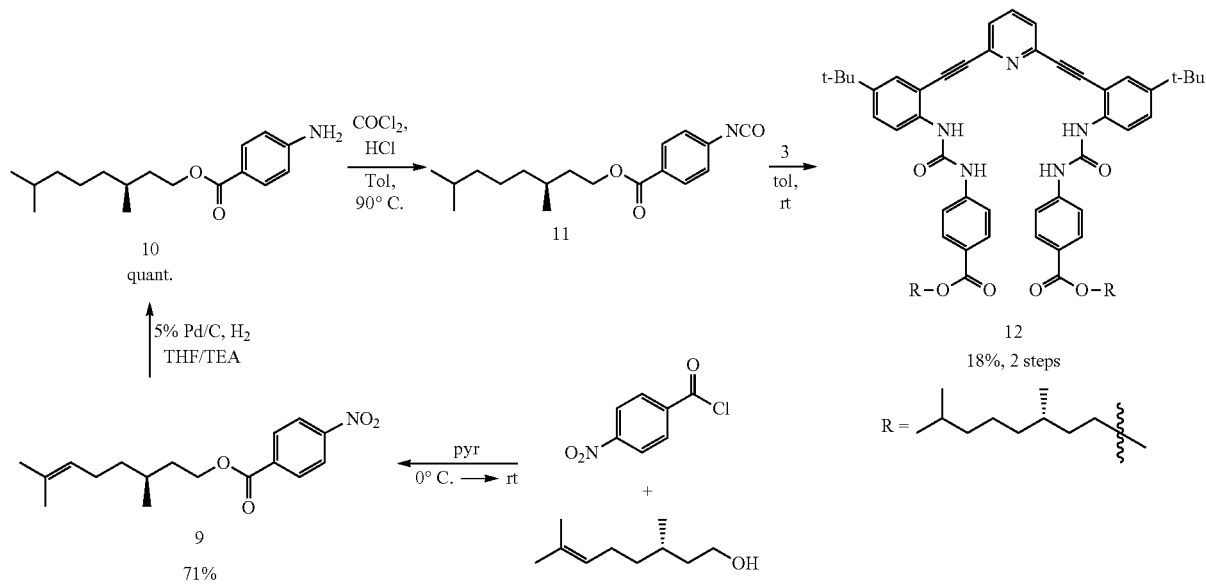

-continued
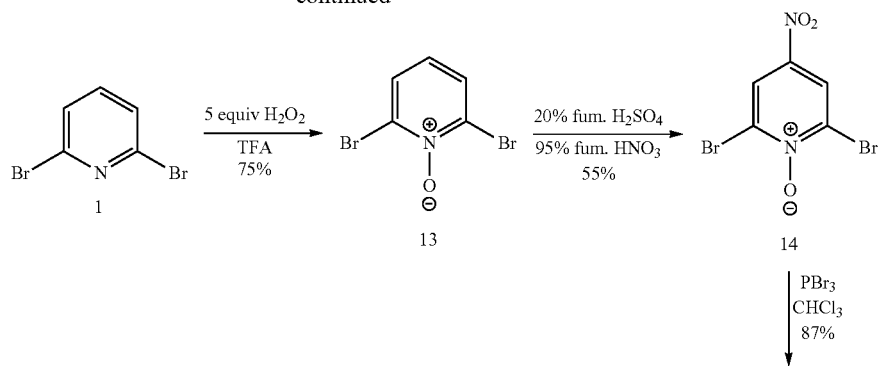
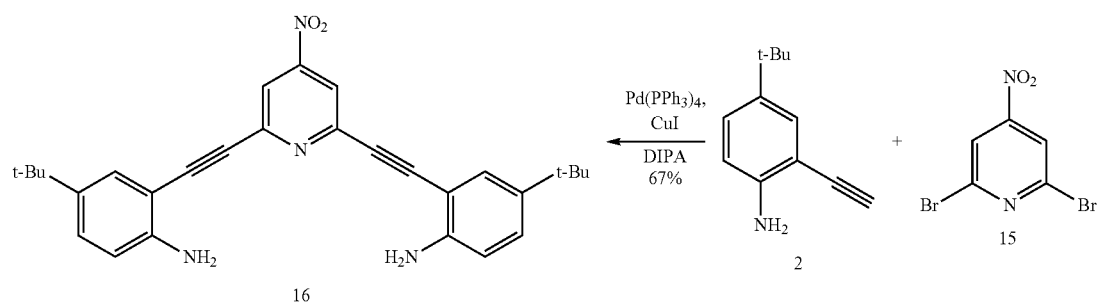
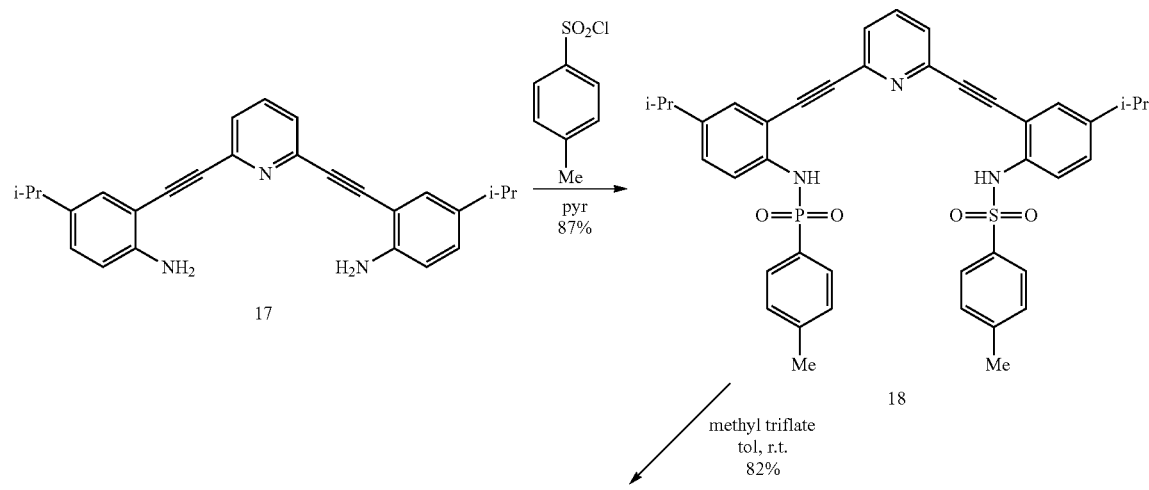

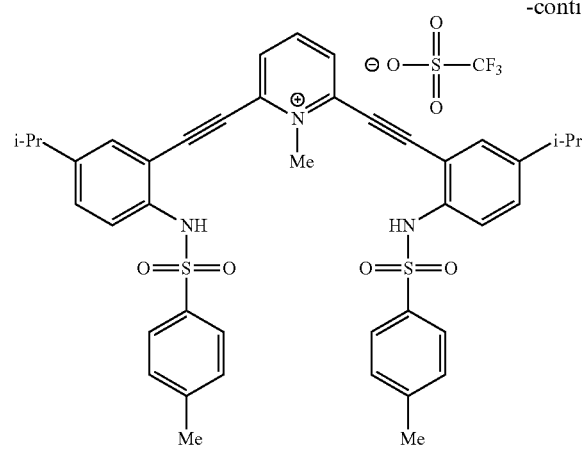
19
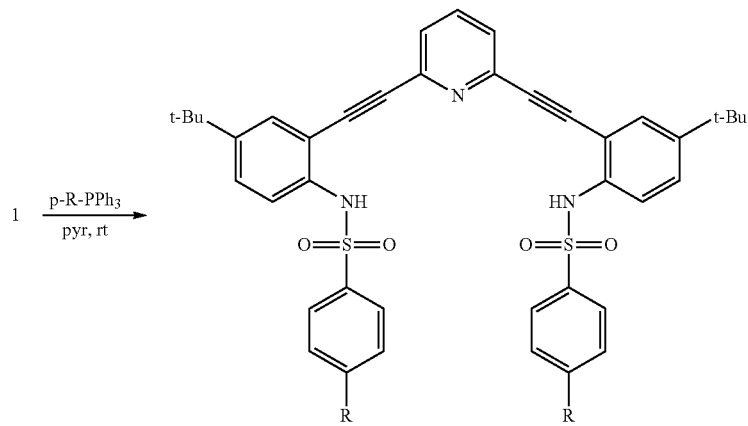
2e R = Bu, 98%
2f R = Oct, 96%
Scheme 2. Alternative Synthesis of Water Soluble Receptor.
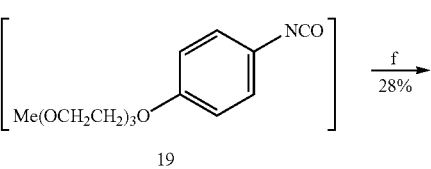
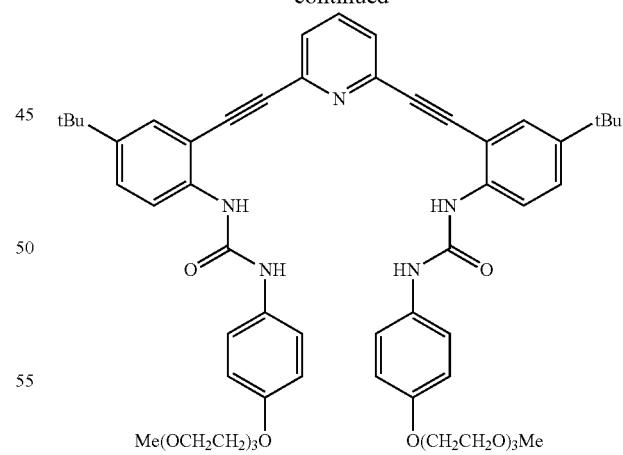
20
Reagents and Conditions: (a) NaOH, H$_2$O, THF; (b) TsCl, Et$_3$N, THF; (c) 4-nitrophenol, K$_2$CO$_3$, DMF; (d) H$_2$, Pd/C, EtOH, HCl; (e) Triphosgene, DCM, NaHCO$_3$; (f) t-Bu analog of 10, toluene.

Scheme 3. Synthesis of New Dianiline Core.

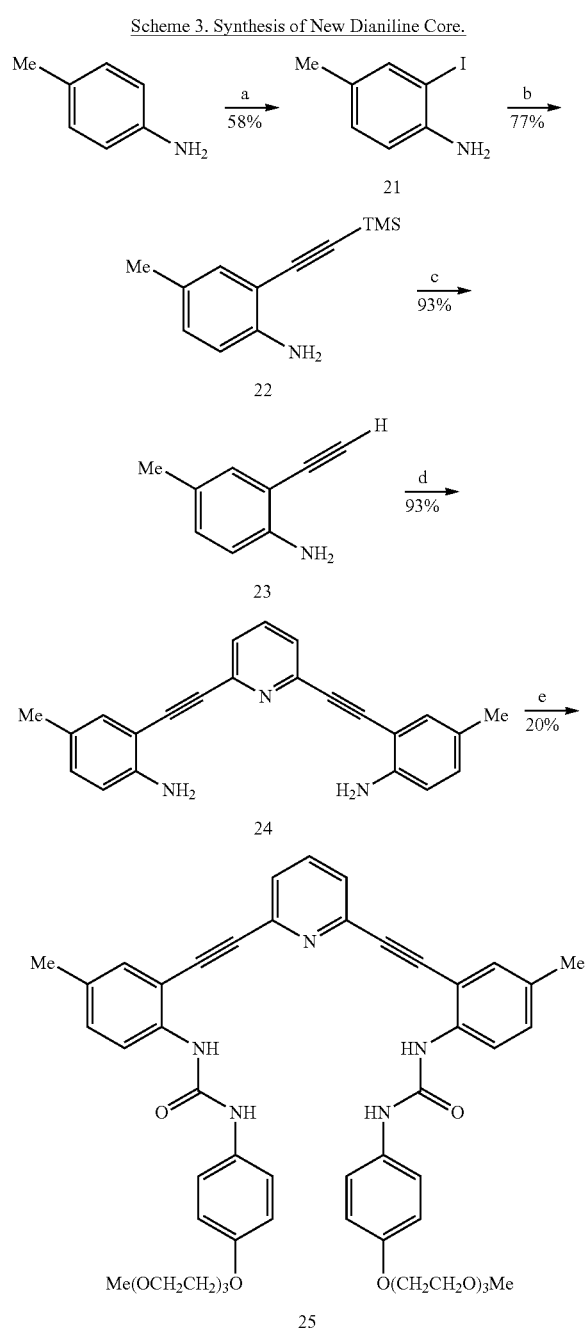

Reagents and Conditions: (a) BTEA·ICl₂, CaCO₃, CHCl₃, MeOH; (b) TMSA, PdCl₂(PPh₃)₂, CuI, THF, DIPA; (c) K₂CO₃, MeOH, Et₂O; (d) 2,6-dibromopyridine, Pd(PPh₃)₄, CuI, THF, DIPA; (e) 19, PhMe, TEA.

Scheme 4. Synthesis of bis-pentaethylene glycol derivative.

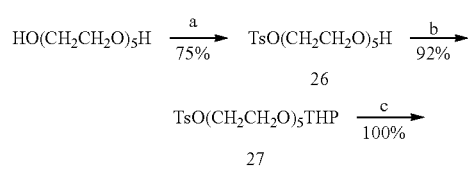

-continued

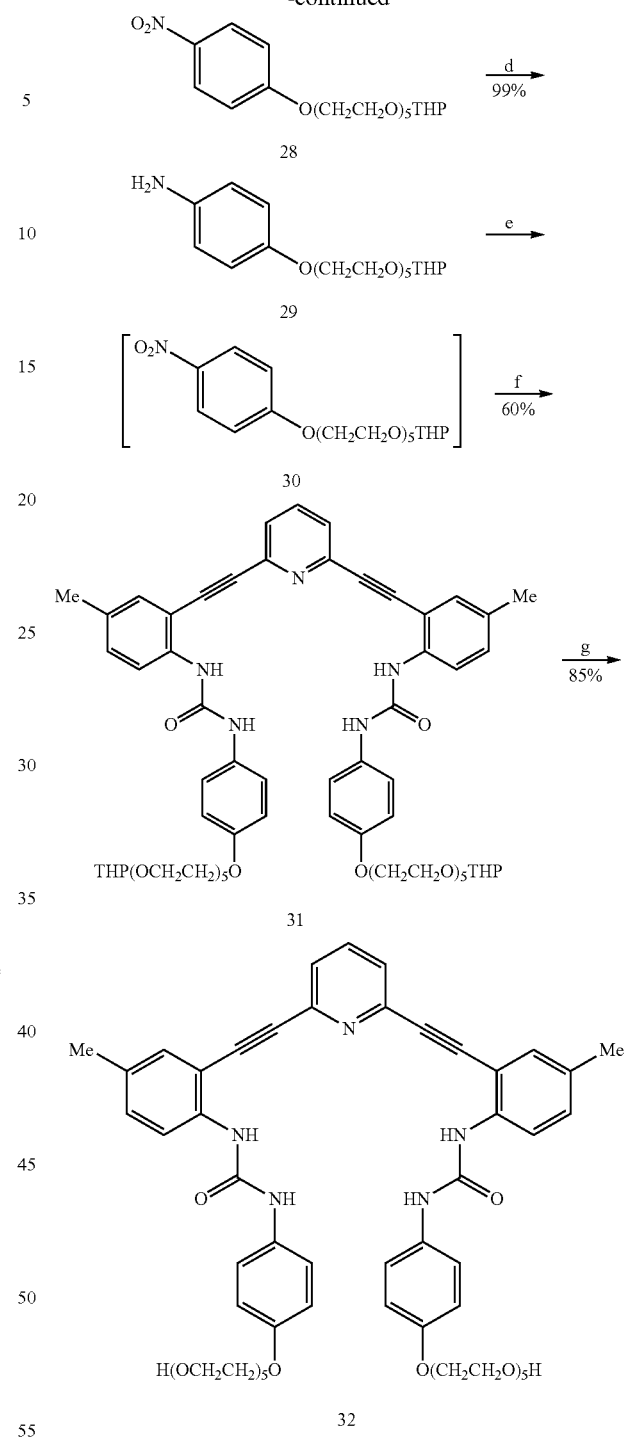

Reagents and Conditions: (a) TsCl, Ag₂O, KI, DCM; (b) DHP, PPTS, DCM; (c) 4-Nitrophenol, K₂CO₃, DMF; (d) H₂, Pd/C, THF, TEA; (e) Phosgene, PhMe, TEA; (f) 24, PhMe; (g) HCl, MeOH, DCM Scheme 5. Attempted synthesis of hexaethylene glycol derivative.

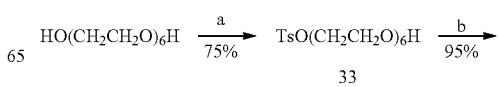

-continued

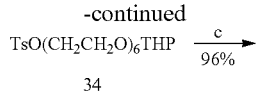
34

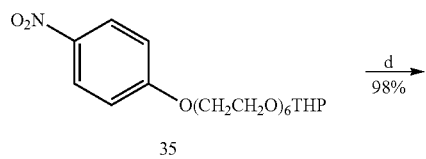
35

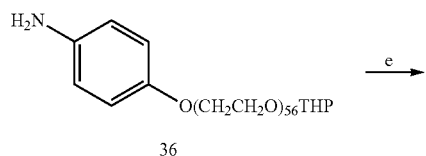
36

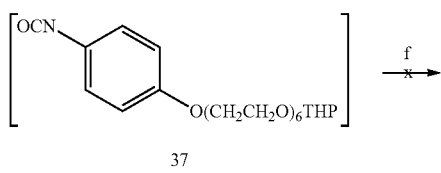
37

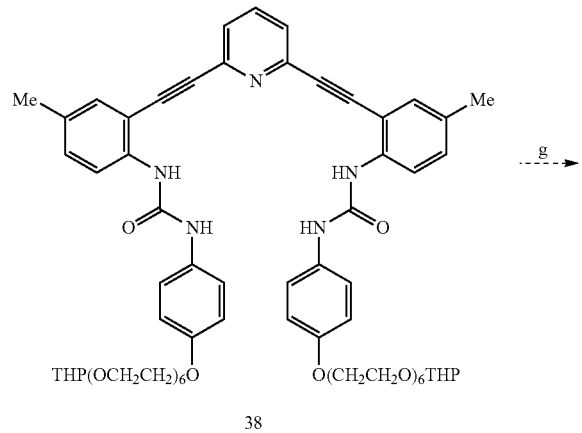
38

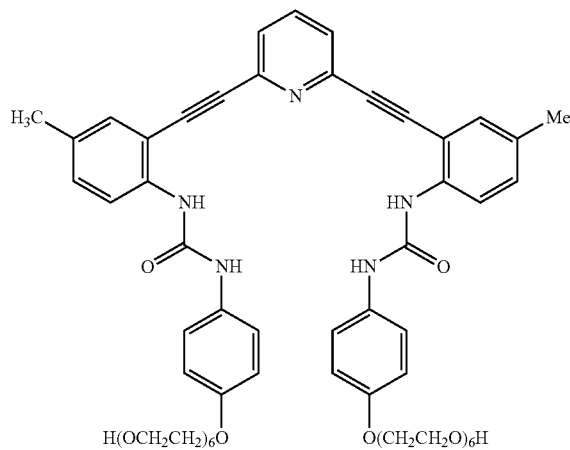
39

Reagents and Conditions: (a) TsCl, Ag₂O, KI, DCM; (b) DHP, PPTS, DCM; (c) 4-Nitrophenol, K₂CO₃, DMF; (d) H₂, Pd/C, THF, TEA; (e) Phosgene, PhMe, TEA; (f) 24, PhMe; (g) HCl, MeOH, DCM Scheme 9. Synthesis of ethynylarene based redox sensors.

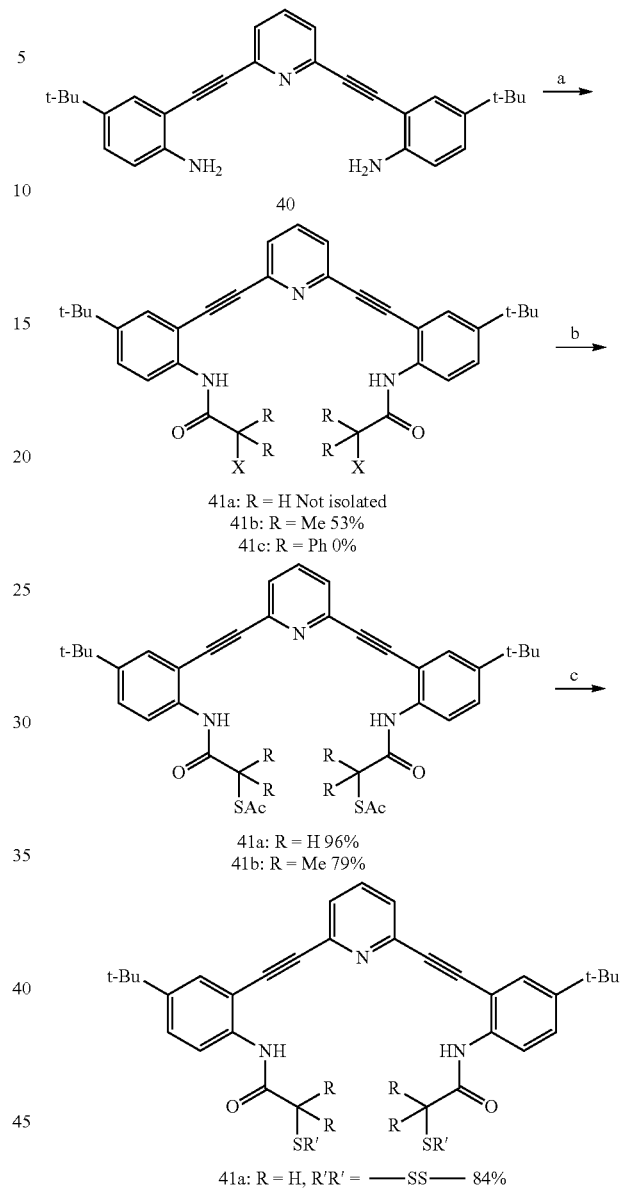

Reagents and Conditions: (a) α–haloacyl halide, DCM, TEA; (b) KSAc, DMF; (c) K₂CO₃, MeOH

2-(2-(2-Methoxyethoxy)ethoxy)ethyl 4-methylbenzenesulfonate (16)

To a solution of NaOH (1.69 g, 42.2 mmol) in H₂O (11 mL) was added a solution of triethylene glycol monomethyl ether (5.00 mL, 31.9 mmol) in THF (11 mL) under nitrogen, while the temperature was maintained below 5° C. by cooling with an ice-salt bath. At the same temperature, a solution of p-toluenesulfonyl chloride (6.08 g, 31.9 mmol) in THF (13 mL) was added dropwise over 1 h. The reaction mixture was poured into water and DCM was added. The layers were separated, and the aqueous layer was extracted with DCM (three times). The combined organic layers were washed with water (twice) and brine (twice), dried over anhydrous MgSO₄, filtered off and evaporated to dryness to give 16 (8.43 g, 83%): $^1$H NMR (300 MHz, CDCl$_3$) δ 7.75 (d, J=8.3 Hz, 2H), 7.30 (d, J=8.2 Hz, 2H), 4.16 (t, 2H), 3.50-3.70 (m, 10H), 3.32 (s, 3H), 2.40 (s, 3H).

1-(2-(2-(2-Methoxyethoxy)ethoxy)ethoxy)-4-nitrobenzene (17)

To a stirred solution of 16 (1.83 g, 5.75 mmol) in anhydrous DMF (10 mL) were added K$_2$CO$_3$ (2.39 g, 17.3 mmol) and 4-nitrophenol (0.78 g, 5.59 mmol), and the reaction mixture was heated to 80° C. for 16 h. After cooling, the mixture was diluted in water, extracted three times with DCM, and then dried over MgSO$_4$. The filtrate was concentrated under reduced pressure to give an oily residue, which was purified by flash chromatography over silica gel with Hex/EtOAc (1:2) to afford 17 as a yellow oil (1.51 g, 92%): $^1$H NMR (500 MHz, CDCl$_3$) δ 8.19 (d, J=9.1 Hz, 2H), 6.97 (d, J=9.1 Hz, 2H), 4.26-3.65 (m, 12H), 3.37 (s, 3H).

4-(2-(2-(2-Methoxyethoxy)ethoxy)ethoxy)aniline (18)

To a stirred solution of 17 (1.39 g, 4.86 mmol) in acidic EtOH (5 mL) in a Parr apparatus was added a catalytic amount of 20% Pd/C (0.05 g). The reaction vessel was purged with H$_2$ then pressurized to 70 psi. After stirring for 16 h the reaction mixture was filtered through a 4 cm pad of celite and concentrated under reduced pressure to afford 18 as a brown oil (1.24 g, 100%): $^1$H NMR (300 MHz, CDCl$_3$) δ 6.75 (d, J=8.8 Hz, 2H), 6.62 (d, J=8.8 Hz, 2H), 4.11-3.99 (m, 2H), 3.87-3.78 (m, 2H), 3.76-3.51 (m, 8H), 3.42 (s, 1H), 3.38 (s, 2H).

1-Isocyanato-4-(2-(2-(2-methoxyethoxy)ethoxy)ethoxy)benzene (19)

To a stirred 0° C. solution of 18 (0.59 g, 2.29 mmol) in DCM (23 mL) was added a 20% phosgene/toluene solution (2.42 mL). After stirring for 3 h the reaction mixture was concentrated under reduced pressure and carried on without further purification.

Receptor 20

To a stirred solution of 2,2'-(pyridine-2,6-diylbis(ethyne-2,1-diyl))bis(4-tert-butylaniline) (0.18 g, 0.43 mmol) in dry PhMe (8.49 mL) was added a 0.57 M solution of 19 (0.36 g, 1.27 mmol) at room temperature. After stirring for 16 h the reaction mixture was concentrated under reduced pressure and the crude product was purified by flash chromatography over silica gel with EtOAc/DCM (4:1) to give 20 as a brown oil (0.116 g, 28%): $^1$H NMR (300 MHz, DMSO) δ 9.29 (s, 2H), 8.23 (s, 2H), 8.00 (m, 3H), 7.81 (d, J=7.4 Hz, 2H), 7.53 (d, J=2.2 Hz, 2H), 7.47 (dd, J=8.6, 2.1 Hz, 2H), 7.37 (d, J=8.9 Hz, 4H), 6.88 (d, J=8.9 Hz, 4H), 3.99-4.12 (m, 4H), 3.69-3.80 (m, 4H), 3.62-3.38 (m, 16H), 3.23 (s, 6H), 1.29 (s, 18H).

2-Iodo-4-Methylaniline (21)

To a stirred solution of p-toluidine (14.10 g, 132 mmol) in 5:1 CHCl$_3$/MeOH (1000 mL) were added CaCO$_3$ (19.8 g, 197 mmol) and BTEA.Cl$_2$ (59.06 g, 151 mmol) at room temperature. After stirring for 3 h, the reaction mixture was washed thrice with a solution of NaHSO$_3$ (5% w/v) and once with water. The organic layer was dried over MgSO$_4$ and subsequently filtered. The filtrate was concentrated under reduced pressure to give 27 as a yellow powder (17.42 g, 57%): $^1$H NMR (300 MHz, CDCl$_3$) δ 7.47 (d, J=1.2 Hz, 1H), 6.95 (dd, J=8.1, 1.2 Hz, 1H), 6.66 (d, J=8.1 Hz, 1H), 3.95 (s, 2H), 2.21 (s, 3H).

4-Methyl-2-((trimethylsilyl)ethynyl)aniline (22)

To a stirred degassed solution 21 (17.42 g, 74.7 mmol) in 1:1 THF/DIPA (500 mL) were added CuI (0.71 g, 3.74 mmol) and PdCl$_2$(PPh$_3$)$_2$ (1.57 g, 2.24 mmol) at room temperature. The solution was degassed with argon for an additional 30 min after which TMSA (20.7 mL, 149 mmol) was added. The vessel was sealed under inert atmosphere and heated to 50° C. After stirring for 6 h, the reaction mixture was cooled, diluted with CH$_2$Cl$_2$, and filtered through a 4 cm pad of silica. The filtrate was concentrated under reduced pressure to afford an dark brown solid, which was purified by flash chromatography over silica gel with Hex/EtOAc (19:1) to give 22 as a light brown solid (11.73 g, 77%): $^1$H NMR (300 MHz, CDCl$_3$) δ 7.12 (d, J=1.5 Hz, 1H), 6.93 (dd, J=8.2, 1.5 Hz, 1H), 6.60 (d, J=8.2 Hz, 1H), 4.09 (s, 2H), 2.19 (s, 3H), 0.26 (s, 9H).

2-Ethynyl-4-methylaniline (23)

To a stirred solution of 22 (11.32 g, 55.6 mmol) in 2:1 MeOH/Et$_2$O (250 mL) was added K$_2$CO$_3$ (15.38 g, 111 mmol) at room temperature. After stirring for 1 h at this temperature, the reaction mixture was diluted with water and extracted with CH$_2$Cl$_2$. The organic layer was dried over MgSO$_4$, filtered and concentrated under reduced pressure to give 23 as a light brown solid without the need for purification (6.79 g, 93%): $^1$H NMR (300 MHz, CDCl$_3$) δ 7.14 (d, J=1.5 Hz, 1H), 6.96 (dd, J=8.2, 1.5 Hz, 1H), 6.62 (d, J=8.2 Hz, 1H), 4.11 (s, 2H), 3.36 (s, 1H), 2.21 (s, 3H).

Dianiline 24

To a stirred degassed solution of 2,6-dibromopyridine (5.58 g, 23.5 mmol) in 1:1 THF/DIPA (470 mL) were added CuI (0.45 g, 2.38 mmol) and Pd(PPh$_3$)$_4$ (1.38 g, 1.19 mmol) at room temperature. The solution was degassed with argon for an additional 30 min and then heated to 50° C. To this solution a second degassed solution of 22 (6.79 g, 51.8 mmol) in THF (20 mL) was added dropwise over 12 h. After stirring for 16 h, the reaction mixture was cooled, diluted with CH$_2$Cl$_2$, and filtered through a 4 cm pad of silica. The filtrate was concentrated under reduced pressure to give a dark brown solid. The crude product was then dissolved in EtOAc and triturated with hexanes until cloudy. The resulting suspension was cooled in an ice bath for 1 h and the solid product 24 was filtered and dried (7.35 g, 93%): $^1$H NMR (500 MHz, CDCl$_3$) δ 7.68 (t, J=7.8 Hz, 1H), 7.45 (d, J=7.8 Hz, 2H), 7.28 (s, 2H), 7.26 (s, 2H), 7.01 (d, J=8.2 Hz, 2H), 6.67 (d, J=8.2 Hz, 2H), 4.29 (s, 4H), 2.25 (s, 6H). $^{13}$C NMR (126 MHz, CDCl$_3$) δ 146.36, 143.96, 136.36, 132.69, 131.57, 127.08, 125.84, 114.63, 106.46, 93.46, 87.12, 20.24.

Receptor 25

To a stirred solution 24 (0.25 g, 0.74 mmol) in dry PhMe (15 mL) was added a 20 mL solution of 19 (0.63 g, 2.22 mmol) in PhMe at room temperature. After stirring for 16 h the reaction mixture was concentrated under reduced pressure to give a brown oil. The crude product was purified by flash chromatography over silica gel with EtOAc/DCM (4:1) to give 25 as a brown oil (0.135 g, 20%): $^1$H NMR (300 MHz, DMSO) δ 9.28 (s, 2H), 8.21 (s, 2H), 8.03-7.93 (m, 3H), 7.79

(d, J=7.8 Hz, 2H), 7.39 (s, 2H), 7.36 (d, J=9.1 Hz, 4H), 7.23 (d, J=6.8 Hz, 2H), 6.89 (d, J=9.1 Hz, 4H), 4.11-3.94 (m, 4H), 3.78-3.65 (m, 4H), 3.62-3.39 (m, 16H), 3.23 (s, 6H), 2.27 (s, 6H).

14-Hydroxy-3,6,9,12-tetraoxatetradecyl 4-methylbenzenesulfonate (26)

To a chilled (0° C.) solution of pentaethylene glycol (2.13 g, 8.92 mmol) in DCM (89 mL) were added TsCl (1.87 g, 9.81 mmol), $Ag_2O$ (3.10 g, 0.134 mmol), and KI (0.296 g, 1.78 mmol). After stirring for 20 min the reaction mixture was filtered through a 4 cm pad of celite and flushed with EtOAc. The resulted filtrate was concentrated under reduced pressure to give a yellow oil. The crude product was purified via silica flash chromatography using 3:2 DCM/acetone as an eluent, providing 26 (2.63 g, 75%): $^1$H NMR (300 MHz, $CDCl_3$) δ 7.80 (d, J=8.2 Hz, 2H), 7.34 (d, J=8.2 Hz, 2H), 4.20-4.11 (m, 2H), 3.76-3.54 (m, 18H), 2.44 (s, 3H).

14-(Tetrahydro-2H-pyran-2-yloxy)-3,6,9,12-tetraoxatetradecyl 4-methylbenzenesulfonate (27)

To a solution of 26 (2.613 g, 6.66 mmol) in DCM (100 mL) were added pyridinium p-toluenesulfonate (0.335 g, 1.33 mmol) and 2,3-dihydro-2H-pyran (0.91 mL, 9.99 mmol). The resulting mixture was refluxed for 3 h. After cooling the solution was concentrated under vacuum, poured into ice-water, and extracted with DCM. The combined organic layers were washed with water and brine, dried over $MgSO_4$, filtered, and concentrated to give a yellow oil. The crude product was purified via silica flash chromatography using 4:1 EtOAc/Hex as an eluent, furnishing 27 (2.91 g, 92%): $^1$H NMR (300 MHz, $CDCl_3$) δ 7.79 (d, J=8.2 Hz, 2H), 7.33 (d, J=8.2 Hz, 2H), 4.67-4.57 (m, 1H), 4.19-4.11 (m, 2H), 3.93-3.78 (m, 2H), 3.71-3.54 (m, 18H), 2.44 (s, 3H), 1.92-1.41 (m, 6H).

2-(14-(4-Nitrophenoxy)-3,6,9,12-tetraoxatetradecyloxy)tetrahydro-2H-pyran (28)

To a stirred solution of 27 (2.90 g, 6.09 mmol) in anhydrous DMF (11 mL) were added $K_2CO_3$ (2.53 g, 18.3 mmol) and 4-nitrophenol (0.847 g, 6.09 mmol), and the reaction mixture was heated to 80° C. for 16 h. After cooling, the reaction mixture was diluted in water, extracted three times with $CH_2Cl_2$, and then dried over $MgSO_4$. The filtrate was concentrated under reduced pressure to give 28 as an oily residue (2.65 g, 98%): $^1$H NMR (300 MHz, $CDCl_3$) δ 8.18 (d, J=9.2 Hz, 2H), 6.99 (d, J=9.2 Hz, 2H), 4.69-4.56 (m, 1H), 4.28-4.17 (m, 2H), 3.97-3.42 (m, 18H), 1.95-1.41 (m, 6H). $^{13}$C NMR (75 MHz, $CDCl_3$) δ 163.82, 141.40, 125.75, 114.52, 98.83, 70.81, 70.51, 70.43, 69.27, 68.15, 66.54, 62.12, 30.48, 25.34, 19.41.

4-(14-(Tetrahydro-2H-pyran-2-yloxy)-3,6,9,12-tetraoxatetradecyloxy)aniline (29)

To a stirred solution of 28 (2.600 g, 5.86 mmol) in 1:1 THF/TEA (11 mL) in a Parr apparatus was added a catalytic amount of 20% Pd/C (0.05 g). The reaction vessel was purged with $H_2$ then pressurized to 70 psi. After stirring for 16 h the reaction mixture was filtered through a 4 cm pad of celite and concentrated under reduced pressure to afford 27 as a brown oil (2.44 g, 100%): $^1$H NMR (300 MHz, $CDCl_3$) δ 6.67 (d, J=8.8 Hz, 2H), 6.56 (d, J=8.8 Hz, 2H), 4.56 (m, 1H), 3.97 (t, J=4.8 Hz, 2H), 3.88-3.33 (m, 20H), 1.89-1.37 (m, 6H).

2-(14-(4-Isocyanatophenoxy)-3,6,9,12-tetraoxatetradecyloxy)tetrahydro-2H-pyran (30)

To a stirred 0° C. solution of 29 (0.95 g, 2.30 mmol) in 5:1 DCM/TEA (30 mL) was added a 20% phosgene/toluene solution (2.43 mL, 4.59 mmol). After stirring for 3 h the reaction was concentrated under reduced pressure and carried on without further purification.

Receptor 31

To a stirred solution of 24 (0.258 g, 0.765 mmol) in dry PhMe (25 mL) was added 30 (1.008 g, 2.29 mmol) at room temperature. After stirring for 16 h the reaction mixture was concentrated under reduced pressure to give a brown oil. The crude product was purified by flash chromatography over silica gel with DCM/MeOH (19:1) to give 31 as a yellow oil (0.556 g, 60%): $^1$H NMR (300 MHz, DMSO) δ 9.27 (s, 2H), 8.20 (s, 2H), 7.98 (m, 3H), 7.78 (d, J=7.8 Hz, 2H), 7.39 (s, 2H), 7.36 (d, J=9.0 Hz, 4H), 7.24 (d, J=8.6 Hz, 2H), 6.88 (d, J=8.9 Hz, 4H), 4.56 (m, 2H), 3.97 (t, J=4.8 Hz, 4H), 3.88-3.33 (m, 36H), 2.27 (s, 6H), 1.89-1.37 (m, 12H).

Receptor 32

To a stirred solution of 31 (0.556 g, 0.457 mmol) in 1:1 MeOH/DCM (25 mL) was added conc. HCl (0.0833 g, 2.29 mmol) at room temperature. After stirring for 2 h the reaction mixture was quenched with $NaHCO_3$ and then diluted with water. The resulting solution was extracted twice with DCM and the organic layers were concentrated under reduced pressure to give a brown oil. The crude product was purified by flash chromatography over silica gel with DCM/MeOH (93:7) to give 32 as a yellow oil (0.405 g, 85%): $^1$H NMR (300 MHz, DMSO) δ 9.28 (s, 2H), 8.21 (s, 2H), 8.09-7.90 (m, 3H), 7.79 (d, J=7.8 Hz, 2H), 7.39 (s, 2H), 7.36 (d, J=9.0 Hz, 4H), 7.24 (d, J=8.6 Hz, 2H), 6.88 (d, J=8.9 Hz, 4H), 4.59 (t, J=5.4 Hz, 2H), 4.18-3.95 (m, 4H), 3.81-3.66 (m, 4H), 3.65-3.37 (m, 32H), 2.27 (s, 6H). $^{13}$C NMR (126 MHz, DMSO) δ 153.81, 152.38, 142.80, 138.48, 132.52, 131.17, 127.19, 120.20, 114.67, 110.33, 93.64, 85.52, 72.33, 70.01, 69.79, 69.45, 69.00, 67.26, 60.20. Calc. MS for $C_{57}H_{69}N_5O_{14}+Na^+$ =1070.47, found 1070.4.

17-Hydroxy-3,6,9,12,15-pentaoxaheptadecyl 4-methylbenzenesulfonate (33)

To a chilled (0° C.) solution of hexaethylene glycol (5.41 g, 19.2 mmol) in DCM (191 mL) were added TsCl (4.02 g, 21.1 mmol), $Ag_2O$ (6.67 g, 28.8 mmol), and KI (0.64 g, 3.84 mmol). After stirring for 20 min the reaction mixture was filtered through a 4 cm pad of celite and flushed with EtOAc. The resulted filtrate was concentrated under reduced pressure to give a yellow oil. The crude product was purified via silica flash chromatography using 3:2 DCM/Acetone as an eluent, providing 33 (6.24 g, 75%): $^1$H NMR (300 MHz, $CDCl_3$) δ 7.79 (d, J=8.2 Hz, 2H), 7.33 (d, J=8.2 Hz, 2H), 4.23-4.07 (m, 2H), 3.82-3.51 (m, 22H), 2.55 (d, J=6.0 Hz, 1H), 2.44 (s, 3H).

17-(Tetrahydro-2H-pyran-2-yloxy)-3,6,9,12,15-pentaoxaheptadecyl 4-methylbenzenesulfonate (34)

To a solution of 33 (6.24 g, 14.3 mmol) in DCM (215 mL) were added pyridinium p-toluenesulfonate (0.72 g, 2.86 mmol), and 2,3-dihydro-2H-pyran (1.96 mL, 21.5 mmol). The resulting mixture was refluxed for 3 h. After cooling, the solution was concentrated under reduced pressure, poured into ice-water, and extracted with DCM. The combined organic layers were washed with water and brine, dried over MgSO4, filtered, and concentrated to give 34 as a yellow oil (7.08 g, 95%): $^1$H NMR (300 MHz, CDCl$_3$) δ 7.79 (d, J=8.3 Hz, 2H), 7.34 (d, J=8.0 Hz, 2H), 4.67-4.57 (m, 1H), 4.18-4.13 (m, 2H), 3.86 (m, 2H), 3.72-3.44 (m, 22H), 2.44 (s, 3H), 1.91-1.43 (m, 6H).

2-(17-(4-Nitrophenoxy)-3,6,9,12,15-pentaoxaheptadecyloxy)tetrahydro-2H-pyran (35)

To a stirred solution of 34 (7.03 g, 13.5 mmol) in anhydrous DMF (24 mL) were added K$_2$CO$_3$ (5.60 g, 40.5 mmol), and 4-nitrophenol (1.88 g, 13.5 mmol). The reaction mixture was heated to 80° C. for 16 h. Upon completion, the reaction mixture was diluted in water, extracted three times with CH$_2$Cl$_2$, and then dried over MgSO$_4$. The filtrate was concentrated under reduced pressure to give an oily residue, which provided 35 as a yellow oil without further purification (6.30 g, 96%): $^1$H NMR (300 MHz, CDCl$_3$) δ 8.19 (d, J=9.3 Hz, 2H), 6.97 (d, J=9.3 Hz, 2H), 4.67-4.57 (m, 1H), 4.26-4.17 (m, 2H), 3.95-3.79 (m, 2H), 3.78-3.34 (m, 22H), 1.47-1.84 (m, 6H).

4-(17-(Tetrahydro-2H-pyran-2-yloxy)-3,6,9,12,15-pentaoxaheptadecyloxy)aniline (36)

To a stirred solution of 35 (6.30 g, 12.9 mmol) in 1:1 THF/TEA (26 mL) in a Parr apparatus was added a catalytic amount of 20% Pd/C (0.05 g). The reaction vessel was purged with hydrogen then pressurized to 70 psi. After stirring for 16 h the reaction mixture was filtered through a 4 cm pad of celite and concentrated under reduced pressure to afford 36 as a brown oil (5.80 g, 98%): $^1$H NMR (300 MHz, CDCl$_3$) δ 6.75 (d, J=8.9 Hz, 2H), 6.62 (d, J=8.9 Hz, 2H), 4.71-4.55 (m, 1H), 4.09-4.00 (m, 2H), 3.94-3.31 (m, 22H), 1.93-1.44 (m, 6H).

In view of the many possible embodiments to which the principles of the disclosed materials, compositions and methods may be applied, it should be recognized that the illustrated embodiments are only preferred examples and should not be taken as limiting the scope of the invention.

What is claimed is:

1. A compound, or a salt thereof, having the formula

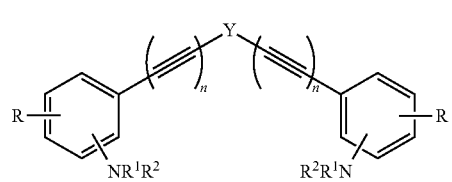

Formula III wherein Y is

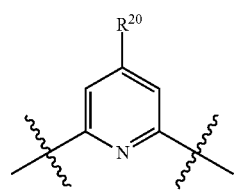

n is 1 or 2;
each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

R$^1$ is H, lower alkyl or aralkyl;

R$^2$ is selected from H, acyl, aralkyl, phosphonyl, —SO$_2$R$^3$; —C(O)R$^5$; —C(O)OR$^7$ or —C(O)NR$^9$R$^{10}$;

R$^3$; R$^5$; R$^7$; R$^9$ and R$^{10}$ independently are selected from H, lower alkyl, aralkyl or aryl; and R$^{20}$ is selected from alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

2. A compound, or a salt thereof, having the formula

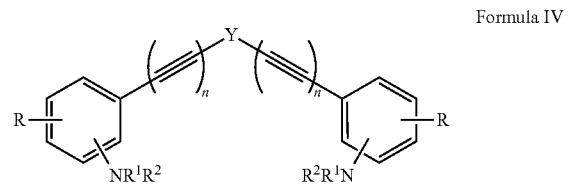

Formula IV wherein Y is selected from

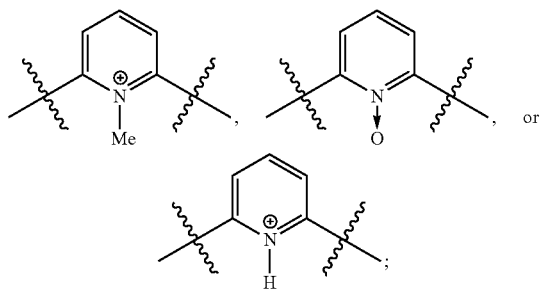

n is 1 or 2;

each R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

R$^1$ is H, lower alkyl or aralkyl;

R$^2$ is selected from H, acyl, aralkyl, phosphonyl, —SO$_2$R$^3$; —C(O)R$^5$; —C(O)OR$^7$ or —C(O)NR$^9$R$^{10}$;

R$^3$; R$^5$; R$^7$; R$^9$ and R$^{10}$ independently are selected from H, lower alkyl, aralkyl or aryl.

3. A compound, or a salt thereof, having the formula

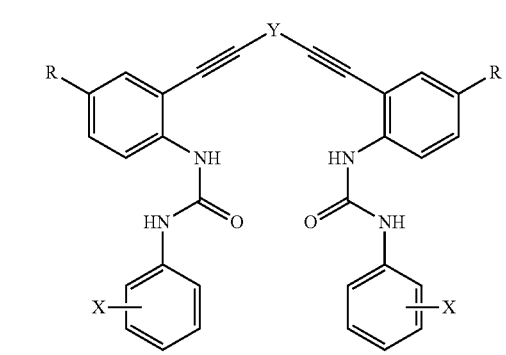

wherein Y is

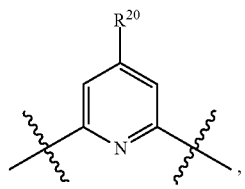

and

R is lower alkyl, substituted lower carboxyl, haloalkyl, or lower alkoxy; X is alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl; and $R^{20}$ is selected from alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

4. The compound of claim 3, wherein X is a polyether moiety, a lower alkoxy, a lower alkyl, or halogen.

5. A compound, or a salt thereof, having the formula

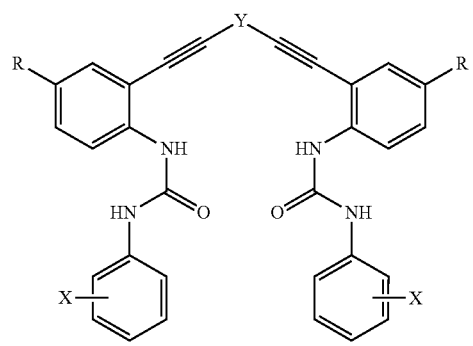

wherein Y is

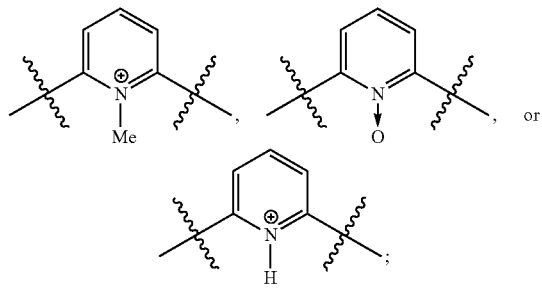

R is lower alkyl, substituted lower carboxyl, haloalkyl, or lower alkoxy; and X is alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

6. The compound of claim 5, wherein X is a polyether moiety, a lower alkoxy, a lower alkyl, or halogen.

7. A compound, or a salt thereof, having the formula

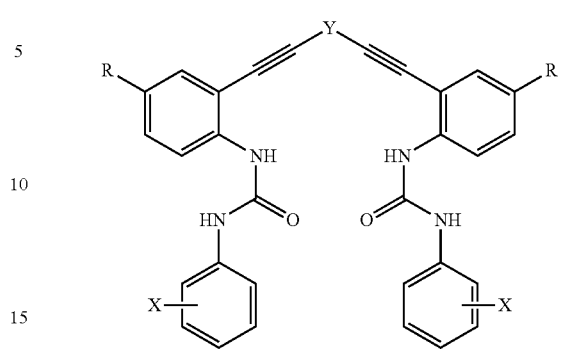

wherein Y represents an optionally substituted aromatic group;

each R is —COOR" wherein R" is a lower alkyl; and

X is alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

8. The compound of claim 7, wherein Y is

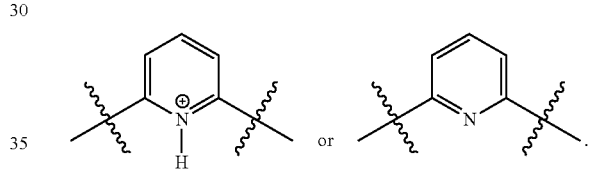

9. A compound, or a salt thereof, having the formula

Formula II

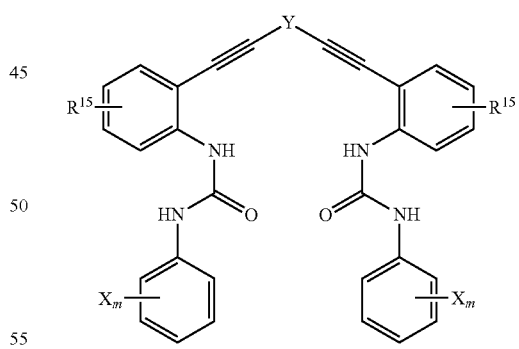

wherein Y represents an optionally substituted aromatic group;

each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

each X is independently halogen; and m is 5.

10. A compound, or a salt thereof, having the formula

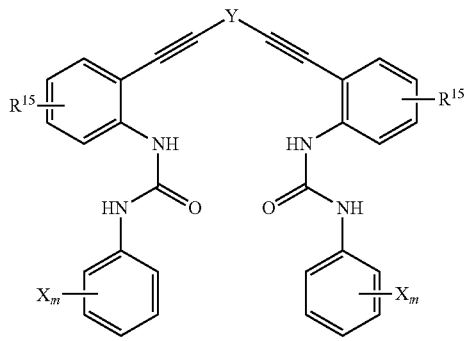

Formula II wherein Y represents an optionally substituted aromatic group;
each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or;
X is a poly(ethylene oxide) moiety; and
m is 1 to 5.

11. The compound of claim 10, wherein m is 1.

12. The compound of claim 1, wherein $R^{20}$ is lower alkyl, nitro, amino, or lower alkoxy.

13. The compound of claim 3, wherein $R^{20}$ is lower alkyl, nitro, amino, or lower alkoxy.

14. The compound of claim 2, wherein $R^1$ is H and $R^2$ is —C(O)NR$^9$R$^{10}$.

15. The compound of claim 14, wherein $R^{10}$ is a phenyl substituted with a polyether moiety, a lower alkoxy, or a lower alkyl.

16. A compound, or a salt thereof, having the formula

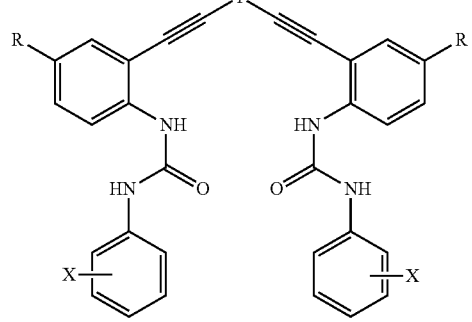

wherein Y represents an optionally substituted aromatic group;
each R is a lower alkyl, X is a para position relative to the position of the —NHC(O)NH— moiety, and X is a polyether moiety.

* * * * *